US008106173B2

(12) United States Patent
Kandimalla et al.

(10) Patent No.: US 8,106,173 B2
(45) Date of Patent: Jan. 31, 2012

(54) STABILIZED IMMUNE MODULATORY RNA (SIMRA) COMPOUNDS FOR TLR7 AND TLR8

(75) Inventors: Ekambar R. Kandimalla, Southboro, MA (US); Tao Lan, Arlington, MA (US); Yukui Li, Newton, MA (US); Dong Yu, Westboro, MA (US); Daqing Wang, Bedford, MA (US); Mallikarjuna Reddy Putta, Burlington, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/697,422

(22) Filed: Apr. 6, 2007

(65) Prior Publication Data
US 2008/0171712 A1  Jul. 17, 2008

Related U.S. Application Data

(60) Provisional application No. 60/790,466, filed on Apr. 7, 2006, provisional application No. 60/827,835, filed on Oct. 2, 2006, provisional application No. 60/863,926, filed on Nov. 1, 2006.

(51) Int. Cl.
*C07H 21/02* (2006.01)
*A61K 48/00* (2006.01)
(52) U.S. Cl. .................... 536/23.1; 514/44 R
(58) Field of Classification Search .............. 514/12, 514/44; 536/23.1, 23.2; 424/280.1
See application file for complete search history.

(56) References Cited

U.S. PATENT DOCUMENTS

| 5,912,332 | A | 6/1999 | Agrawal et al. | |
|---|---|---|---|---|
| 7,255,868 | B2 * | 8/2007 | Fearon et al. | 424/280.1 |
| 2003/0130186 | A1 * | 7/2003 | Vargeese et al. | 514/12 |
| 2004/0097719 | A1 * | 5/2004 | Agrawal et al. | 536/23.2 |
| 2005/0130918 | A1 * | 6/2005 | Agrawal et al. | 514/44 |
| 2005/0256073 | A1 * | 11/2005 | Lipford et al. | 514/44 |
| 2006/0172966 | A1 * | 8/2006 | Lipford et al. | 514/44 |
| 2007/0142315 | A1 * | 6/2007 | Forsbach et al. | 514/44 |

FOREIGN PATENT DOCUMENTS

WO    WO 2006116458 A2 * 11/2006

OTHER PUBLICATIONS

Scheel et al., 2004, European Journal of Immunology, vol. 34, pp. 537-547.*
Tokunaga et al., "Antitumor Activity of Deoxyribonucleic Acid Fraction From *Mycobacterium bovis* BCG. I. Isolation Physicochemical Characterization, and Antitumor Activity", J. Natl. Cancer Inst., 72(4):955-962 (1984).
Shimada et al., "In Vivo Augmentation of Natural Killer Cell Activity With a Deoxyribonucleic Acid Fraction of BCG", Jpn. J. Cancer Res., 77(8):808-816 (1986).
Yamamoto et al., "In Vitro Augmentation of Natural Killer Cell Activity and Production of Interferon- α/β and -γ with Deoxyribonucleic Acid Fraction from *Mycobacterium bovis* BCG", Jpn. J. Cancer Res., 79(7):866-873 (1986).
Messina et al., "Stimulation of in vitro Murine Lymphocyte Proliferation by Bacterial DNA", J. Immunol., 147:1759-1764 (1991).
Zhao et al., "Effect of Different Chemically Modified Oligodeoxynucleotides on Immune Stimulation", Biochem. Pharmacol., 51:173-182 (1996).
Hemmi et al., "A Toll-Like Receptor Recognizes Bacterial DNA", Nature, 408:740-745 (2000).
Zhao et al., "Modulation of Oligonucleotide-Induced Immune Stimulation by Cyclodextrin Analogs", Biochem. Pharmacol., 52:1537-1544 (1996).
Zhao et al., "Pattern and Kinetics of Cytokine Production Following Administration of Phosphorothioate Oligonucleotides in Mice", Antisense Nuc. Acid Drug Devel., 7:495-502 (1997).
Zhao et al., "Site of Chemical Modifications in CpG Containing Phosphorothioate OligodeoxyNucleotide Modulates Its Immunostimulatory Activity", Bioorg. Med. Chem. Lett., 9:3453-3458 (1999).
Zhao et al., "Immunostimulatory Activity of CpG Containing Phosphorothioate Oligodeoxynucleotide is Modulated by Modification of a Single Deoxynucleoside", Bioorg. Med. Chem. Lett., 10:1051-1054 (2000).
Kandimalla et al., Immunomodulatory Oligonucleotides Containing a Cytosine-Phosphate-2'-deoxy-7-deazaguanosine Motif as Potent Toll-Like Receptor 9 Agonists, Proc. Natl. Acad. Sci. USA, 102(19):6925-6930 (2005).
Kandimalla et al., "A dinucleotide Motif in Oligonucleotides Shows Potent Immunomodulatory Activity and Overrides Species-Specific Recognition Observed With CpG Motif", Proc. Natl. Acad. Sci. USA, 100(24):14303-14308 (2003).
Cong et al., Self-Stabilized CpG DNAs Optimally Activate Human B Cells and Plasmacytoid Dendritic Cells, Biochem. Biophys. Res. Commun., 310:1133-1139 (2003).
Kandimalla et al., "Secondary Structures in CpG Oligonucleotides Affect Immunostimulatory Activity", Biochem. Biophys. Res. Commun., 306:948-953 (2003).
Kandimalla et al., "Divergent Synthetic Nucleotide Motif Recognition Patter: Design and Development of Potent Immunomodulatory Oligodeoxyribonucleotide Agents With Distinct Cytokine Induction Profiles", Nucl. Acids Res., 31(9):2393-2400 (2003).
Yu et al., "Requirement of Nucleobase Proximal to CpG Dinucleotide for Immunostimulatory Activity of Synthetic CpG DNA", Bioorg. Med. Chem., 11:459-464 (2003).
Bhagat et al., "CpG Penta- and Hexadeoxyribonucleotides as Potent Immunomodulatory Agents" Biochem. Biophys. Res. Commun., 300:853-861 (2003).
Yu et al., "Immunomers-Novel 3'-3'-Linked CpG Oligodeoxyribonucleotides as Potent Immunomodulatory Agents", Nucl. Acids Res., 30(20):4460-4469 (2002).

(Continued)

Primary Examiner — Dana Shin
(74) Attorney, Agent, or Firm — Wood, Phillips, Katz, Clark & Mortimer

(57) ABSTRACT

The invention relates to the therapeutic use of stabilized oligoribonucleotides as immune modulatory agents for immune therapy applications. Specifically, the invention provides RNA based oligoribonucleotides with improved nuclease and RNase stability and that have immune modulatory activity through TLR7 and/or TLR8.

14 Claims, 21 Drawing Sheets

OTHER PUBLICATIONS

Yu et al., "Design, Synthesis, and Immunostimulatory Properties of CpG DNAs Containing Alkyl-Linker Substitutions: Role of Nucleosides in the Flanking Sequences", J. Med. Chem., 45:4540-4548 (2002).

Yu et al., "Potent CpG Oligonucleotides Containing Phosphodiester Linkages: In Vitro and in Vivo Immunostimulatory Properties", Biochem. Biophys. Res. Commun., 297:83-90 (2002).

Kandimalla et al., "Conjugation of Ligands at the 5'-End of CpG DNA Affects Immunostimulatory Activity", Bioconjug. Chem., 13:966-974 (2002).

Yu et al., "Immunostimulatory Properties of Phosphorothioate CpG DNA Containing Both 3'-5'- and 2'-5'- Internucleotide Linkages", Nuc. Acids Res., 30(7):1613-1619 (2002).

Yu et al., "Immunostimulatory Activity of CpG Oligonucleotides Containing Non-ionic Methylphosphonate Linkages", Bioorg. Med. Chem., 9:2803-2808 (2001).

Yu et al., "Modulation of Immunostimulatory Activity of CpG Oligonucleotides by Site-Specific Deletion of Nucleobases", Bioorg. Med. Chem. Lett., 11:2263-2267 (2001).

Kandimalla et al., "Effect of Chemical Modifications of Cytosine and Guanine in a CpG-Motif of Oligonucleotides: Structure-Immunostimulatory Activity of Relationships", Bioorg. Med. Chem., 9:807-813 (2001).

Yu et al., "Accessible 5'-End of CpG-Containing Phosphorothioate Oligodeoxynucleotides is Essential for Immunostimulatory Activity", Bioorg. Med. Chem. Lett., 10:2585-2588 (2000).

Putta et al., "Novel Oligodeoxynucleotide Agonists of TLR9 Containing $N^3$-Me-dC or $N^1$-Me-dG Modifications", Nucl. Acids Res., 34(11):3231-3238 (2006).

Diebold et al., "Innate Antiviral Responses by Means of TLR7-Mediated Recognition of Single-Stranded RNA", Science, 303:1529-1531 (2004).

Lund et al., "Recognition of Single-Stranded RNA Viruses by Toll-Like Receptor 7", Proc. Natl. Acad. Sci. USA, 101(15):5598-5603 (2004).

Heil et al., "Species-Specific Recognition of Single-Stranded RNA Via Toll-Like Receptor 7 and 8", Science, 303:1526-1529 (2004).

Triantafilou et al., "TLR8 and TLR 7 are Involved in the Host's Immune Response to Human Parechovirus 1", Eur. J. Immunol. 35:2416-2423 (2005).

Hemmi et al., "Small Anti-Viral Compounds Activate Immune Cells Via the TLR7 MyD88-Dependent Signaling Pathway", Nat. Immunol., 3(2):196-200 (2002).

Jurk et al., "Human TLR7 or TLR8 Independently Confer Responsiveness to the Antiviral Compound R-848", Nat. Immunol., 3(6):499 (2002).

Lee et al., "Molecular Basis for the Immunostimulatory Activity of Guanine Nucleoside Analogs: Activation of Toll-Like Receptor 7", Proc. Natl. Acad. Sci. USA, 100(11):6646-6651 (2003).

Schon et al., "The Small Antitumoral Immune Response Modifier Imiquimod Interacts With Adenosine Receptor Signaling in a TLR7- and TLR8-Independent Fashion", J. Invest. Dermatol., pp. 1-10 (2006).

Kariko et al., "Suppression of RNA Recognition by Toll-Like Receptors: The Impact of Nucleoside Modification and the Evolutionary Origin of RNA", Immunity, 23:165-175 (2005).

Ma et al., "Cationic Lipids Enhance siRNA-Mediated Interferon Response in Mice", Biochem. Biophys. Res. Commun., 330:755-759 (2005).

Leitner et al. "DNA vaccines for non-infectious diseases: new treatments for tumor and allergy"; Expert Opinion in Biological Therapy; 3(4):627-638 (2003).

Hamm et al., "Immunostimulatory RNA is a potent inducer of antigen-specific cytotoxic and humoral immune response in vivo", The Japanese Society for Immunology 2007, International Immunology, vol. 19, No. 3, pp. 297-304.

Forsbach et al., "Identification of RNA sequence motifs stimulating sequence-specific TLR8-dependent immune responses", The Journal of Immunology, 2008; 180 pp. 3729-3738.

Forsbach et al., "Characterization of conserved viral leader RNA arquences that stimulate innate immunity through TLRs", Oligonucleotides, 2007, 17, pp. 405-417.

Stanton et al., "Medicinal chemistry of siRNA delivery", Journal of Medicinal Chemistry Perspective, 2010, 53, pp. 7887-7901.

* cited by examiner

Linear Synthesis of SIMRA Compounds

Linkers for linear synthesis

| ID | Sequence and modification | Stability in 1% human serum |
|---|---|---|
| 31 | 5'-UGCUGCUUCUG-X$_1$-GUCUUCGUCGU-5' | 61% |
| 32 | 5'-X$_7$UGCUGCUUGUG-X-GUGUUCGUCGUX$_7$-5' | 80% |
| 33 | 5'-UGUUGUGUGAC-X-CAGUGUUUGU-5' | 76% |
| 36 | 5'-UGCUGCUUG$_2$UG-X-GUG$_2$UUCGUCGU-5' | 86% |
| 37 | 5'-G$_2$GCUGCUUGUG-X-GUGUUCGUCGG$_2$-5' | 85% |
| 38 | 5'-UGCUGCCUUUG-X-GUUUCCGUCGU-5' | 73% |
| 39 | 5'-GUCCUUGCUUG-X-GUUCGUUCCUG-5' | 77% |
| 40 | 5'-GUCCUUUGCUG-X-GUCGUUUCCUG-5' | 82% |
| 41 | 5'-X$_3$UGCUGCUUGUG-X-GUCGUCGUCGUX$_3$-5' | 72% |
| 42 | 5'-XUGCUGCUUGUG-X-GUGUUCGUCGUX-5' | 77% |
| 43 | 5'-X$_7$UGCUGCUUGCUG-X-GUCGUCGUCGUX$_7$-5' | 82% |
| 45 | 5'-UUGCUGCUUGCU-X-UCGUUGUCGUU-5' | 82% |
| 47 | 5'-UUGGUUGUUUG-X-GUUUGUUGGUU-5' | 94% |
| 57 | 5'-UG$_3$CUGCUUCUG-X-GUCUUCGUCG$_3$U-5' | 54% |
| 58 | 5'-UGG$_4$UGCUUCUG-X-GUCUUCGUG$_4$GU-5' | 89% |

Figure 5E

```
                          SEQUENCE LISTING

<160> NUMBER OF SEQ ID NOS: 127

<210> SEQ ID NO 1
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ugcugcuucu g                                                          11

<210> SEQ ID NO 2
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cugugcuucu c                                                          11

<210> SEQ ID NO 3
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ucugugcuuc u                                                          11

<210> SEQ ID NO 4
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
```

<223> OTHER INFORMATION: inosine

<400> SEQUENCE: 4
uncaancuun c                                                              11

<210> SEQ ID NO 5
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gugugugugu g                                                              11

<210> SEQ ID NO 6
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6 ugcugcuu                                                                   8

<210> SEQ ID NO 7
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ugcugcuucu gugu                                                           14

<210> SEQ ID NO 8
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ugcugcuucu gugucug                                                        17

<210> SEQ ID NO 9
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: dU
<220> FEATURE:
<221> NAME/KEY: modified_base
<222> LOCATION: (4)..(4)
<223> OTHER INFORMATION: dU
<220> FEATURE:
<221> NAME/KEY: modified_base
<222> LOCATION: (7)..(8)
<223> OTHER INFORMATION: dU
<220> FEATURE:
<221> NAME/KEY: modified_base

```
<222> LOCATION: (10)..(10)
<223> OTHER INFORMATION: dU

<400> SEQUENCE: 9
ugcugcuucu g                                                            11

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: riboT
<220> FEATURE:
<221> NAME/KEY: modified_base
<222> LOCATION: (4)..(4)
<223> OTHER INFORMATION: riboT
<220> FEATURE:
<221> NAME/KEY: modified_base
<222> LOCATION: (7)..(8)
<223> OTHER INFORMATION: riboT
<220> FEATURE:
<221> NAME/KEY: modified_base
<222> LOCATION: (10)..(10)
<223> OTHER INFORMATION: riboT

<400> SEQUENCE: 10
tgctgcttct g                                                            11

<210> SEQ ID NO 11
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-G
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 11
ugcugcuucu g                                                            11

<210> SEQ ID NO 12
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-G

<400> SEQUENCE: 12
guccuucaac u                                                            11

<210> SEQ ID NO 13
```

```
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
guccuucaac u                                                             11

<210> SEQ ID NO 14
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-G
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 14
ugcugcuucu g                                                             11

<210> SEQ ID NO 15
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-G

<400> SEQUENCE: 15
guccuucaac u                                                             11

<210> SEQ ID NO 16
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: loxoribin

<400> SEQUENCE: 16
nuccuucaac u                                                             11

<210> SEQ ID NO 17
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (2)..(2)
<223> OTHER INFORMATION: loxoribin
<220> FEATURE:
<221> NAME/KEY: modified_base
<222> LOCATION: (5)..(5)
<223> OTHER INFORMATION: loxoribin
<220> FEATURE:
<221> NAME/KEY: modified_base
<222> LOCATION: (11)..(11)
<223> OTHER INFORMATION: loxoribin

<400> SEQUENCE: 17
uncuncuucu n                                                          11

<210> SEQ ID NO 18
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: inosine
<220> FEATURE:
<221> NAME/KEY: modified_base
<222> LOCATION: (5)..(5)
<223> OTHER INFORMATION: inosine
<220> FEATURE:
<221> NAME/KEY: modified_base
<222> LOCATION: (11)..(11)
<223> OTHER INFORMATION: inosine

<400> SEQUENCE: 18
uncuncuucu n                                                          11

<210> SEQ ID NO 19
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine

<400> SEQUENCE: 19
nuccuucaac u                                                          11

<210> SEQ ID NO 20
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Me-ribo-U
<220> FEATURE:
<221> NAME/KEY: modified_base
<222> LOCATION: (2)..(2)
<223> OTHER INFORMATION: 2'-O-Me-ribo-G

<400> SEQUENCE: 20
ugcugcuucu g                                                          11

<210> SEQ ID NO 21
```

```
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ugcugcuucu g                                                          11

<210> SEQ ID NO 22
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Me-ribo-U
<220> FEATURE:
<221> NAME/KEY: modified_base
<222> LOCATION: (2)..(2)
<223> OTHER INFORMATION: 2'-O-Me-ribo-G

<400> SEQUENCE: 22
ugcugcuucu g                                                          11

<210> SEQ ID NO 23
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-O-Me-ribo-U

<400> SEQUENCE: 23
ugcugcuucu g                                                          11

<210> SEQ ID NO 24
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: 2'-O-Me-ribo-C

<400> SEQUENCE: 24
ugcugcuucu                                                            11

<210> SEQ ID NO 25
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ugcugcuacu g                                                          11
```

```
<210> SEQ ID NO 26
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ugcugcuugu g                                                              11

<210> SEQ ID NO 27
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ugcugcugcu g                                                              11

<210> SEQ ID NO 28
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ugcugcuuau g                                                              11

<210> SEQ ID NO 29
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-G
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (9)..(9)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 29
ugcugcuugu g                                                              11

<210> SEQ ID NO 30
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ugcugcuugu g                                                              11
```

```
<210> SEQ ID NO 31
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ugcugcuucu g                                                          11

<210> SEQ ID NO 32
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ugcugcuugu g                                                          11

<210> SEQ ID NO 33
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uguuguguga c                                                          11

<210> SEQ ID NO 34
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
cuggcggccu u                                                          11

<210> SEQ ID NO 35
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-G
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 35
ugcugcuugu g                                                          11

<210> SEQ ID NO 36
<211> LENGTH: 11
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: ara-G

<400> SEQUENCE: 36
ugcugcuugu g                                                            11

<210> SEQ ID NO 37
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: ara-G

<400> SEQUENCE: 37
ggcugcuugu g                                                            11

<210> SEQ ID NO 38
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ugcugccuuu g                                                            11

<210> SEQ ID NO 39
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
guccuugcuu g                                                            11

<210> SEQ ID NO 40
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
guccuuugcu g                                                            11

<210> SEQ ID NO 41
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
```

-continued ugcugcugcu g    11

<210> SEQ ID NO 42
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 42
ugcugcuugu g    11

<210> SEQ ID NO 43
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 43
ugcugcugcu g    11

<210> SEQ ID NO 44
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 44
uugcccuugc c    11

<210> SEQ ID NO 45
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 45
uugcuguugc u    11

<210> SEQ ID NO 46
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 46 cuuggugug u    11

<210> SEQ ID NO 47
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 47
uugguuguuu g    11

```
<210> SEQ ID NO 48
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
cuuuggugug u                                                          11

<210> SEQ ID NO 49
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
uugguuguuu g                                                          11

<210> SEQ ID NO 50
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
guccuugcuu g                                                          11

<210> SEQ ID NO 51
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: phoso-U

<400> SEQUENCE: 51
ugcugcuugu g                                                          11

<210> SEQ ID NO 52
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ugcugcuugu g                                                          11

<210> SEQ ID NO 53
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
```
ugcugcuugu g                                                    11

<210> SEQ ID NO 54
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ugcugcuugu g                                                    11

<210> SEQ ID NO 55
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-G
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 55
ugcugcuucu g                                                    11

<210> SEQ ID NO 56
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ugcugcuugu g                                                    11

<210> SEQ ID NO 57
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 6-thio-G

<400> SEQUENCE: 57
ugcugcuucu g                                                    11

<210> SEQ ID NO 58
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (3)..(3)
<223> OTHER INFORMATION: 1(beta-D-ribofuranosyl)-2-oxo-7-deaza-8-methyl-
      purine

<400> SEQUENCE: 58
ugnugcuucu g                                                              11

<210> SEQ ID NO 59
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(4)
<223> OTHER INFORMATION: 7-deaza-G
<220> FEATURE:
<221> NAME/KEY: modified_base
<222> LOCATION: (7)..(7)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 59
uugguuguuu g                                                              11

<210> SEQ ID NO 60
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-G
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 60
ugcugccuuu g                                                              11

<210> SEQ ID NO 61
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-G
<220> FEATURE:
<221> NAME/KEY: modified_base
<222> LOCATION: (7)..(7)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G
```

```
<400> SEQUENCE: 61
guccuugcuu g                                                              11

<210> SEQ ID NO 62
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-G
<220> FEATURE:
<221> NAME/KEY: modified_base
<222> LOCATION: (8)..(8)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 62
guccuuugcu g                                                              11

<210> SEQ ID NO 63
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-G
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 63
ugcugcuucu g                                                              11

<210> SEQ ID NO 64
<211> LENGTH: 3
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 7-deaza-G

<400> SEQUENCE: 64 cug                                                                        3

<210> SEQ ID NO 65
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (3)..(3)
<223> OTHER INFORMATION: 7-deaza-G
<220> FEATURE:
<221> NAME/KEY: modified_base
<222> LOCATION: (6)..(6)
<223> OTHER INFORMATION: 7-deaza-G
<220> FEATURE:
<221> NAME/KEY: modified_base
<222> LOCATION: (9)..(9)
<223> OTHER INFORMATION: 7-deaza-G

<400> SEQUENCE: 65
uugcuguugc u                                                        11

<210> SEQ ID NO 66
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-G
<220> FEATURE:
<221> NAME/KEY: modified_base
<222> LOCATION: (7)..(7)
<223> OTHER INFORMATION: 7-deaza-G

<400> SEQUENCE: 66
ugccuugaac u                                                        11

<210> SEQ ID NO 67
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 67
uucugcuucu g                                                        11

<210> SEQ ID NO 68
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 68
uucugcuucu g                                                        11
```

```
<210> SEQ ID NO 69
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 69
guccuucucu g                                                         11

<210> SEQ ID NO 70
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-G
<220> FEATURE:
<221> NAME/KEY: modified_base
<222> LOCATION: (7)..(7)
<223> OTHER INFORMATION: 7-deaza-G
<220> FEATURE:
<221> NAME/KEY: modified_base
<222> LOCATION: (9)..(9)
<223> OTHER INFORMATION: 7-deaza-G

<400> SEQUENCE: 70
uguuruguga c                                                         11

<210> SEQ ID NO 71
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
uugguuguuu g                                                         11

<210> SEQ ID NO 72
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
guccuugcuu g                                                         11

<210> SEQ ID NO 73
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 73
uugguuguuu g                                                          11

<210> SEQ ID NO 74
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
guccuugcuu g                                                          11

<210> SEQ ID NO 75
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ugcugcuugu g                                                          11

<210> SEQ ID NO 76
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
ugcugcuucu ggacaugucc ag                                              22

<210> SEQ ID NO 77
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
ugcugcuucu gugauaucac ag                                              22

<210> SEQ ID NO 78
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ugcugcuucu gaauuaauuc ag                                              22

<210> SEQ ID NO 79
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
```
ugcugcuucu ggacuagucc ag    22

<210> SEQ ID NO 80
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ugcugcuucu gugauaucac ag    22

<210> SEQ ID NO 81
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
aguugaagga cugcugcuuc ug    22

<210> SEQ ID NO 82
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
guccuucaac ucagaagcag ca    22

<210> SEQ ID NO 83
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
aguugaagga c    11

<210> SEQ ID NO 84
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
guccuucaac u    11

<210> SEQ ID NO 85
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(6)
<223> OTHER INFORMATION: inosine

```
<400> SEQUENCE: 85 cccnnnccc                                                                9

<210> SEQ ID NO 86
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
agaagcuucu g                                                            11

<210> SEQ ID NO 87
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
ugaagcuucu g                                                            11

<210> SEQ ID NO 88
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uugguuguuu g                                                            11

<210> SEQ ID NO 89
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
guccuugcuu g                                                            11

<210> SEQ ID NO 90
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
ucugaauuca g                                                            11

<210> SEQ ID NO 91
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
```
guuugcacaa c                                                    11

<210> SEQ ID NO 92
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
gcacacuugu u                                                    11

<210> SEQ ID NO 93
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
cacuguugag a                                                    11

<210> SEQ ID NO 94
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
cacuguugac a                                                    11

<210> SEQ ID NO 95
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
aacuguugac c                                                    11

<210> SEQ ID NO 96
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
caacgaccug u                                                    11

<210> SEQ ID NO 97
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
agcacaacug u                                                    11

```
<210> SEQ ID NO 98
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ugcugagugu u                                                           11

<210> SEQ ID NO 99
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
aguguuuucu g                                                           11

<210> SEQ ID NO 100
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ugcugcuucu g                                                           11

<210> SEQ ID NO 101
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
ugcugcuucu g                                                           11

<210> SEQ ID NO 102
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
aguguuuucu g                                                           11

<210> SEQ ID NO 103
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
caacgaaccc u                                                           11

<210> SEQ ID NO 104
```

```
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-G
<220> FEATURE:
<221> NAME/KEY: modified_base
<222> LOCATION: (7)..(7)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 104
guccuugcuu g                                                          11

<210> SEQ ID NO 105
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-G
<220> FEATURE:
<221> NAME/KEY: modified_base
<222> LOCATION: (7)..(7)
<223> OTHER INFORMATION: 7-deaza-G
<220> FEATURE:
<221> NAME/KEY: modified_base
<222> LOCATION: (11)..(1)
<223> OTHER INFORMATION: 7-deaza-G

<400> SEQUENCE: 105
guccuugcuu g                                                          11

<210> SEQ ID NO 106
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 106
uucugcuucu g                                                          11

<210> SEQ ID NO 107
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
```

```
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 107
uucugcuucu g                                                              11

<210> SEQ ID NO 108
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 108
uucugcuucu g                                                              11

<210> SEQ ID NO 109
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-G
<220> FEATURE:
<221> NAME/KEY: modified_base
<222> LOCATION: (7)..(7)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 109
guccuugcuu g                                                              11

<210> SEQ ID NO 110
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-G
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 110
ugcugccuuu g                                                              11
```

```
<210> SEQ ID NO 111
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-G
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 111
ugcugccuuu g                                                          11

<210> SEQ ID NO 112
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-G
<220> FEATURE:
<221> NAME/KEY: modified_base
<222> LOCATION: (8)..(8)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 112
guccuuugcu g                                                          11

<210> SEQ ID NO 113
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-G
<220> FEATURE:
<221> NAME/KEY: modified_base
<222> LOCATION: (8)..(8)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 113
guccuuugcu g                                                          11

<210> SEQ ID NO 114
<211> LENGTH: 11
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 114
ugcugcuugu g                                                            11

<210> SEQ ID NO 115
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
gcugccuuug                                                              10

<210> SEQ ID NO 116
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
ugcugcuugu g                                                            11

<210> SEQ ID NO 117
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
ugcugcuugu g                                                            11

<210> SEQ ID NO 118
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(6)
<223> OTHER INFORMATION: inosine
<220> FEATURE:
<221> NAME/KEY: modified_base
<222> LOCATION: (10)..(11)
<223> OTHER INFORMATION: inosine

<400> SEQUENCE: 118
cccnnncccn n                                                            11

<210> SEQ ID NO 119
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
``` ttttttttttt ttttt                                                    15

<210> SEQ ID NO 120
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120 ttttttttttt ttttt                                                    15

<210> SEQ ID NO 121
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: dU

<400> SEQUENCE: 121
uuuuuuuuuu uuuuu                                                     15

<210> SEQ ID NO 122
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(4)
<223> OTHER INFORMATION: inosine
<220> FEATURE:
<221> NAME/KEY: modified_base
<222> LOCATION: (7)..(8)
<223> OTHER INFORMATION: inosine

<400> SEQUENCE: 122
ccnnccnncc c                                                         11

<210> SEQ ID NO 123
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(4)
<223> OTHER INFORMATION: inosine
<220> FEATURE:
<221> NAME/KEY: modified_base
<222> LOCATION: (7)..(8)
<223> OTHER INFORMATION: inosine

<400> SEQUENCE: 123 ccnnccnncc                                                           10

<210> SEQ ID NO 124
<211> LENGTH: 11
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-G
<220> FEATURE:
<221> NAME/KEY: modified_base
<222> LOCATION: (5)..(5)
<223> OTHER INFORMATION: 7-deaza-G
<220> FEATURE:
<221> NAME/KEY: modified_base
<222> LOCATION: (11)..(11)
<223> OTHER INFORMATION: 7-deaza-G

<400> SEQUENCE: 124
ugcugcuucu g                                                           11

<210> SEQ ID NO 125
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
cagaagcagc a                                                           11

<210> SEQ ID NO 126
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
ccguugacag                                                             10

<210> SEQ ID NO 127
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
acacgcgugu                                                             10
```

STABILIZED IMMUNE MODULATORY RNA (SIMRA) COMPOUNDS FOR TLR7 AND TLR8

RELATED APPLICATIONS

This application claims the benefit of U.S. Provisional Application Ser. No. 60/790,466, filed on Apr. 7, 2006; U.S. Provisional Application Ser. No. 60/827,835, filed on Oct. 2, 2006 and U.S. Provisional Application Ser. No. 60/863,926, filed on Nov. 1, 2006. The teachings of the above-identified applications are incorporated herein by reference in their entirety.

BACKGROUND OF THE INVENTION

1. Field of the Invention

The invention relates generally to the field of immunology and immunotherapy applications using oligoribonucleotides as immune modulatory agents. More particularly, the invention relates to stabilized immune modulatory RNA (SIMRA) compositions and methods of use thereof. Such compositions and methods are effective at modulating the immune response through Toll-like receptor 8 (TLR8), TLR7 and TLR8, and TLR7 (TLR7).

2. Summary of the Related Art

The immune response involves both an innate and an adaptive response based upon the subset of cells involved in the response. For example, the T helper (Th) cells involved in classical cell-mediated functions such as delayed-type hypersensitivity and activation of cytotoxic T lymphocytes (CTLs) are Th1 cells, whereas the Th cells involved as helper cells for B-cell activation are Th2 cells. The type of immune response is influenced by the cytokines and chemokines produced in response to antigen exposure. Cytokines provide a means for controlling the immune response by effecting the balance of T helper 1 (Th1) and T helper 2 (Th2) cells, which directly effects to type of immune response that occurs. If the balance is toward higher numbers of Th1 cells, then a cell-mediated immune response occurs, which includes activation of cytotoxic T cells (CTLs). When the balance is toward higher numbers of Th2 cells, then a humoral or antibody immune response occurs. Each of these immune response results in a different set of cytokines being secreted from Th1 and Th2 cells. Differences in the cytokines secreted by Th1 and Th2 cells may be the result of the different biological functions of these two subsets.

Th1 cells are involved in the body's innate response to antigen (e.g. viral infections, intracellular pathogens, and tumor cells). The initial response to an antigen can be the secretion of IL-12 from antigen presenting cells (e.g. activated macrophages and dendritic cells) and the concomitant activation of Th1 cells. The result of activating Th1 cells is a secretion of certain cytokines (e.g. IL-2, IFN-gamma and other cytokines) and a concomitant activation of antigen-specific CTLs. Th2 cells are known to be activated in response to bacteria, parasites, antigens, and allergens and may mediate the body's adaptive immune response (e.g. IgE production and eosinophil activation) through the secretion of certain cytokines (e.g. IL-3, IL-4, IL-5, IL-6, IL-9, IL-10, IL-13 and other cytokines) and chemokines. Secretion of certain of these cytokines may result in B-cell proliferation and an increase in antibody production. In addition, certain of these cytokines may stimulate or inhibit the release of other cytokines (e.g. IL-10 inhibits IFN-γ secretion from Th1 cells and IL-12 from dendritic cells). Ultimately, the balance between Th1 and Th2 cells and the cytokines and chemokines released in response to selected stimulus can have an important role in how the body's immune system responds to disease. For example, IFN-α may inhibit hepatitis C, and MIP-1α and MIP-1β (also known as CCL3 and CCL4 respectively) may inhibit HIV-1 infection. Optimal balancing of the Th1/Th2 immune response presents the opportunity to use the immune system to treat and prevent a variety of diseases.

The Th1 immune response can be induced in mammals for example by introduction of bacterial or synthetic DNA containing unmethylated CpG dinucleotides, which immune response results from presentation of specific oligonucleotide sequences (e.g. unmethylated CpG) to receptors on certain immune cells known as pattern recognition receptors (PRRs). Certain of these PRRs are Toll-like receptors (TLRs).

Toll-like receptors (TLRs) are intimately involved in inducing the innate immune response in response to microbial infection. In vertebrates, a family of ten proteins called Toll-like receptors (TLR1 to TLR10) is known to recognize pathogen associated molecular patterns. Of the ten, TLR3, 7, 8, and 9 are known to localize in endosomes inside the cell and recognize nucleic acids (DNA and RNA) and small molecules such as nucleosides and nucleic acid metabolites. TLR3 and TLR9 are known to recognize nucleic acid such as dsRNA and unmethylated CpG dinucleotide present in viral and bacterial and synthetic DNA, respectively. Bacterial DNA has been shown to activate immune system and antitumor activity (Tokunaga T et al., J. Natl. Cancer Inst. (1984) 72:955-962; Shimada S, et al., Jpn. H cancer Res, 1986, 77, 808-816; Yamamoto S, et al., Jpn. J. Cancer Res., 1986, 79, 866-73; Messina, J, et al., J. Immunolo. (1991) 147:1759-1764). Other studies using antisense oligonucleotides containing CpG dinucleotides have shown stimulation of an immune response (Zhao Q, et al., Biochem. Pharmacol. 1996, 26, 173-82) Subsequent studies showed that TLR9 recognizes unmethylated CpG motifs present in bacterial and synthetic DNA (Hemmi H, et al., Nature. (2000) 408:740-5). Other modifications of CpG-containing phosphorothioate oligonucleotides can also affect their ability to act as modulators of immune response through TLR9 (see, e.g., Zhao et al., *Biochem. Pharmacol.* (1996) 51:173-182; Zhao et al., *Biochem Pharmacol.* (1996) 52:1537-1544; Zhao et al., *Antisense Nucleic Acid Drug Dev.* (1997) 7:495-502; Zhao et al., *Bioorg. Med. Chem. Lett.* (1999) 9:3453-3458; Zhao et al., *Bioorg. Med. Chem. Lett.* (2000) 10:1051-1054; Yu et al., *Bioorg. Med. Chem. Lett.* (2000) 10:2585-2588; Yu et al., *Bioorg. Med. Chem. Lett.* (2001) 11:2263-2267; and Kandimalla et al., *Bioorg. Med. Chem.* (2001) 9:807-813). In addition, structure activity relationship studies have allowed identification of synthetic motifs and novel DNA-based structures that induce specific immune response profiles that are distinct from those resulting from unmethylated CpG dinucleotides. (Kandimalla E R, et al., *Proc Natl Acad Sci U.S.A.* (2005) 102:6925-30. Kandimalla E R, et al., *Proc Natl Acad Sci U S A.* (2003) 100:14303-8. Cong Y P, et al., *Biochem Biophys Res Commun.* (2003) 310:1133-9. Kandimalla E R, et al., *Biochem Biophys Res Commun.* (2003) 306:948-53. Kandimalla E R, et al., *Nucleic Acids Res.* (2003) 31:2393-400. Yu D, et al., *Bioorg Med. Chem.* (2003) 11:459-64. Bhagat L, et al., *Biochem Biophys Res Commun.* (2003) 300:853-61. Yu D, et al., *Nucleic Acids Res.* (2002) 30:4460-9. Yu D, et al., *J Med. Chem.* (2002) 45:4540-8. Yu D, et al., *Biochem Biophys Res Commun.* (2002) 297:83-90. Kandimalla E R, et al., *Bioconjug Chem.* (2002) 13:966-74. Yu D, K et al., *Nucleic Acids Res.* (2002) 30:1613-9. Yu D, et al., *Bioorg Med. Chem.* (2001) 9:2803-8. Yu D, et al., *BioorgMed Chem. Lett.* (2001) 11:2263-7. Kandimalla E R, et al., *Bioorg Med. Chem.* (2001) 9:807-13. Yu D, et al., *Bioorg Med Chem. Lett.* (2000)

10:2585-8, Putta M R, et al., *Nucleic Acids Res.* (2006) 34:3231-8) However, until recently, natural ligands for TLR7 and TLR8 were unknown.

It has been shown that TLRs 7 and 8 recognize viral and synthetic single-stranded RNAs, and small molecules, including a number of nucleosides (Diebold, S. S., et al., *Science* v: 303, 1529-1531 (2004)). Diebold et al. (*Science*, v303: 1529-1531 (2004)) show that the IFN-α response to influenza virus requires endosomal recognition of influenza genomic RNA and signaling by means of TLR7 and MyD88 and identify ssRNA as a ligand for TLR7. In humans ssRNA is recognized by TLR8 but not by TLR7, whereas murine TLR7 is capable of recognizing ssRNA (Lund J M, et al. *Proc Natl Acad Sci USA.* 2004 Apr. 13; 101(15):5598-603; Heil F. et al. *Science.* 2004; 303:1526-9; Diebold S S, et al., *Science.* 2004; 30:1529-31; Triantafilou K, et al., *Eur J Immunol.* 2005 August; 35(8):2416-23). Certain synthetic compounds, the imidazoquinolones imiquimod (R-837) and resiquimod (R-848) are ligands of TLR7 and TLR8 (Hemmi H et al., (2002) *Nat Immunol* 3:196-200; Jurk M et al., (2002) *Nat Immunol* 3:499). In addition, certain guanosine analogs, such as 7-deaza-G, 7-thia-8-oxo-G (TOG), and 7-allyl-8-oxo-G (loxoribine), have been shown to activate TLR7 at high concentrations [Lee J et al., Proc Natl Acad Sci USA. 2003, 100:6646-51]. However, these small molecules, eg. imiquimod, are also known to act through other receptors (Schon M P, et al., J. Invest Dermatol., 2006, 126, 1338-47)

The lack of any known specific ssRNA motif for TLR7 or TLR8 recognition and the potentially wide range of stimulatory ssRNA molecules suggest that TLR7 and TLR8 can recognize both self and viral RNA. Recently it has been shown that certain GU-rich oligoribonucleotides are immunostimulatory and act through TLR7 and TLR8 (Heil et al. Science, 303: 1526-1529 (2004); Lipford et al. WO03/086280; Wagner et al. WO98/32462) when complexed with N-[1-(2,3-Dioleoyloxy)propyl]-N,N,N trimethylammoniummethylsulfate (DOTAP) or other lipid agents. However, RNA molecules have been used for many years, for example as ribozymes and siRNA, and RNA employed as ribozymes and siRNA contain GU dinucleotides. In addition, a number these RNA molecules have been shown to elicit immune responses through TLR stimulation in the presence of lipids [Kariko et al., Immunity (2005) 23:165-75; Ma Z et al., Biochem Biophys Res Commun., (2005) 330, 755-9]. However, the instability of these RNA molecules has hindered progress in using and applying these molecules in many areas (e.g. prevention and treatment of human disease).

Oligonucleotides and oligodeoxynucleotides containing a ribose or deoxyribose sugar have been used in a wide variety of fields, including but not limited to diagnostic probing, PCR priming, antisense inhibition of gene expression, siRNA, aptamers, ribozymes, and immunotherapeutic agents based on Toll-like Receptors (TLRs). More recently, many publications have demonstrated the use of oligodeoxynucleotides as immune modulatory agents and their use alone or as adjuvants in immunotherapy applications for many diseases, such as allergy, asthma, autoimmunity, cancer, and infectious disease.

The fact that DNA oligonucleotides are recognized by TLR9, while RNA oligonucleotides are recognized by TLR7 and/or TLR8 is most likely due to differences in the structural conformations between DNA and RNA. However, the chemical differences between DNA and RNA also make DNA far more chemically and enzymatically stable than RNA.

RNA is rapidly degraded by ubiquitous extracellular ribonucleases (RNases) which ensure that little, if any, self-ssRNA reaches the antigen-presenting cells. Exonuclease degradation of nucleic acids is predominantly of 3'-nuclease digestion with a smaller percentage through 5'-exonuclease action. In addition to exonuclease digestion, RNA can also be degraded by endonuclease activity of RNAses. RNA-based molecules have so far had to be complexed with lipids to provide nuclease stability.

However, while providing an essential function of preventing autoimmune reactivity, these ribonucleases also present a substantial problem for any synthetic ssRNA molecule designed to be exploited for immunotherapy, as they will rapidly degrade both synthetic and natural ssRNA. To overcome this hurdle, protection of ssRNA molecules from degradation has been attempted by encapsulating the ssRNA in liposomes, condensing it with polyethylenimine, or complexing it to molecules such as N-[1-(2,3 dioleoyloxy)-propyl]-N,N,N-trimethylammonium methyl-sulfate (DOTAP). However, these protective measures are secondary measures applied to a still unstable ssRNA, and the effects of these protective measures on the in vivo efficacy and immune modulatory activity of ssRNA (natural or synthetic) remain unclear.

Thus, a challenge remains to retain the naked RNA such that it continues to be recognized as a ligand for TLR7 and/or TLR8, while improving its stability such that it can be made to be a useful molecule in vivo. Ideally, this challenge might be met through the design of inherently stable RNA-based molecules that can act as new immunotherapic agents, which will find use in a number of clinically relevant applications, such as improving the effects of vaccination when co-administered or treating and/or preventing diseases when invoking or enhancing an immune response is beneficial, for example cancer, autoimmune disorders, airway inflammation, inflammatory disorders, infectious diseases, skin disorders, allergy, asthma or diseases caused by pathogens.

BRIEF SUMMARY OF THE INVENTION

In a first aspect, the invention fills the foregoing need by providing a novel class of stabilized immune modulatory RNA ("SIMRA") compounds, further defined below, and their use for inducing and/or enhancing an immune response. The novel chemical entities according to the invention provide immune response inducing and/or enhancing compounds that are substantially more effective at inducing an immune response and substantially less susceptible to degradation. The methods according to the invention enable modifying the cytokine profile produced by SIMRA for immunotherapy applications.

In one embodiment of the first aspect the invention provides a SIMRA compound as an agonist for TLR8.

In another embodiment of the first aspect the invention provides a SIMRA compound as an agonist for TLR7 and TLR8.

In a further embodiment of the first aspect the invention provides a SIMRA compound as an agonist for TLR7.

In a further embodiment of the first aspect the invention provides a SIMRA compound as an adjuvant.

In a second aspect the invention provides pharmaceutical compositions. These compositions comprise any one of the compositions disclosed in the first three aspects of the invention and a pharmaceutically acceptable carrier.

In a third aspect the invention provides a method for generating an immune response in a vertebrate, the method comprising administering to the vertebrate a SIMRA compound according to the invention in a pharmaceutically effective amount.

In a fourth aspect the invention provides a method for therapeutically treating a vertebrate having a disease or disorder where inducing and/or enhancing an immune response would be beneficial, for example cancer, autoimmune disorders, airway inflammation, inflammatory disorders, infectious diseases, skin disorders, allergy, asthma or diseases caused by pathogens, such method comprising administering to the patient having such a disorder or disease a SIMRA compound according to the invention in a pharmaceutically effective amount.

In a fifth aspect the invention provides a method for preventing a disease or disorder in a vertebrate where inducing and/or enhancing an immune response would be beneficial, for example cancer, an autoimmune disorder, airway inflammation, inflammatory disorders, infectious disease, skin disorders, allergy, asthma or diseases caused by a pathogen, such method comprising administering to a vertebrate that is susceptible to such a disorder or disease a SIMRA compound according to the invention in a pharmaceutically effective amount.

In a sixth aspect the invention provides a method of isolating cells capable of producing cytokine or chemokines (e.g. immune cells, PBMCs), culturing such cells under standard cell culture conditions, treating such cells ex vivo with a SIMRA such that the isolated cells produce or secrete increased levels of cytokines or chemokines, and administering or re-administering the treated cells to a patient in need of cytokine or chemokine therapy for the prevention or treatment of disease.

BRIEF DESCRIPTION OF THE DRAWINGS

FIGS. 11A through 11D demonstrate that SIMRA compounds produce a more robust and distinct cytokine/chemokine profile than loxoribine or 7-deaza-G. FIGS. 11A through 11D further demonstrate that modifications to the backbone, linkers, linkages, and/or caps of SIMRA compounds cause SIMRAs to produce unique and distinct cytokine/chemokine profiles.

FIG. 15 demonstrates that SIMRA compounds are effective at activating different immune cell populations in vivo. More specifically, these data demonstrate that SIMRA compounds can induce effects on select immune cells.

DETAILED DESCRIPTION OF THE PREFERRED EMBODIMENTS

Figure 1:
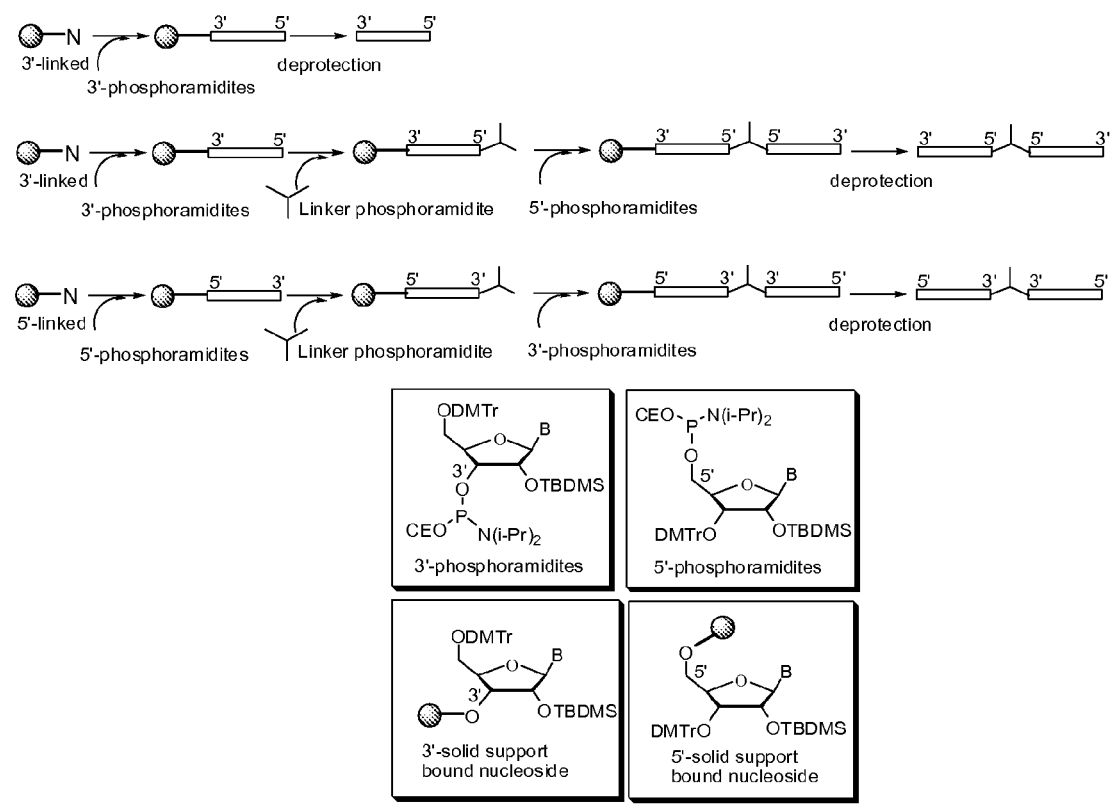
FIG. 1 is a synthetic scheme for the linear synthesis of SIMRA compounds of the invention. DMTr=4,4'-dimethoxytrityl; CE=cyanoethyl.

The invention relates to the therapeutic use of oligoribonucleotides as immune modulatory agents for immunotherapy applications. Specifically, the invention provides RNA-based oligonucleotides with improved in vivo stability that modulate the immune response through TLR7 alone, TLR7 and TLR8 or TLR8 alone (SIMRA compounds). By initiating diverse innate and acquired immune response mechanisms, for example through activation of dendritic cells and other antigen-presenting cells with stable agonists of TLR7 and/or TLR8, or SIMRA compounds, the resulting cytokine profile can lead to the destruction of pathogens, infected cells or tumor cells and development of antigen-specific antibody and CTL responses. The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

The invention provides methods for enhancing the immune response caused by SIMRA compounds used for immunotherapy applications such as, but not limited to, treatment of cancer, autoimmune disorders, asthma, respiratory allergies, food allergies, skin allergies, and bacteria, parasitic, and viral infections in adult and pediatric human and veterinary applications. Thus, the invention further provides SIMRA compounds having optimal levels of immune modulatory effect for immunotherapy and methods for making and using such compounds. In addition, SIMRA compounds of the invention are useful as adjuvants in combination with an agent useful for treating the disease or condition that does not diminish the immune modulatory effect of the SIMRA compound for prevention and treatment of diseases.

DEFINITIONS

The term "2'-substituted ribonucleoside" or "2'-substituted arabinoside" generally includes ribonucleosides or arabinonucleosides in which the hydroxyl group at the 2' position of the pentose moiety is substituted to produce a 2'-substituted or 2'-O-substituted ribonucleoside. In certain embodiments, such substitution is with a lower hydrocarbyl group containing 1-6 saturated or unsaturated carbon atoms, with a halogen atom, or with an aryl group having 6-10 carbon atoms, wherein such hydrocarbyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-amino, 2'-fluoro, 2'-allyl, 2'-O-alkyl and 2'-propargyl ribonucleosides or arabinosides, 2'-O-methylribonucleosides or 2'-O-methylarabinosides and 2'-O-methoxyethoxyribonucleosides or 2'-O-methoxyethoxyarabinosides.

The term "3'", when used directionally, generally refers to a region or position in a polynucleotide or oligonucleotide 3' (toward the 3' position of the sugar) from another region or position in the same polynucleotide or oligonucleotide.

The term "5'", when used directionally, generally refers to a region or position in a polynucleotide or oligonucleotide 5' (toward the 5' position of the sugar) from another region or position in the same polynucleotide or oligonucleotide.

The term "about" generally means that the exact number is not critical. Thus, the number of ribonucleoside residues in the oligoribonucleotides is not critical, and oligoribonucleotides having one or two fewer ribonucleoside residues, or from one to several additional ribonucleoside residues are contemplated as equivalents of each of the embodiments described above.

The term "adjuvant" generally refers to a substance which, when added to an immunogenic agent such as vaccine or antigen, enhances or potentiates an immune response to the agent in the recipient host upon exposure to the mixture.

The term "airway inflammation" generally includes, without limitation, inflammation in the respiratory tract caused by infectious allergens, including asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule.

The term "allergy" generally includes, without limitation, food allergies, respiratory allergies, and skin allergies.

The term "antigen" generally refers to a substance that is recognized and selectively bound by an antibody or by a T cell antigen receptor. Antigens may include but are not limited to peptides, proteins, nucleosides, nucleotides, and combinations thereof. Antigens may be natural or synthetic and generally induce an immune response that is specific for that antigen.

The term "autoimmune disorder" generally refers to disorders in which "self" antigen undergo attack by the immune system.

Blocking 3' or 5' degradation or "cap" or "capping" means that the 3' or 5' end of the oligoribonucleotide is attached to another molecule (e.g. linker, or other non-RNA nucleotide) to sufficiently inhibit nuclease degradation (e.g. 3' exonuclease degradation).

The term "carrier" generally encompasses any excipient, diluent, filler, salt, buffer, stabilizer, solubilizer, oil, lipid, lipid containing vesicle, microspheres, liposomal encapsulation, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences,* 18th Edition, ed. A. Gennaro, Mack Publishing Co., Easton, Pa., 1990.

The term "co-administration" generally refers to the administration of at least two different substances sufficiently close in time to modulate an immune response. Preferably, co-administration refers to simultaneous administration of at least two different substances.

The term "complementary" generally means having the ability to hybridize to a nucleic acid. Such hybridization is ordinarily the result of hydrogen bonding between complementary strands, preferably to form Watson-Crick or Hoogsteen base pairs, although other modes of hydrogen bonding, as well as base stacking can also lead to hybridization.

The term an "effective amount" or a "sufficient amount" generally refers to an amount sufficient to affect a desired biological effect, such as beneficial results. Thus, an "effective amount" or "sufficient amount" will depend upon the context in which it is being administered. An effective amount may be administered in one or more administrations.

The term "immune modulatory oligoribonucleotide" generally refers to an oligoribonucleotide that induces or represses an immune response when administered to a vertebrate, such as a fish, fowl, or mammal.

The term "in combination with" generally means in the course of treating the same disease in the same patient, and includes administering a SIMRA compound and an agent useful for treating the disease or condition that does not diminish the immune modulatory effect of the SIMRA compound in any order, including simultaneous administration, as well as temporally spaced order from a few seconds up to several days apart. Such combination treatment may also include more than a single administration of a SIMRA compound, and/or independently the agent. The administration of the SIMRA compound and the agent may be by the same or different routes.

The term "individual" or "subject" generally refers to a mammal, such as a human. Mammals generally include, but are not limited to, humans, non-human primates, rats, mice, cats, dogs, horses, cattle, cows, pigs, sheep, and rabbits.

The term "linear synthesis" generally refers to a synthesis that starts at one end of the immune modulatory oligoribonucleotide and progresses linearly to the other end. Linear synthesis permits incorporation of either identical or non-identical (in terms of length, base composition and/or chemical modifications incorporated) monomeric units into the immune modulatory oligoribonucleotides.

The term "modified nucleoside" generally is a nucleoside that includes a modified heterocyclic base, a modified sugar moiety, or any combination thereof. In some embodiments, the modified nucleoside is a non-natural pyrimidine or purine nucleoside, as herein described. For purposes of the invention, a modified nucleoside, a pyrimidine or purine analog or non-naturally occurring pyrimidine or purine can be used interchangeably and refers to a nucleoside that includes a non-naturally occurring base and/or non-naturally occurring sugar moiety. For purposes of the invention, a base is considered to be non-natural if it is not guanine, cytosine, adenine or uracil. In some embodiments, the modified nucleoside is a 2'-substituted ribonucleoside an arabinonucleoside or a 2'-deoxy-2'-substituted-arabinoside that can be substituted into selected positions of the oligoribonucleotide to improve stability without interfering with TLR7 or TLR8 activity.

The term "modulation" or "stimulation" generally refers to change, such as an increase in a response or qualitative difference in a response, which can arise from eliciting and/or enhancement of a response.

The term "linker" generally refers to any moiety that can be attached to an oligoribonucleotide by way of covalent or non-covalent bonding through a sugar, a base, or the backbone. The linker can be used to attach two or more nucleosides or can be attached to the 5' and/or 3' terminal nucleotide in the oligoribonucleotide. Such linker can be either a non-nucleotidic linker or a nucleotidic linker.

The term "non-nucleotidic linker" generally refers to a chemical moiety other than a nucleotidic linkage that can be attached to an oligoribonucleotide by way of covalent or non-covalent bonding. Preferably such non-nucleotidic linker is from about 2 angstroms to about 200 angstroms in length, and may be either in a cis or trans orientation.

The term "nucleotidic linkage" generally refers to a chemical linkage to join two nucleosides through their sugars (e.g. 3'-3', 2'-3',2'-5', 3'-5') consisting of a phosphate, non-phosphate, charged, or neutral group (e.g., phosphodiester, phosphorothioate or phosphorodithioate) between adjacent nucleosides.

The term "palindromic sequence" generally means self-complimentary or an inverted repeat (i.e., a sequence such as ABCDEE'D'C'B'A' in which A and A', B and B', etc., are bases capable of forming the usual Watson-Crick base pairs. In vivo, such sequences may form intra-molecular or inter-molecular double-stranded structures.

The term "peptide" generally refers to polypeptides that are of sufficient length and composition to affect a biological response, e.g., antibody production or cytokine activity whether or not the peptide is a hapten. The term "peptide" may include modified amino acids (whether or not naturally or non-naturally occurring), where such modifications include, but are not limited to, phosphorylation, glycosylation, pegylation, lipidization, and methylation.

The term "PBMC" generally refers to peripheral blood mononuclear cells.

The term "physiologically acceptable" generally refers to a material that does not interfere with the effectiveness of a SIMRA compound and that is compatible with a biological system such as a cell, cell culture, tissue, or organism. Preferably, the biological system is a living organism, such as a vertebrate.

The term "SIMRA" generally refers to stabilized immune modulatory RNA compounds which are recognized as ligands by TLR7 and/or TLR8, wherein the compounds may contain single-stranded RNA (ssRNA) and/or double-stranded RNA (dsRNA), and modifications to protect (stabilize) its 3' ends (e.g. by blocking 3' degradation or by capping the 3' ends or by linking the 3' ends of two or more oligoribonucleotides), provided that the SIMRA is more stable in vivo than an unmodified oligoribonucleotide and, thus, affect its immune modulatory capabilities. The SIMRA may contain modified oligoribonucleotides. The SIMRA compound may also contain modifications to protect its 5' ends (e.g., by blocking 5' degradation or capping the 5' ends) to further improve the stability of the oligoribonucleotides. The SIMRA can be linear or branched, with nucleic acids being polymers of ribonucleosides linked through, for example, phosphodiester, phosphorothioate, or alternate linkages. A SIMRA may consist of a purine (adenine (A) or guanine (G) or derivatives thereof (e.g. 7-deaza-G and ara-G)) or pyrimidine (cytosine (C) or uracil (U), or derivatives thereof) base covalently attached to a ribose sugar residue, or a derivative thereof.

The term "treatment" generally refers to an approach intended to obtain a beneficial or desired results, which may include alleviation of symptoms, or delaying or ameliorating a disease progression.

The term "viral disease" generally refers to a disease that has a virus as its etiologic agent, including but not limited to hepatitis B, hepatitis C, influenza, acquired immunodeficiency syndrome (AIDS), and herpes zoster.

In a first aspect, the invention provides SIMRA compound. The present inventors have discovered that modification of an immune modulatory oligoribonucleotide to protect its 3' end (e.g. by blocking 3' degradation or capping the 3' end or by linking the 3' ends of two or more oligoribonucleotides) surprisingly affects its immune modulatory capabilities. In addition, it has been determined that this protection surprisingly improves the stability of the oligoribonucleotides, removing the need for lipid association or other means of protection. Further, blocking 5' degradation or capping the 5' end can further improve the stability of the oligoribonucleotide.

In the present invention activation of TLR8 and induction of an immune response (e.g. changes in cytokine profile) with novel SIMRA compounds is demonstrated. Moreover, the incorporation of certain chemical modification(s) in such human TLR8 activating RNAs can also activate TLR7, resulting in an immune response and a change in cytokine/chemokine profiles. Thus, the present inventors have surprisingly discovered that through activation of TLR8 and/or TLR7 the cytokine/chemokine profile associated therewith can be modulated by using modified chemical structures, including modified bases, modified sugars, backbone, linkers, linkages, and/or caps as part of an immune modulatory oligoribonucleotide.

In one embodiment, the invention provides an immune modulatory compound comprising at least two RNA-based oligonucleotides linked at their 3' ends, or an internucleoside linkage or a functionalized nucleobase or sugar to a non-nucleotidic linker. Such embodiment of the invention may modulatory compound has a structure including, but not limited to, those as detailed in Formulas I-X in Table 1.

TABLE 1

Oligoribonucleotide Formulas I-X

| Formula I | 5' Domain A 3'—X—3' Domain B 5' |
| --- | --- |
| Formula II a | 5' Domain A 3'—X—5' Domain B 3'—X—3' Domain C 5' |
| Formula II b | 3' Domain A 5'—X—5' Domain B 3'—X—3' Domain C 5' |
| Formula III | 5' Domain A 3'—X—5' Domain B 3'—X—5' Domain C 3'—X—3' Domain D 5' |
| Formula IV | 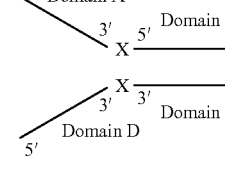 |
| Formula V | 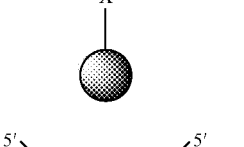 |
| Formula VI | 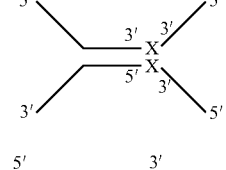 |
| Formula VII | 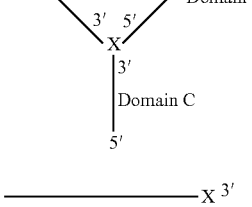 |
| Formula VIII | 5'————X 3' / 3' X————5' |
| Formula IX | 5'—Domain A—X—Domain B—3' / 3'—Domain B—X—Domain A—5' |
| Formula X | $\left[ 5'\text{—Domain A—}X\text{—Domain B—}3'\ 5'\text{—Domain A—}X\text{—Domain B—}3' \atop 3'\text{—Domain B—}X\text{—Domain A—}5' \right]_n$ | have at least one accessible 5' end. It has been determined that this structure provides further stability (e.g. inhibition of exonuclease activity) to the SIMRA compounds without the need for lipid association or other protection. The 5'-terminus of the SIMRA is not modified in such a way as to prevent the SIMRA compound from modulating an immune response through TLR7 and/or TLR8.

In another embodiment of this aspect of the invention comprises at least two oligoribonucleotides, wherein the immune Domains A, B, C, and D may be independently from about 2 to about 35 ribonucleotides, and in some embodiments from about 2 to about 20, or from about 2 to about 12, or from about 2 to about 11 or from about 2 to about 8 ribonucleotides in length. Domains A, B, C, and/or D may or may not be identical. Domains A, B, C, and D may independently be 5'-3' or 2'-5' RNA having or not having a self-complementary domain, a homo or hetero ribonucleotide sequence, or a linker. "n" may be from 1 to an unlimited number.

"X" is a linker joining or capping Domains A, B, C, and/or D that may be though a 3' or 5' linkage, a phosphate group, a non-RNA nucleotide, or a non-nucleotidic linker that may be aliphatic, aromatic, aryl, cyclic, chiral, achiral, a peptide, a carbohydrate, a lipid, a fatty acid, mono- tri- or hexapolyethylene glycol, or a heterocyclic moiety, or combinations thereof.

In a further embodiment, the invention provides a SIMRA compound comprising at least two oligoribonucleotides linked by a non-nucleotide linker, wherein the sequences of the immune modulatory oligoribonucleotides may be at least partially self-complementary. As would be recognized by one skilled in the art, the complementary sequence of the oligoribonucleotides allows for intermolecular hydrogen bonding thereby giving the oligoribonucleotides secondary structure. Additional oligoribonucleotides can bind together thereby creating a chain, or multimers, of oligoribonucleotides according to the invention.

Similar considerations apply to intermolecular base pairing between immune modulatory oligoribonucleotides of different base sequence. Thus, where a plurality of immune modulatory oligoribonucleotides is used together, the plurality of immune modulatory oligoribonucleotides may, but need not, include sequences that are at least partially complementary to one another. In one embodiment the plurality of immune modulatory oligoribonucleotides includes an immune modulatory oligoribonucleotide having a first sequence and an immune modulatory oligoribonucleotide having a second sequence, wherein the first sequence and the second sequence are at least 50 percent complementary. For example, as between two 8-mers that are at least 50 percent complementary, they may form 4, 5, 6, 7, or 8 G-C, A-U, and/or G-U wobble basepairs. Such basepairs may, but need not necessarily, involve bases located at either end of the complementary immune modulatory oligoribonucleotides. The degree of complementarity may depend on the alignment between immune modulatory oligoribonucleotides, and such alignment may or may not include single- or multiple-nucleoside overhangs. In other embodiments, the degree of complementarity is at least 60 percent, at least 70 percent, at least 80 percent, at least 90 percent, or even 100 percent.

As would be recognized by one skilled in the art, the depicted immune modulatory compounds may have secondary structure because the sequences of the domains are complementary allowing for intermolecular hydrogen bonding. Moreover, as can be imagined from Formulas I through X, additional linked RNA-based oligonucleotides can bind through intermolecular hydrogen bonding thereby creating a chain, or multimers, wherein any number of linked RNA-based oligonucleotides may be incorporated.

In another embodiment, the invention provides an immune modulatory compound comprising at least two RNA-based oligonucleotides linked at their 3' or 5' ends, or through an internucleoside linkage or a functionalized nucleobase or sugar to a non-nucleotidic linker, and wherein a linker (e.g. cap) is attached to at least one 5' end. It has been determined that this structure provides further stability (e.g. inhibition of exonuclease activity) to the SIMRA compounds. The 5'-terminus of the SIMRA is not modified in such a way as to prevent the SIMRA compound from modulating an immune response through TLR7 and/or TLR8.

In some embodiments, the oligoribonucleotides each independently have from about 2 to about 35 ribonucleoside residues. Thus in certain embodiments the oligoribonucleotide can independently be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 ribonucleotides long. Preferably the oligoribonucleotide is from about 4 to about 30 ribonucleoside residues, more preferably from about 4 to about 20 ribonucleoside residues or from about 4 to about 11 ribonucleoside residues. In some embodiments, the immune modulatory oligoribonucleotides comprise oligoribonucleotides have from about 1 to about 18, or from about 1 to about 11, or from about 5 to about 14 ribonucleoside residues. In some embodiments, one or more of the oligoribonucleotides have 11 nucleotides. In the context of immune modulatory oligoribonucleotides, preferred embodiments have from about 1 to about 35 ribonucleotides, preferably from about 5 to about 26 nucleotides, more preferably from about 13 to about 26 ribonucleotides. Preferably, the immune modulatory oligoribonucleotide comprises at least one phosphodiester, phosphorothioate, or phosphorodithioate interribonucleoside linkage.

In preferred embodiments each ribonucleoside unit includes a heterocyclic base and a pentofuranosyl, trehalose, arabinose, 2'-deoxy-2'-substitutedarabinose, 2'-O-substitutedarabinose or hexose sugar group. The ribonucleoside residues can be coupled to each other by any of the numerous known interribonucleoside linkages. Such interribonucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone interribonucleoside linkages. Possible sites of conjugation for the ribonucleotide are indicated in Formula XI, below, wherein B represents a heterocyclic base.

Formula XI

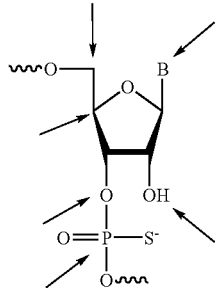

The SIMRA compounds of the invention can include naturally occurring ribonucleosides, modified ribonucleosides, or mixtures thereof.

In the present invention, novel SIMRA compounds are recognized by human TLR8 and incorporation of certain chemical modification(s) in such human TLR8 activating RNAs causes them to be recognized by human TLR7 and induce immune responses. Such chemical modifications include, but are not limited to, guanine analogues such as 7-deaza-G, ara-G, 6-thio-G, Inosine, Iso-G, loxoribine, TOG (7-thio-8-oxo)-G, 8-bromo-G, 8-hydroxy-G, 5-aminoformycin B, Oxoformycin, 7-methyl-G, 9-p-chlorophenyl-8-aza-G, 9-phenyl-G, 9-hexyl-guanine, 7-deaza-9-benzyl-G, 6-Chloro-7-deazaguanine, 6-methoxy-7-deazaguanine, 8-Aza-7-deaza-G(PPG), 2-(Dimethylamino)guanosine, 7-Methyl-6-thioguanosine, 8-Benzyloxyguanosine, 9-Deazaguanosine, and 1-(B-D-ribofuranosyl)-2-oxo-7-deaza-8-methyl-purine. Chemical modifications also include, but are not limited to, adenine analogues such as 9-benzyl-8-hydroxy-2-(2-methoxyethoxy)adenine, 2-Amino-N2-O—, methyladenosine, 8-Aza-7-deaza-A, 7-deaza-A, Vidarabine, 2-Aminoadenosine, N1-Methyladenosine, 8-Azaadenosine, 5-Iodotubercidin. Chemical modifications also include, but are not limited to, cytosine analogues. Chemical modifications also include, but are not limited to, uracil analogues such as 4-thio-U.

The "immune modulatory oligoribonucleotides" according to the invention are SIMRA compounds that comprise at least two oligoribonucleotides linked at their 3'- or 2'-ends or functionalized ribose or functionalized ribonucleobase via a non-nucleotidic or a nucleotidic linker. Several examples of linkers are set forth below. Non-covalent linkages include, but are not limited to, electrostatic interaction, hydrophobic interactions, π-stacking interactions, and hydrogen bonding.

In yet other embodiments, the non-nucleotidic linker is an organic moiety having functional groups that permit attachment to the oligoribonucleotide. Such attachment preferably is by a stable covalent linkage. As a non-limiting example, the linker may be attached to any suitable position on the nucleotide. In some preferred embodiments, the linker is attached to the 3'-hydroxyl. In such embodiments, the linker preferably comprises a hydroxyl functional group, which preferably is attached to the 3'-hydroxyl by means of a phosphate-based linkage like, phosphodiester, phosphorothioate, phosphorodithioate, methylphosphonate or non-phosphate-based linkages.

In some embodiments, the non-nucleotidic linker is a small molecule, macromolecule or biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligoribonucleotides or appended to it, one or more functional groups including, but not limited to, hydroxy, amino, thiol, thioether, ether, amide, thioamide, ester, urea, or thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside.

In some embodiments, the non-nucleotidic linker is an alkyl linker or amino linker. The alkyl linker may be branched or unbranched, cyclic or acyclic, substituted or unsubstituted, saturated or unsaturated, chiral, achiral or racemic mixture. The alkyl linkers can have from about 2 to about 18 carbon atoms. In some embodiments such alkyl linkers have from about 3 to about 9 carbon atoms. Some alkyl linkers include one or more functional groups including, but not limited to, hydroxy, amino, thiol, thioether, ether, amide, thioamide, ester, urea, and thioether. Such alkyl linkers can include, but are not limited to, 1 propanol, 1,2 propanediol, 1,3 propanediol, 1,2,3, propanetriol, triethylene glycol hexaethylene glycol, polyethylene glycollinkers (e.g. [—O—CH2-CH2-]$_n$ (n=1-9)), methyl linkers, ethyl linkers, propyl linkers, butyl linkers, or hexyl linkers. In some embodiments, such alkyl linkers may include peptides or amino acids.

In some embodiments, the non-nucleotidic linker may include, but are not limited to, those listed in Table 2.

TABLE 2

Representative Non-nucleotidic Linkers

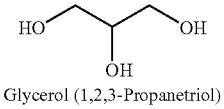
Glycerol (1,2,3-Propanetriol)

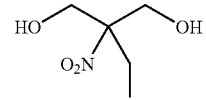
1,1,1-Tris(hydroxymethyl)nitromethane

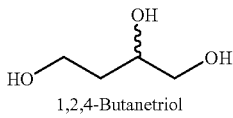
1,2,4-Butanetriol

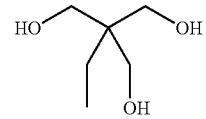
1,1,1-Tris(hydroxymethyl)propane

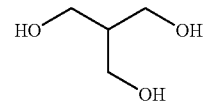
2-(hydroxymethyl)-1,3-propanediol

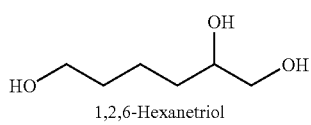
1,2,6-Hexanetriol

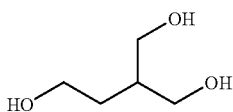
2-(hydroxymethyl)1,4-butanediol

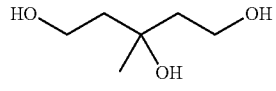
3-Methyl-1,3,5-pentanetriol

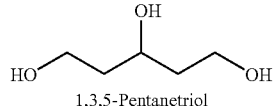
1,3,5-Pentanetriol

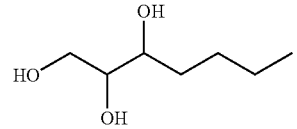
1,2,3-Heptanetriol

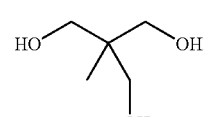
1,1,1-Tris(hydroxymethyl)ethane

TABLE 2-continued

Representative Non-nucleotidic Linkers

2-Amino-2-(hydroxymethyl)-1,3-propanediol

N-[Tris(hydroxymethyl)methyl]acrylamide cis-1,3,5-Cyclohexanetriol 1,3-Di(hydroxyethoxy)-2-hydroxyl-propane cis-1,3,5-Tri(hydroxymethyl)cyclohexane 1,3-Di(hydroxypropoxy)-2-hydroxyl-propane 1,3,5,-Trihydroxyl-benzene 2-Deoxy-D-ribose 3,5,-Di(hydroxymethyl)phenol 1,2,4,-Trihydroxyl-benzene 1,3,5,-Tri(hydroxymethyl)benzene D-Galactoal 1,6-anhydro-β-D-Glucose 4,6-Nitropyrogallol 1,3,5-Tris(2-hydroxyethyl)-Cyanuric acid Gallic acid TABLE 2-continued Representative Non-nucleotidic Linkers

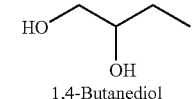
3,5,7-Trihydroxyflavone

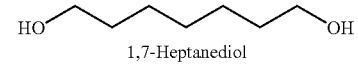
Ethylene glycol 1,5-Pentanediol 1,3-Propanediol 2,4-Pentanediol 1,2-Propanediol 1,6-Hexanediol 1,4-Butanediol 1,2-Hexanediol 1,3-Butanediol 1,5-Hexanediol 2,3-Butanediol 2,5-Hexanediol TABLE 2-continued Representative Non-nucleotidic Linkers 1,4-Butanediol 1,7-Heptanediol 1,8-Octanediol 1,2-Octanediol 1,9-Nonanediol 1,12-Dodecanediol Triethylene glycol Tetraethylene glycol Hexaethylene glycol 2-(1-Aminopropyl)-1,3-propanediol 1,2-Dideoxyribose In some embodiments, the small molecule linker is glycerol or a glycerol homolog of the formula HO—(CH$_2$)$_o$—CH(OH)—(CH$_2$)$_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—(CH$_2$)$_m$—C(O)NH—CH$_2$—CH(OH)—CH$_2$—NHC(O)—(CH$_2$)$_m$—OH, wherein m is an integer from 0 to about 10, from 0 to about 6, from 2 to about 6, or from 2 to about 4

Some non-nucleotidic linkers according to the invention permit attachment of more than two oligoribonucleotides, as depicted in Table 1. For example, the small molecule linker glycerol has three hydroxyl groups to which oligoribonucleotides may be covalently attached. Some immune modulatory oligoribonucleotides according to the invention, therefore, comprise more than two oligoribonucleotides (e.g., a Domain C and so on, the additional domains comprise oligoribonucleotides as defined above for Domains A, B, C, and D) linked at their 3' ends to a non-nucleotidic linker.

In a further embodiment of this aspect of the invention, a SIMRA may contain three or more oligoribonucleotides linked at their 3' or 5' ends, or through an internucleoside linkage or a functionalized nucleobase or sugar to two or more linkers, as depicted in Table 1. The oliogoribonucleotides of this aspect of the invention may have the same or different sequences. The linkers of this aspect of the invention may be the same or different.

Figure 2:
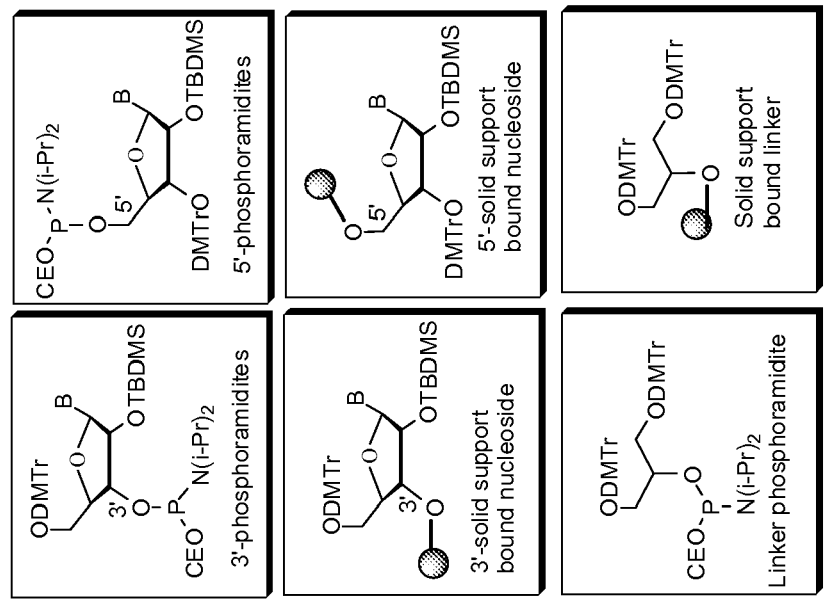
FIG. 2 is a synthetic scheme for the parallel synthesis of SIMRA compounds of the invention. DMTr=4,4'-dimethoxytrityl; CE=cyanoethyl.
Figure 2:
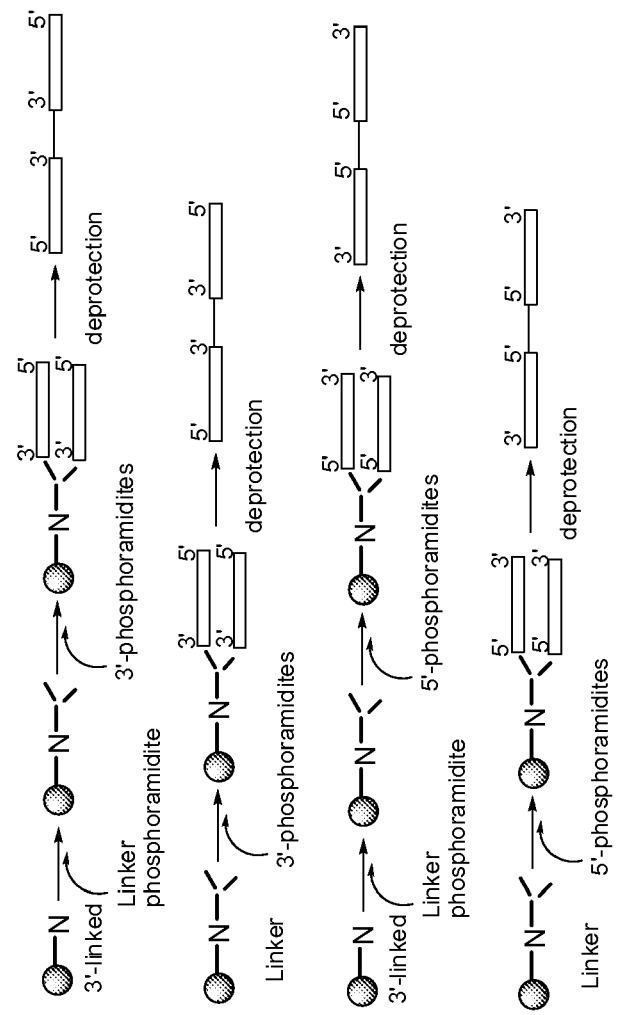
Figure 3:
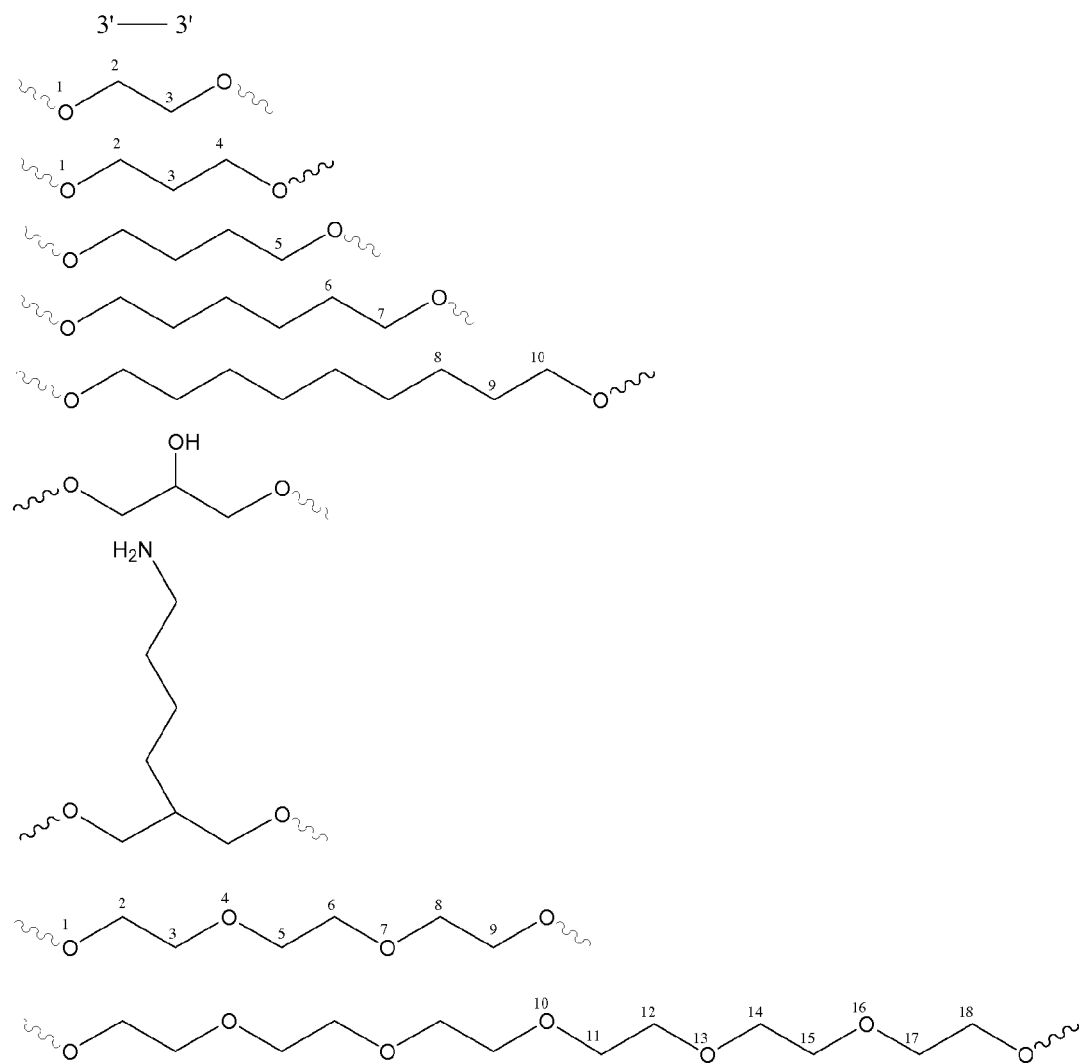
FIG. 3 depicts a group of representative alkyl linkers suitable for linear synthesis of SIMRA compounds of the invention.
Figure 4:
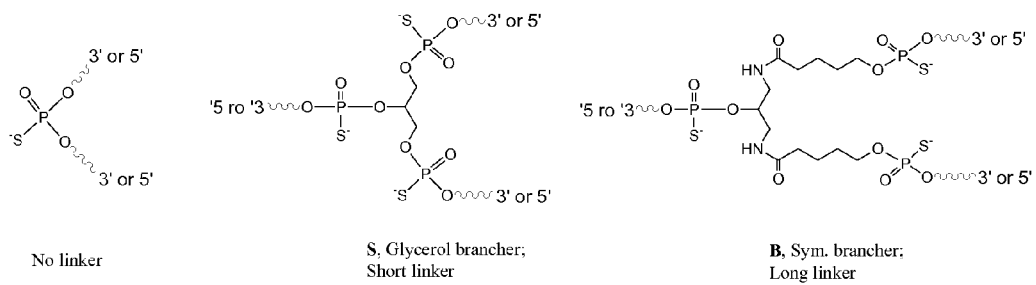
FIG. 4 depicts a group of representative small molecule linkers suitable for parallel synthesis of SIMRA compounds of the invention.
Figure 5:
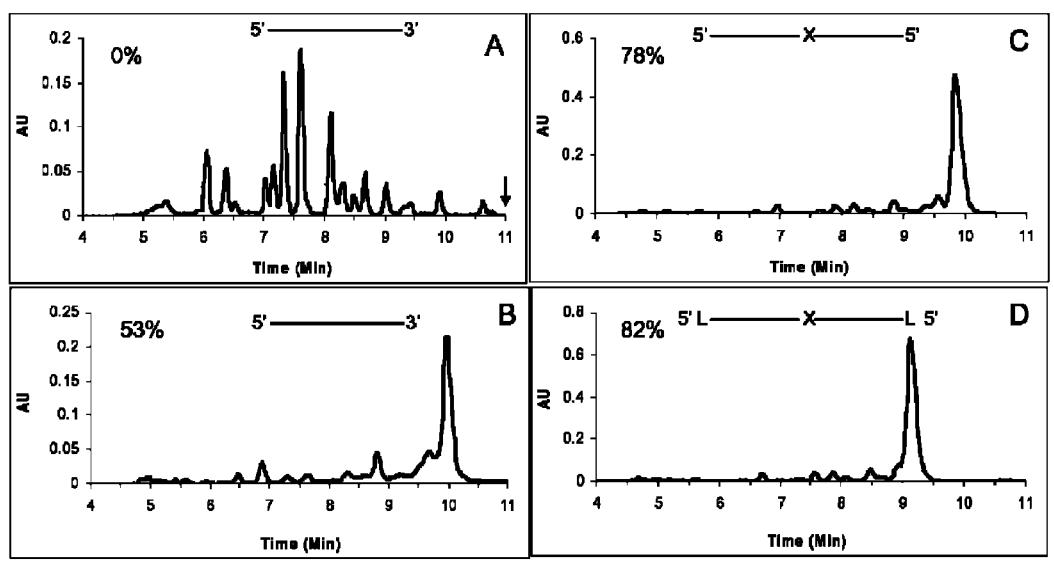
FIG. 5A demonstrates that a natural phosphodiester RNA 20-mer is degraded completely in 1% human serum in less than 10 min.
FIG. 5B demonstrates that phosphorothioate backbone modified RNA of the same sequence is relatively stable under the same conditions and about 50% of intact oligo is present at the end of the 10 min.
FIG. 5C demonstrates that two phosphorothioate backbone modified RNAs attached through their 3'-ends are even more stable and about 78% or more of the intact RNA remains after 10 min, demonstrating the increased stability of the molecule against nuclease degradation.
FIG. 5D demonstrates that attaching linkers or caps at the 5'-ends of 3'-3'-linked phosphorothioate backbone modified RNA modestly increases the stability as compared to that of the RNA without 5'-linkers or caps, indicating that major degradation occurs from the 3'-end.
FIG. 5E demonstrates the stability of additional phosphorothioate backbone modified immunemodulatory compounds of the invention (SEQ ID NOS 31-33, 36-43, 45, 47, 57 & 58).
Figure 6:
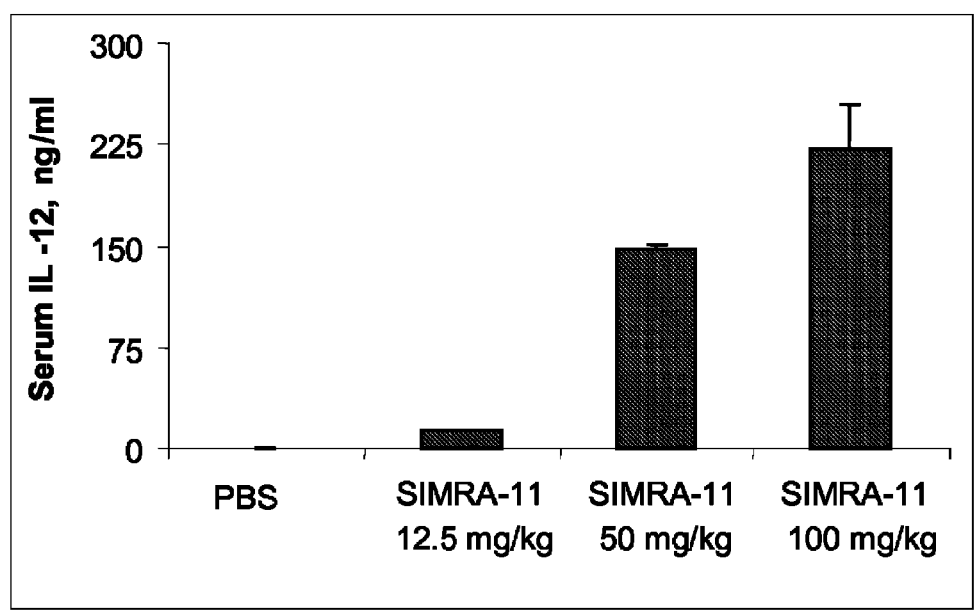
FIG. 6 depicts IL-12 levels, as determined by ELISA, in the serum from C57BL/6 mice 2 hours after subcutaneous administration of a SIMRA compound of the invention, demonstrating that SIMRA compounds (e.g. SEQ ID NO 11) can induce IL-12 secretion in vivo.
Figure 7:
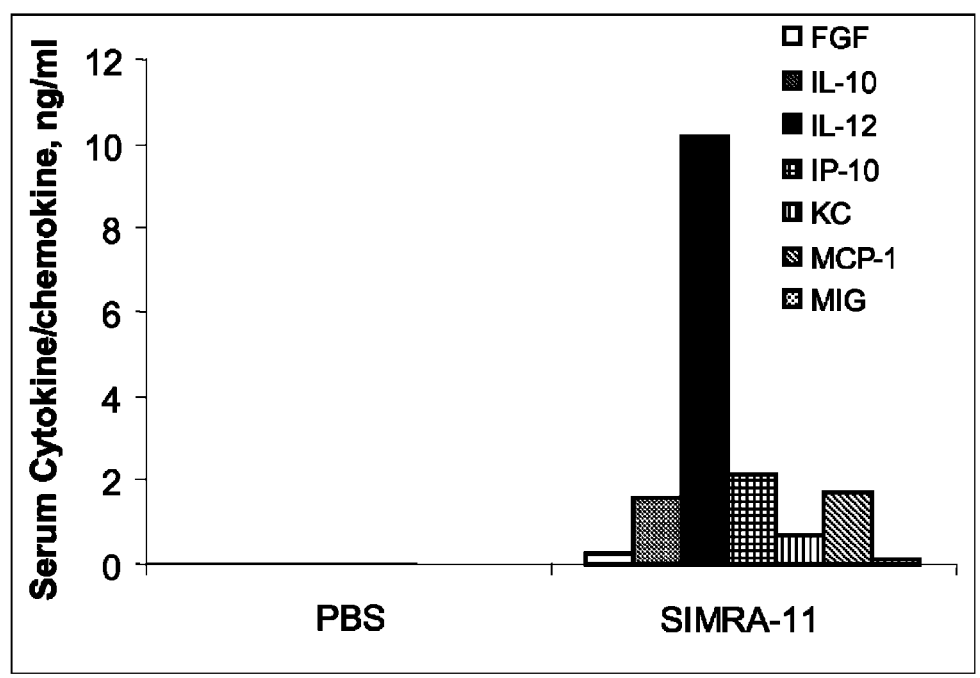
FIG. 7 depicts a cytokine profile in serum from mice administered with 100 mg/kg dose of a SIMRA compound of the invention, demonstrating that SIMRA compounds (e.g. SEQ ID NO 11) induce cytokine production following in vivo administration.
Figure 8:
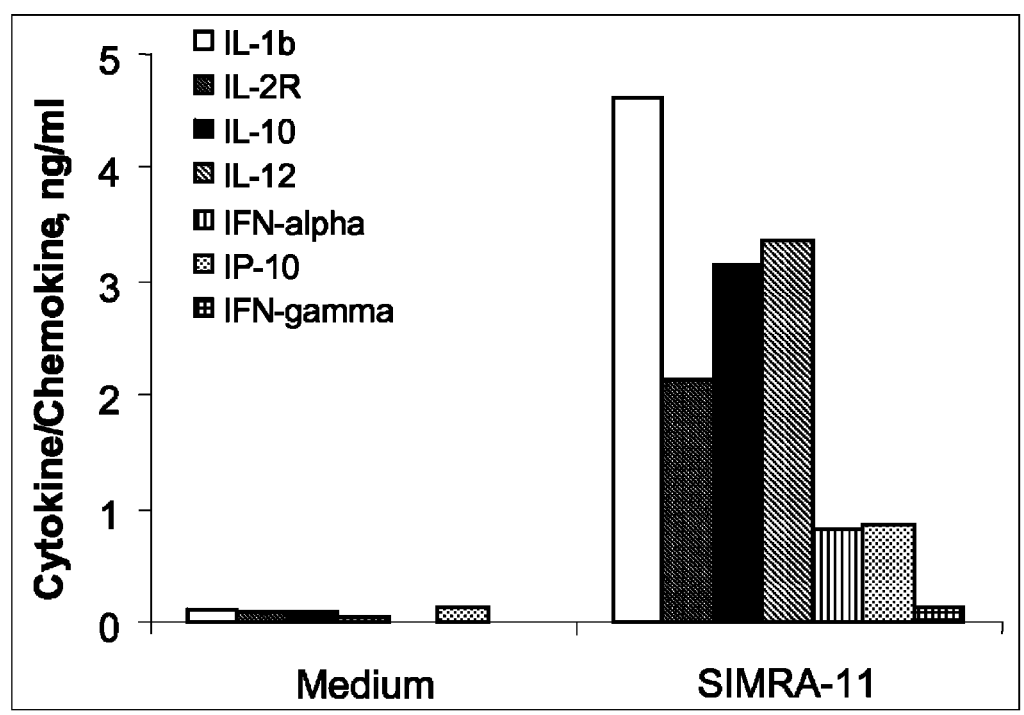
FIGS. 8A and 8B depict a cytokine/chemokine profile from human PBMCs treated with a SIMRA compound of the invention demonstrating that SIMRA compounds (e.g. Seq. ID 11) induce cytokine secretion in human PBMCs.
Figure 8:
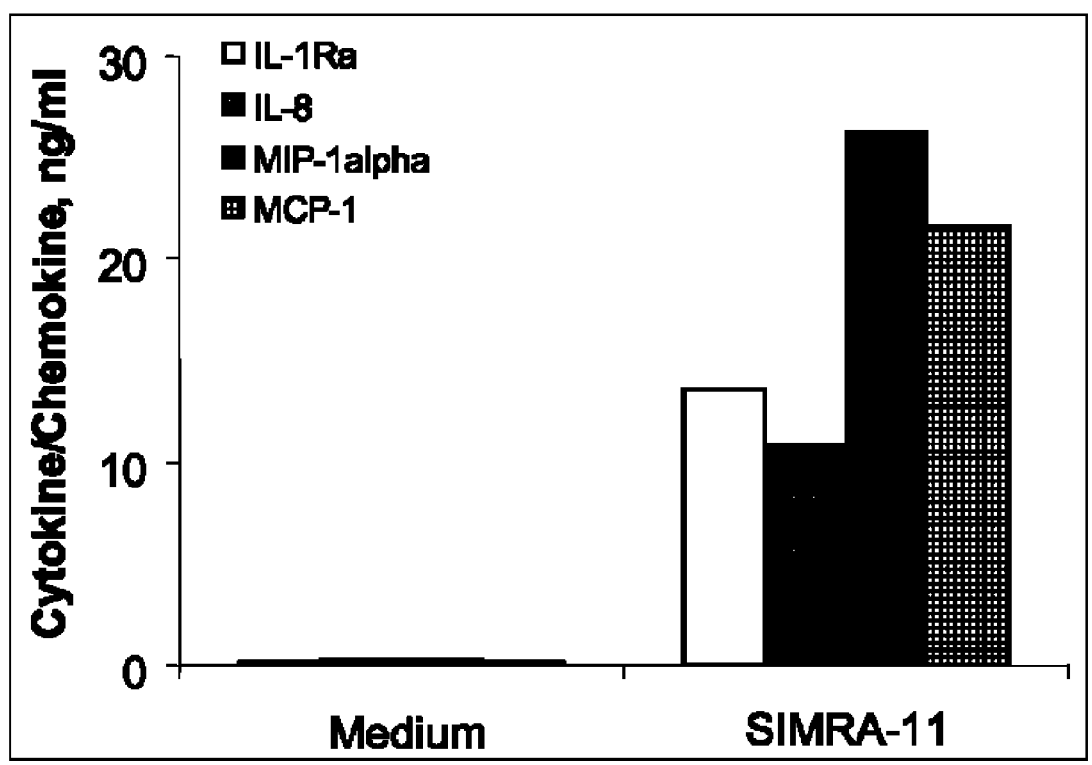

The immune modulatory oligoribonucleotides of the invention may conveniently be synthesized using an automated synthesizer and phosphoramidite approach as schematically depicted in FIGS. 1 and 2, and further described in the Examples. In some embodiments, the immune modulatory oligoribonucleotides are synthesized by a linear synthesis approach (see FIG. 1).

An alternative mode of synthesis is "parallel synthesis", in which synthesis proceeds outward from a central linker moiety (see FIG. 2). A solid support attached linker can be used for parallel synthesis, as is described in U.S. Pat. No. 5,912,332. Alternatively, a universal solid support (such as phosphate attached controlled pore glass) support can be used.

Parallel synthesis of immune modulatory oligoribonucleotides has several advantages over linear synthesis: (1) parallel synthesis permits the incorporation of identical monomeric units; (2) unlike in linear synthesis, both (or all) the monomeric units are synthesized at the same time, thereby the number of synthetic steps and the time required for the synthesis is the same as that of a monomeric unit; and (3) the reduction in synthetic steps improves purity and yield of the final immune modulatory oligoribonucleotide product.

At the end of the synthesis by either linear synthesis or parallel synthesis protocols, the immune modulatory oligoribonucleotides may conveniently be deprotected with concentrated ammonia solution or as recommended by the phosphoramidite supplier, if a modified nucleoside is incorporated. The product immune modulatory oligoribonucleotide is preferably purified by reversed phase HPLC, detritylated, desalted and dialyzed.

Table 3a shows non-limiting, representative RNA-based immune modulatory oligoribonucleotides according to the invention.

TABLE 3a

Examples of Stabilized RNA-based Immune Modulatory Oligonucleotide (SIMRA) Sequences

| SIMRA # | Sequences and Modification (SEQ ID NO:) |
|---|---|
| 1 | 5'-UGCUGCUUCUG-X-GUCUUCGUCGU-5' <br> (5'-SEQ ID NO: 1-3'-X-3'-SEQ ID NO: 1-5') |
| 2 | 5'-CUGUGCUUCUC-X-CUCUUCGUGUC-5' <br> (5'-SEQ ID NO: 2-3'-X-3'-SEQ ID NO: 2-5') |
| 3 | 5'-UCUGUGCUUCU-X-UCUUCGUGUCU-5' <br> (5'-SEQ ID NO: 3-3'-X-3'-SEQ ID NO: 3-5') |
| 4 | 5'-UICAAICUUIC-X-CIUUCIAACIU-5' <br> (5'-SEQ ID NO: 4-3'-X-3'-SEQ ID NO: 4-5') |
| 5 | 5'-GUGUGUGUG-X-GUGUGUGUG-5' <br> (5'-SEQ ID NO: 5-3'-X-3'-SEQ ID NO: 5-5') |
| 6 | 5'-UGCUGCUU-X-UUCGUCGU-5' <br> (5'-SEQ ID NO: 6-3'-X-3'-SEQ ID NO: 6-5') |
| 7 | 5'-UGCUGCUUCUGUGU-X-UGUGUCUUCGUCGU-5' <br> (5'-SEQ ID NO: 7-3'-X-3'-SEQ ID NO: 7-5') |

TABLE 3a-continued

Examples of Stabilized RNA-based Immune Modulatory Oligonucleotide (SIMRA) Sequences

| SIMRA # | Sequences and Modification (SEQ ID NO:) |
|---|---|
| 8 | 5'-UGCUGCUUCUGUGUCUG-X-GUCUGUGUCUUCGUCGU-5' <br> (5'-SEQ ID NO: 8-3'-X-3'-SEQ ID NO: 8-5') |
| 9 | 5'-$U_1$GCU$_1$GCU$_1$U$_1$CU$_1$G-X-GU$_1$CU$_1$U$_1$CGU$_1$CGU$_1$-5' <br> (5'-SEQ ID NO: 9-3'-X-3'-SEQ ID NO: 9-5') |
| 10 | 5'-$T_1$GCT$_1$GCT$_1$T$_1$CT$_1$G-X-GT$_1$CT$_1$T$_1$CGT$_1$CGT$_1$-5' <br> (5'-SEQ ID NO: 10-3'-X-3'-SEQ ID NO: 10-5') |
| 11 | 5'-UG$_1$CUG$_1$CUUCUG$_1$-X-G$_1$UCUUCG$_1$UCG$_1$U-5' <br> (5'-SEQ ID NO: 11-3'-X-3'-SEQ ID NO: 11-5') |
| 12 | 5'-G$_1$UCCUUCAACU-X-UCAACUUCCUG$_1$-5' <br> (5'-SEQ ID NO: 12-3'-X-3'-SEQ ID NO: 12-5') |
| 13 | 5'-GUCCUUCAACU-X-UCAACUUCCUG-5' <br> (5'-SEQ ID NO: 13-3'-X-3'-SEQ ID NO: 13-5') |
| 14 | 5'-UG$_1$CUG$_1$CUUCUG$_1$-X-G$_1$UCUUCG$_1$UCG$_1$U-5' <br> (5'-SEQ ID NO: 14-3'-X-3'-SEQ ID NO: 14-5') |
| 15 | 5'-G$_1$UCCUUCAACU-X-UCAACUUCCUG$_1$-5' <br> (5'-SEQ ID NO: 15-3'-X-3'-SEQ ID NO: 15-5') |
| 16 | 5'-OUCCUUCAACU-X-UCAACUUCCUO-5' <br> (5'-SEQ ID NO: 16-3'-X-3'-SEQ ID NO: 16-5') |
| 17 | 5'-UOCUOCUUCUO-X-OUCUUCOUCOU-5' <br> (5'-SEQ ID NO: 17-3'-X-3'-SEQ ID NO: 17-5') |
| 18 | 5'-UICUICUUCUI-X-IUCUUCIUCIU-5' <br> (5'-SEQ ID NO: 18-3'-X-3'-SEQ ID NO: 18-5') |
| 19 | 5'-IUCCUUCAACU-X-UCAACUUCCUI-5' <br> (5'-SEQ ID NO: 19-3'-X-3'-SEQ ID NO: 19-5') |
| 20 | 5'-$X_2$UGCUGCUUCUG-X-GUCUUCGUCG$U_X_2$-5' <br> (5'-$X_2$SEQ ID NO: 20-3'-X-3'-SEQ ID NO: 20$X_2$-5') |
| 21 | 5'-$X_2$UGCUGCUUCUG-X-GUCUUCGUCGU$X_2$-5' <br> (5'-$X_2$SEQ ID NO: 21-3'-X-3'-SEQ ID NO: 21$X_2$-5') |
| 22 | 5'-UGCUGCUUCUG-X-GUCUUCGUCGU-5' <br> (5'-SEQ ID NO: 22-3'-X-3'-SEQ ID NO: 22-5') |
| 23 | 5'-UGCUGCUUCUG-X-GUCUUCGUCGU-5' <br> (5'-SEQ ID NO: 23-3'-X-3'-SEQ ID NO: 23-5') |
| 24 | 5'-UGCUGCUUCUG-X-GUCUUCGUCGU-5' <br> (5'-SEQ ID NO: 24-3'-X-3'-SEQ ID NO: 24-5') |
| 25 | 5'-UGCUGCUACUG-X-GUCAUCGUCGU-5' <br> (5'-SEQ ID NO: 25-3'-X-3'-SEQ ID NO: 25-5') |
| 26 | 5'-UGCUGCUUGUG-X-GUGUUCGUCGU-5' <br> (5'-SEQ ID NO: 26-3'-X-3'-SEQ ID NO: 26-5') |
| 27 | 5'-UGCUGCUGCUG-X-GUCGUCGUCGU-5' <br> (5-SEQ ID NO: 27-3'-X-3'-SEQ ID NO: 27-5') |
| 28 | 5'-UGCUGCUUAUG-X-GUAUUCGUCGU-5' <br> (5'-SEQ ID NO: 28-3'-X-3'-SEQ ID NO: 28-5') |
| 29 | 5'-UG$_1$CUG$_1$CUUG$_1$UG$_1$-X-G$_1$UG$_1$UUCG$_1$UCG$_1$U-5' <br> (5'-SEQ ID NO: 29-3'-X-3'-SEQ ID NO: 29-5') |
| 30 | 5'-$X_2$UGCUGCUUGUG-X-GUGUUCGUCG$UX_2$-5 <br> (5'-$X_2$SEQ ID NO: 30-3'-X-3'-SEQ ID NO: 30$X_2$-5') |
| 31 | 5'-UGCUGCUUCUG-$X_1$-GUCUUCGUCGU-5' <br> (5'-SEQ ID NO: 31-3'-$X_1$-3'-SEQ ID NO: 31-5') |
| 32 | 5'-$X_7$UGCUGCUUGUG-X-GUGUUCGUCG$UX_7$-5' <br> (5'-$X_7$SEQ ID NO: 32-3'-X-3'-SEQ ID NO: 32$X_7$-5') |
| 33 | 5'-UGUUGUGUGAC-X-CAGUGUGUUGU-5' <br> (5'-SEQ ID NO: 33-3'-X-3'-SEQ ID NO: 33-5') |
| 34 | 5'-CUGGCGGCCUU-X-UUCCGGCGGUC-5' <br> (5'-SEQ ID NO: 34-3'-X-3'-SEQ ID NO: 34-5') |
| 35 | 5'-$X_3$UG$_1$CUG$_1$CUUGUG$_1$-X-G$_1$UGUUCG$_1$UCG$_1$U$X_3$-5' <br> (5'-$X_3$SEQ ID NO: 35-3'-X-3'-SEQ ID NO: 35$X_3$-5') |
| 36 | 5'-UGCUGCUUG$_2$UG-X-GUG$_2$UUCGUCGU-5' <br> (5'-SEQ ID NO: 36-3'-X-3'-SEQ ID NO: 36-5') |
| 37 | 5'-G$_2$GCUGCUUGUG-X-GUGUUCGUCGG$_2$-5' <br> (5'-SEQ ID NO: 37-3'-X-3'-SEQ ID NO: 37-5') |
| 38 | 5'-UGCUGCCUUUG-X-GUUUCCGUCGU-5' <br> (5'-SEQ ID NO: 38-3'-X-3'-SEQ ID NO: 38-5') |
| 39 | 5'-GUCCUUGCUUG-X-GUUCGUUCCUG-5' <br> (5'-SEQ ID NO: 39-3'-X-3'-SEQ ID NO: 39-5') |
| 40 | 5'-GUCCUUUGCUG-X-GUCGUUUCCUG-5' <br> (5'-SEQ ID NO: 40-3'-X-3'-SEQ ID NO: 40-5') |
| 41 | 5'-$X_3$UGCUGCUGCUG-X-GUCGUCGUCG$UX_3$-5' <br> (5'-$X_3$SEQ ID NO: 41-3'-X-3'-SEQ ID NO: 41$X_3$-5') |
| 42 | 5'-XUGCUGCUUGUG-X-GUGUUCGUCGUX-5' <br> (5'-XSEQ ID NO: 42-3'-X-3'-SEQ ID NO: 42X-5') |
| 43 | 5'-$X_7$UGCUGCUGCUG-X-GUCGUCGUCG$UX_7$-5' <br> (5'-$X_7$SEQ ID NO: 43-3'-X-3'-SEQ ID NO: 43$X_7$-5') |

TABLE 3a-continued

Examples of Stabilized RNA-based Immune Modulatory Oligonucleotide (SIMRA) Sequences

| SIMRA # | Sequences and Modification (SEQ ID NO:) |
|---|---|
| 44 | 5'-UUGCCCUUGCC-X-CCGUUCCCGUU-5' (5'-SEQ ID NO: 44-3'-X-3'-SEQ ID NO: 44-5') |
| 45 | 5'-UUGCUGUUGCU-X-UCGUUGUCGUU-5' (5'-SEQ ID NO: 45-3'-X-3'-SEQ ID NO: 45-5') |
| 46 | 5'-CUUUGGUGUGU-X-UGUGUGGUUUC-5' (5'-SEQ ID NO: 46-3'-X-3'-SEQ ID NO: 46-5') |
| 47 | 5'-UUGGUUGUUUG-X-GUUUGUUGGUU-5' (5'-SEQ ID NO: 47-3'-X-3'-SEQ ID NO: 47-5') |
| 48 | 5'-CUUUGGUGUGU-X-UGUGUGGUUUC-5' (5'-SEQ ID NO: 48-3'-X-3'-SEQ ID NO: 48-5') |
| 49 | 5'-$X_3$UUGGUUGUUUG-X-GUUUGUUGGUU$X_3$-5' (5'-$X_3$SEQ ID NO: 49-3'-X-3'-SEQ ID NO: 49$X_3$-5') |
| 50 | 5'-$X_3$GUCCUUGCUUG-X-GUUCGUUCCUG$X_3$-5' (5'-$X_3$SEQ ID NO: 50-3'-X-3'-SEQ ID NO: 50$X_3$-5') |
| 51 | 5'-PUGCUGCUUGUG-X-GUGUUCGUCGUP-5' (5'-SEQ ID NO: 51-3'-X-3'-SEQ ID NO: 51-5') |
| 52 | 5'-$X_4$UGCUGCUUGUG-X-GUGUUCGUCGU$X_4$-5' (5'-$X_4$SEQ ID NO: 52-3'-X-3'-SEQ ID NO: 52$X_4$-5') |
| 53 | 5'-$X_5$UGCUGCUUGUG-X-GUGUUCGUCGU$X_5$-5' (5'-$X_5$SEQ ID NO: 53-3'-X-3'-SEQ ID NO: 53$X_5$-5') |
| 54 | 5'-$X_6$UGCUGCUUGUG-X-GUGUUCGUCGU$X_6$-5' (5'-$X_6$SEQ ID NO: 54-3'-X-3'-SEQ ID NO: 54$X_6$-5') |
| 55 | 5'-U$G_1$CUG$_1$CUUCUG$_1$-$X_1$-$G_1$UCUUCG$_1$UCG$_1$U-5' (5'-SEQ ID NO: 55-3'-$X_1$-3'-SEQ ID NO: 55-5') |
| 56 | 5'-$X_3$UGCUGCUUGUG-$X_1$-GUGUUCGUCGU$X_3$-5' (5'-$X_3$SEQ ID NO: 56-3'-$X_1$-3'-SEQ ID NO: 56$X_3$-5') |
| 57 | 5'-U$G_3$CUGCUUCUG-X-GUCUUCGUCG$_3$U-5' (5'-SEQ ID NO: 57-3'-X-3'-SEQ ID NO: 57-5') |
| 58 | 5'-U$GG_4$UGCUUCUG-X-GUCUUCGUG$_4$GU-5' (5-SEQ ID NO: 58-3'-X-3'-SEQ ID NO: 58-5') |
| 59 | 5'-UU$G_1$$G_1$UU$G_1$UUUG$_1$-X-$G_1$UUUG$_1$UU$G_1$$G_1$UU-5' (5'-SEQ ID NO: 59-3'-X-3'-SEQ ID NO: 59-5') |
| 60 | 5'-U$G_1$CU$G_1$CCUUU $G_1$-X-$G_1$UUUCCG$_1$UCG$_1$U-5' (5'-SEQ ID NO: 60-3'-X-3'-SEQ ID NO: 60-5') |
| 61 | 5'-$G_1$UCCUUG$_1$CUU $G_1$-X-$G_1$UUCG$_1$UUCCU $G_1$-5' (5'-SEQ ID NO: 61-3'-X-3'-SEQ ID NO: 61-5') |
| 62 | 5'-$G_1$UCCUUUG$_1$CUG$_1$-X-$G_1$UCG$_1$UUUCCUG$_1$-5' (5'-SEQ ID NO: 62-3'-X-3'-SEQ ID NO: 62-5') |
| 63 | 5'-U$G_1$CUG$_1$CUUCU G$_1$-$X_8$-$G_1$UCUUCG$_1$UCG$_1$U-5' (5'-SEQ ID NO: 63-3'-$X_8$-3'-SEQ ID NO: 63-5') |
| 64 | 5'-CUG$_1$-X-$G_1$UC-5' (5'-SEQ ID NO: 64-3'-X-3'-SEQ ID NO: 64-5') |
| 65 | 5'-UU$G_1$CUG$_1$UUG$_1$CU-X-UCG$_1$UUG$_1$UCG$_1$UU-5' (5'-SEQ ID NO: 65-3'-X-3'-SEQ ID NO: 65-5') |
| 66 | 5'-U$G_1$CCUUG$_1$AACU-X-UCAAG$_1$UUCCG$_1$U-5' (5'-SEQ ID NO: 66-3'-X-3'-SEQ ID NO: 66-5') |
| 67 | 5'-UUCUG$_1$CUUCUG$_1$-X-$G_1$UCUUCG$_1$UCUU-5' (5'-SEQ ID NO: 67-3'-X-3'-SEQ ID NO: 67-5') |
| 68 | 5'-UUCUG$_1$CUUCUG$_1$-$X_5$-$G_1$UCUUCG$_1$UCUU-5' (5'-SEQ ID NO: 68-3'-$X_5$-3'-SEQ ID NO: 68-5') |
| 69 | 5'-$G_1$UCCUUCUCUG$_1$-X-$G_1$UCUCUUCCUG$_1$-5' (5'-SEQ ID NO: 69-3'-X-3'-SEQ ID NO: 69-5') |
| 70 | 5'-U$G_1$UURUG$_1$U$G_1$AC-X-CA$G_1$URU$G_1$UUG$_1$U-5' (5'-SEQ ID NO: 70-3'-X-3'-SEQ ID NO: 70-5') |
| 71 | 5'-$X_2$UUGGUUGUUG-X-GUUUGUUGGUU$X_2$-5' (5'-$X_2$SEQ ID NO: 71-3'-X-3'-SEQ ID NO: 71$X_2$-5') |
| 72 | 5'-$X_2$GUCCUUGCUUG-X-GUUCGUUCCUG$X_2$-5 (5'-$X_2$SEQ ID NO: 72-3'-X-3'-SEQ ID NO: 72$X_2$-5') |
| 73 | 5'-$X_6$UUGGUUGUUUG-X-GUUUGUUGGUU$X_6$-5' (5'-$X_6$SEQ ID NO: 73-3'-X-3'-SEQ ID NO: 73$X_6$-5') |
| 74 | 5'-$X_6$GUCCUUGCUUG-X-GUUCGUUCCUG$X_6$-5' (5'-$X_6$SEQ ID NO: 74-3'-X-3'-SEQ ID NO: 74$X_6$-5') |
| 75 | 5'-$X_2$UGCUGCUUGUG-$X_8$-GUGUUCGUCGU$X_2$-5' (5'-$X_2$SEQ ID NO: 75-3'-$X_8$-3'-SEQ ID NO: 75$X_2$-5') |
| 76 | 5'-UGCUGCUUCUGGACAUGUCCAG-3' (5'-SEQ ID NO: 76-3') |
| 77 | 5'-UGCUGCUUCUGUGAUAUCACAG-3' (5'-SEQ ID NO: 77-3') |
| 78 | 5'-UGCUGCUUCUGAAUUAAUUCAG-3' (5'-SEQ ID NO: 78-3') |
| 79 | 5'-UGCUGCUUCUGGACUAGUCCAG-3' (5'-SEQ ID NO: 79-3') |
| 80 | 5'-UGCUGCUUcugugauaucacag-3' (5'-SEQ ID NO: 80-3') |
| 81 | 5'-AGUUGAAGGACUGCUGCUUCUG-3' (5'-SEQ ID NO: 81-3') |
| 82 | 5'-GUCCUUCAACUCAGAAGCAGCA-3' (5'-SEQ ID NO: 82-3') |
| 83 | 5'-AGUUGAAGGAC$X_2$UGCUGCUUCUG-3' (5'-SEQ ID NO: 83-3'-$X_2$-5'-SEQ ID NO: 1-3') |
| 84 | 5'-GUCCUUCAACU$X_2$CAGAAGCAGCA-3' (5'-SEQ ID NO: 84-3'-$X_2$-5'-SEQ ID NO: 125-3') |
| 85 | 5'-CCCIIICCC$X_2$CCCIIICCC-3' (5'-SEQ ID NO: 85-3'-$X_2$-5'-SEQ ID NO: 85-3') |
| 86 | 5'-AGAAGCUUCUG-X-GUCUUCGAAGA-5' (5'-SEQ ID NO: 86-3'-X-3'-SEQ ID NO: 86-5') |
| 87 | 5'-UGAAGCUUCUG-X-GUCUUCGAAGU-5' (5'-SEQ ID NO: 87-3'-X-3'-SEQ ID NO: 87-5') |
| 88 | 5'-$X_6$UUGGUUGUUUG-X-GUUUGUUGGUU$X_6$-5' (5'-$X_6$SEQ ID NO: 88-3'-X-3'-SEQ ID NO: 88$X_6$-5') |
| 89 | 5'-$X_6$GUCCUUGCUUG-X-GUUCGUUCCUG$X_6$-5' (5'-$X_6$SEQ ID NO: 89-3'-X-3'-SEQ ID NO: 89$X_6$-5') |
| 90 | 5'-UCUGAAUUCAG-X-GACUUAAGUCU-5' (5'-SEQ ID NO: 90-3'-X-3'-SEQ ID NO: 90-5') |
| 91 | 5'-GUUUGCACAAC-X-CAACACGUUUG-5' (5'-SEQ ID NO: 91-3'-X-3'-SEQ ID NO: 91-5') |
| 92 | 5'-GCACACUUGUU-X-UUGUUCACACG-5' (5'-SEQ ID NO: 92-3'-X-3'-SEQ ID NO: 92-5') |
| 93 | 5'-CACUGUUGAGA-X-AGAGUUGUCAC-5' (5'-SEQ IN NO: 93-3'-X-3'-SEQ IN NO: 93-5') |
| 94 | 5'-CACUGUUGACA-X-ACAGUUGUCAC-5' (5'-SEQ ID NO: 94-3'-X-3'-SEQ ID NO: 94-5') |
| 95 | 5'-AACUGUUGACC-X-CCAGUUGUCAA-5' (5'-SEQ ID NO: 95-3'-X-3'-SEQ ID NO: 95-5') |
| 96 | 5'-CAACGACCUGU-X-UGUCCAGCAAC-5' (5'-SEQ ID NO: 96-3'-X-3'-SEQ ID NO: 96-5') |
| 97 | 5'-AGCACAACUGU-X-UGUCAACACGA-5' (5'-SEQ ID NO: 97-3'-X-3'-SEQ ID NO: 97-5') |
| 98 | 5'-UGCUGAGUGUU-X-UUGUGAGUCGU-5' (5'-SEQ ID NO: 98-3'-X-3'-SEQ ID NO: 98-5') |
| 99 | 5'-AGUGUUUUCUG-X-GUCUUUUGUGA-5' (5'-SEQ ID NO: 99-3'-X-3'-SEQ ID NO: 99-5') |
| 100 | 5'-UGCUGCUUCUG$X_2$UGCUGCUUCUG-3' (5'-SEQ ID NO: 100-3'-$X_2$-5'-SEQ ID NO: 100-3') |
| 101 | 5'-UGCUGCUUCUG$X_2$UGCUGAGUGUU-3' (5'-SEQ ID NO: 101-3'-$X_2$-5'-SEQ ID NO: 98-3') |
| 102 | 5'-AGUGUUUUCUG$X_2$UGCUGCUUCUG-3' (5'-SEQ ID NO: 102-3'-$X_2$-5'-SEQ ID NO: 100-3') |
| 103 | 5'-CAACGAACCCU-X-UCCCAAGCAAC-5' (5'-SEQ ID NO: 103-3'-X-3'-SEQ ID NO: 103-5') |
| 104 | 5'-$G_1$UCCUUG$_1$CUUG$_1$-$X_8$-$G_1$UUCG$_1$UUCCUG$_1$-5' (5'-SEQ ID NO: 104-3'-$X_8$-3'-SEQ ID NO: 104-5') |
| 105 | 5'-$G_1$UCCUUG$_1$CUUG$_1$-X-$G_1$UUCG$_1$UUCCUG$_1$-5' (5'-SEQ ID NO: 105-3'-X-3'-SEQ ID NO: 105-5') |
| 106 | 5'-UUCUG$_1$CUUCUG$_1$-$X_8$-$G_1$UCUUCG$_1$UCUU-5' (5-SEQ ID NO: 106-3'-$X_8$-3'-SEQ ID NO: 106-5') |
| 107 | 5'-UUCUG$_1$CUUCUG$_1$-X-$G_1$UCUUCG$_1$UCUU-5' (5'-SEQ ID NO: 107-3'-X-3'-SEQ ID NO: 107-5') |
| 108 | 5'-$X_2$UUCUG$_1$CUUCUG$_1$-X-$G_1$UCUUCG$_1$UCUU$X_2$-5' (5'-$X_2$SEQ ID NO: 108-3'-X-3'-SEQ ID NO: 108$X_2$-5') |
| 109 | 5'-$X_2$$G_1$UCCUUG$_1$CUUG$_1$-X-$G_1$UUCG$_1$UUCCUG$_1$$X_2$-5' (5'-$X_2$SEQ ID NO: 109-3'-X-3'-SEQ ID NO: 109$X_2$-5') |
| 110 | 5'-U$G_1$CUG$_1$CCUUUG$_1$-X-$G_1$UUUCCG$_1$UCG$_1$U-5' (5'-SEQ ID NO: 110-3'-X-3'-SEQ ID NO: 110-5') |
| 111 | 5'-U$G_1$CUG$_1$CCUUUG$_1$-$X_9$-$G_1$UUUCCG$_1$UCG$_1$U-5' (5-SEQ ID NO: 111-3'-$X_9$-3'-SEQ ID NO: 111-5') |
| 112 | 5'-$G_1$UCCUUUG$_1$CUG$_1$-X-$G_1$UCG$_1$UUUCCUG$_1$-5' (5'-SEQ ID NO: 112-3'-X-3'-SEQ ID NO: 112-5') |
| 113 | 5'-$G_1$UCCUUUG$_1$CUG$_1$-$X_9$-$G_1$UCG$_1$UUUCCUG$_1$-5' (5'-SEQ ID NO: 113-3'-$X_9$-3'-SEQ ID NO: 113-5') |
| 114 | 5'-$X_6$UGCUGCUUGUG-X-GUGUUCGUCGU$X_6$-5' (5'-$X_6$SEQ ID NO: 114-3'-X-3'-SEQ ID NO: 114$X_6$-5') |
| 115 | 5'-$X_5$GCUGCCUUUG-$X^9$-GUUUCCGUCGU$X_5$-5' (5'-$X_5$SEQ ID NO: 115-3'-$X_9$-3'-SEQ ID NO: 38$X_5$-5') |

TABLE 3a-continued

Examples of Stabilized RNA-based Immune Modulatory Oligonucleotide (SIMRA) Sequences

| SIMRA # | Sequences and Modification (SEQ ID NO:) |
|---|---|
| 116 | (5'UGCUGCUUGUG)$_2$-X-CCGUUGACAG-3' <br> (5'-SEQ ID NO: 116-3'-X-3'-SEQ ID NO: 116-5') ┌─(5'-SEQ ID NO: 126-3') |
| 117 | (5'-UGCUGCUUGUG)$_2$-X-ACACGCGUGU-3' <br> (5'-SEQ ID NO: 117-3'-X-3'-SEQ ID NO: 117-5') ┌─(5'-SEQ ID NO: 127-3') |
| 118 | 5'-CCCIIICCCII-X-IICCCIIICCC-5' <br> (5'-SEQ ID NO: 118-3'-X-3'-SEQ ID NO: 118-5') |
| 119 | 5'-TTTTTTTTTTTTTTT-X-(G$_1$UCUUCG$_1$UCG$_1$U)$_2$-5 <br> (5'-SEQ ID NO: 124-3'-X-3'-SEQ ID NO: 124-5') ┌─(3'-SEQ ID NO: 119-5') |
| 120 | 3'-TTTTTTTTTTTTTTT-X-(G$_1$UCUUCG$_1$UCG$_1$U)$_2$-5 <br> (5'-SEQ ID NO: 124-3'-X-3'-SEQ ID NO: 124-5') ┌─(5'-SEQ ID NO: 120-3') |
| 121 | 5'-U$_1$U$_1$U$_1$U$_1$U$_1$U$_1$U$_1$U$_1$U$_1$U$_1$U$_1$U$_1$U$_1$-X-(G$_1$UCUUCG$_1$UCG$_1$U)$_2$-5' <br> (5'-SEQ ID NO: 124-3'-X-3'-SEQ ID NO: 124-5') ┌─(3'-SEQ ID NO: 121-5') |
| 122 | 5'-CCIICCIICCC-X-CCCIICCIICC-5' <br> (5'-SEQ ID NO: 122-3'-X-3'-SEQ ID NO: 122-5') |
| 123 | 5'-CCIICCIICCX$_2$CCIICCIICC-3' <br> (5'-SEQ ID NO: 123-3'-X$_2$-3'-SEQ ID NO: 123-5') |

I = inosine;
U$_1$ = dU;
T$_1$ = riboT;
G$_1$ = 7-deaza-G;
G$_2$ = ara-G;
G$_3$ = 6-thio-G;
G$_4$ = 1(β-D-ribofuranosyl)-2-oxo-7-deaza-8-methyl-purine;
O = loxoribin;
X = glycerol;
X$_1$ = 1,3,5-pentanetriol;
X$_2$ = X$_3$ = C3 linker or propanediol;
X$_4$ = tri(ethyleneglycol);
X$_5$ = 1, 5 pentanediol;
X$_6$ = 2'-deoxy-abasic;
X$_7$ = C3 aminolinker;
X$_8$ = cis, cis-cyclohexanetriol;
X$_9$ = cis, trans-cyclohexanetriol; underlined = 2'-O-Me-ribonucleotides; P = phosphorothioate; lower case = phosphodiester backbone.

Table 3b shows non-limiting, representative secondary structures that may be formed by some of the oligoribonucleotides according to the invention.

TABLE 3b

Examples of structures that may be formed by some of the SIMRA compounds

| Sequence ID# | |
|---|---|
| 76 | 5'-UGCUGCUUCUGGACAUGUCCAG-3' <br> 3'-GACCUGUACAGGUCUUCGUCGU-5' |
| 77 | 5'-UGCUGCUUCUGUGAUAUCACAG-3' <br> 3'-GACACUAUAGUGUCUUCGUCGU-5' |
| 78 | 5'-UGCUGCUUCUGAAUUAAUUCAG-3' <br> 3'-GACUUAAUUAAGUCUUCGUCGU-5' |
| 79 | 5'-UGCUGCUUCUGGACUAGUCCAG-3' <br> 3'-GACCUGAUCAGGUCUUCGUCGU-5' |
| 80 | 5'-UGCUGCUUcugugauaucacag-3' <br> 3'-gacacuauagugucUUCGUCGU-5' |
| 81 + 82 | 5'-AGUUGAAGGACUGCUGCUUCUG-3' <br> 3'-ACGACGAAGACUCAACUUCCUG-5' |
| 83 + 84 | 5'-AGUUGAAGGACX$_2$UGCUGCUUCUG-3' <br> 3'-ACGACGAAGACX$_2$UCAACUUCCUG-5' |
| 85 | [5'-CCCIIICCCX$_2$CCCIIICCC-3'    5'-CCCIIICCCX$_2$CCCIIICCC-3' <br> 3'-CCIIICCCX$_2$CCCIIICCC-5']$_n$ |
| 86 | [5'-AGAAGCUUCUG-X-GUCUUCGAAGA-5' 5'-AGAAGCUUCUG-X-GUCUUCGAAGA-5' <br> 5'-AGAAGCUUCUG-X-GUCUUCGAAGA-5']$_n$ |
| 87 | [5'-UGAAGCUUCUG-X-GUCUUCGAAGU-5' 5'-UGAAGCUUCUG-X-GUCUUCGAAGU-5' <br> 5'-UGAAGCUUCUG-X-GUCUUCGAAGU-5']$_n$ |

TABLE 3b-continued

Examples of structures that may be formed by some of the SIMRA compounds

| Sequence ID# | |
|---|---|
| 127 | (5'-UGCUGCUUGUG)$_2$-X-ACACGCGUGU-3'<br>3'-UGUGCGCACA-X-(GUGUUCGUCGU-5')$_2$ |
| 118 | [5'-CCCIIICCCII-X-IICCCIIICCC-5'  5'-CCCIIICCCII-X-IICCCIIICCC-5'<br>5'-CCCIIICCCII-----X---- IICCCIIICCC-5'] |
| 122 | [5'-CCIICCIICCC-X-CCCIICCIICC-5'  5'-CCIICCIICCC-X-CCCIICCIICC-5'<br>5'-CCIICCIICCC-X-CCCIICCIICC-5'] |
| 123 | 5'-CCIICCIICCX$_2$CCIICCIICC-3'<br>3'-CCIICCIICCX$_2$CCIICCIICC-5' |

In a second aspect, the invention provides pharmaceutical formulations comprising a SIMRA compound according to the invention and a physiologically acceptable carrier.

In a third aspect, the invention provides methods for generating a TLR7 and/or TLR8 mediated immune response in a vertebrate, such methods comprising administering to the vertebrate a SIMRA compound according to the invention. In some embodiments, the vertebrate is a mammal. In preferred embodiments, SIMRA compound is administered to a vertebrate in need of immune stimulation.

In a fourth aspect, the invention provides methods for therapeutically treating a patient having a disease or disorder, such methods comprising administering to the patient a SIMRA compound according to the invention. In various embodiments, the disease or disorder to be treated is cancer, an autoimmune disorder, infectious disease, airway inflammation, inflammatory disorders, allergy, asthma, or a disease caused by a pathogen. Pathogens include bacteria, parasites, fungi, viruses, viroids, and prions.

In a fifth aspect, the invention provides methods for preventing a disease or disorder, such methods comprising administering to the patient SIMRA compound according to the invention. In various embodiments, the disease or disorder to be prevented is cancer, an autoimmune disorder, airway inflammation, inflammatory disorders, infectious disease, allergy, asthma, or a disease caused by a pathogen. Pathogens include bacteria, parasites, fungi, viruses, viroids, and prions.

In a sixth aspect the invention provides a method of preventing or treating a disorder, such methods comprises isolating cells capable of producing cytokines or chemokines including, but not limited to, immune cells, T-regulatory cells, B-cells, PBMCs, pDCs and lymphoid cells; culturing such cells under standard cell culture conditions, treating such cells ex vivo with a SIMRA such that the isolated cells produce or secrete increased levels of cytokines or chemokines, and administering or re-administering the treated cells to a patient in need of cytokine or chemokine therapy for the prevention or treatment of disease. This aspect of the invention would be in accordance with standard adoptive cellular immunotherapy techniques to produce activated immune cells.

In some embodiments of this aspect of the invention, the cells capable of producing cytokines or chemokines may be isolated from subjects with or without a disease or disorder. Such isolation may include identification and selection and could be performed using standard cell isolation procedures, including those set forth in the specific examples below. Such isolated cells would be cultured according to standard cell culturing procedures and using standard cell culture conditions, which may include the culturing procedures and conditions set forth in the specific examples below. In a further aspect of this embodiment of the invention, the isolated cells would be cultured in the presence of at least one SIMRA, in an amount and for a time period sufficient to induce, increase or enhance the production and/or secretion of cytokines and/or chemokines as compared to the isolated cells cultured in the absence of such one or more SIMRA. Such time may be from minutes, to hours, to days. Such isolated, SIMRA-treated cells may find use following re-administration to the donor or administration to a second patient, wherein such donor or second patient are in need of induced, increased or enhanced production and/or secretion of cytokines and/or chemokines. For example, re-administration to a donor or administration to a second patient having cancer, an autoimmune disorder, airway inflammation, inflammatory disorders, infectious disease, allergy, asthma, or a disease caused by a pathogen. Such re-administration or administration may be accomplished using various modes, including catheter or injection administration or any other effective route. This aspect of the invention may also find use in patients who may have a limited or incomplete ability to mount an immune response or are immune compromised (e.g. patient infected with HIV and bone marrow transplant patients).

In any of the methods according to the invention, the SIMRA compound can variously act by producing direct immune modulatory effects alone and/or in combination with any other agent useful for treating or preventing the disease or condition that does not diminish the immune modulatory effect of the SIMRA compound. In any of the methods according to the invention, the agent(s) useful for treating or preventing the disease or condition includes, but is not limited to, vaccines, antigens, antibodies, preferably monoclonal antibodies, cytotoxic agents, allergens, antibiotics, siRNA, antisense oligonucleotides, TLR agonist (e.g. agonists of TLR9 and/or agonists of TLR3), chemotherapeutic agents (both traditional chemotherapy and modern targeted therapies), targeted therapeutic agents, activated cells, peptides, proteins, gene therapy vectors, peptide vaccines, protein vaccines, DNA vaccines, adjuvants, and co-stimulatory molecules (e.g. cytokines, chemokines, protein ligands, transactivating factors, peptides or peptides comprising modified amino acids), or combinations thereof. For example, in the treatment of cancer, it is contemplated that the SIMRA compound may be administered in combination with one or more chemotherapeutic compound, targeted therapeutic agent and/or monoclonal antibody. Alternatively, the agent can include DNA vectors encoding for antigen or allergen. Alternatively, the SIMRA compounds can be administered in combination with other adjuvants to enhance the specificity or magnitude of the immune response to the SIMRA compound.

In any of the methods according to the invention, administration of SIMRA compound, alone or in combination with any other agent, can be by any suitable route, including, without limitation, parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form. Administration of the therapeutic compositions of SIMRA compound can be carried out using known procedures using an effective amount and for periods of time effective to reduce symptoms or surrogate markers of the disease. For example, an effective amount of a SIMRA compound for treating a disease and/or disorder could be that amount necessary to alleviate or reduce the symptoms, or delay or ameliorate a tumor, cancer, or bacterial, viral or fungal infection. An effective amount for use as a vaccine adjuvant could be that amount useful for boosting a subject's immune response to a vaccine or antigen. In the context of administering a composition that modulates an immune response to a co-administered antigen, an effective amount of a SIMRA compound and antigen is an amount sufficient to achieve the desired modulation as compared to the immune response obtained when the antigen is administered alone. The effective amount for any particular application can vary depending on such factors as the disease or condition being treated, the particular oligonucleotide being administered, the size of the subject, or the severity of the disease or condition. One of ordinary skill in the art can empirically determine the effective amount of a particular oligonucleotide without necessitating undue experimentation.

When administered systemically, the therapeutic composition is preferably administered at a sufficient dosage to attain a blood level of SIMRA compound from about 0.0001 micromolar to about 10 micromolar. For localized administration, much lower concentrations than this may be effective, and much higher concentrations may be tolerated. Preferably, a total dosage of SIMRA compound ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

The SIMRA compound may optionally be linked to one or more allergens and/or antigens (self or foreign), an immunogenic protein, such as keyhole limpet hemocyanin (KLH), cholera toxin B subunit, or any other immunogenic carrier protein. SIMRA can also be used in combination with other compounds (e.g. adjuvants) including, without limitation, TLR agonists (e.g. TLR2 agonists and TLR9 agonists), Freund's incomplete adjuvant, KLH, monophosphoryl lipid A (MPL), alum, and saponins, including QS-21 and imiquimod, or combinations thereof.

The methods according to this aspect of the invention are useful for model studies of the immune system. The methods are also useful for the prophylactic or therapeutic treatment of human or animal disease. For example, the methods are useful for pediatric and veterinary vaccine applications.

The examples below are intended to further illustrate certain preferred embodiments of the invention, and are not intended to limit the scope of the invention.

EXAMPLES

Immune Modulatory Oligoribonucleotide Synthesis

The immune modulatory oligoribonucleotides were chemically synthesized using phosphoramidite chemistry on automated DNA/RNA synthesizer. TAC protected (Except U) 2'-O-TBDMS RNA monomers, A, G, C and U, were purchased from Sigma-Aldrich. 7-deaza-G, inosine and loxoribine monomers were purchased from ChemGenes Corporation. 0.25M 5-ethylthio-1H-tetrazole, PAC-anhydride Cap A and Cap B were purchased from Glen Research. 3% trichloroacetic acid (TCA) in dichloromethane (DCM) and 5% 3H-1,2-Benzodithiole-3-one-1,1-dioxide (Beaucage reagent) were made in house.

Immune modulatory oligoribonucleotides were synthesized at 1-2 μM scale using a standard RNA synthesis protocol.

Cleavage and Base Deprotection

Immune modulatory oligoribonucleotides were cleaved from solid support and the solution was further heated at 65° C. to removing protecting groups of exo cyclic-amines. The resulting solution was dried completely in a SpeedVac.

IE HPLC Purification

Immune modulatory oligoribonucleotides were purified by ion exchange HPLC.
Column: Dionex DNAPac 100 column (22X250)
Column Heater ChromTech TL-105 HPLC column heater, temperature is set to 80° C.
Buffer A: 20 mM Tris-HCl, pH 7.0, 20% acetonitrile
Buffer B: 3.0 M NaCl, 20 mM Tris-HCl, pH 7.0, 20% acetonitrile
Flow rate: 10 ml/min
Gradient:
    0-2 min: 0% B
    2-11 min: 0% B to 35% B
    11-41 min: 35% B to 90% B
    41-45 min: 100% B Crude immune modulatory oligoribonucleotide solution was injected into HPLC. Above gradient is performed and the fractions were collected. All fractions containing more than 90% desired product were mixed, and then the solution was concentrated to almost dry by RotoVap. RNAse-free water was added to make final volume of 10 ml.

C-18 Reversed Phase Desalting

CC-18 Sep-Pak cartridge purchased from Waters was first conditioned with 10 ml of acetonitrile followed by 10 ml of 0.5 M sodium acetate. 10 ml of immune modulatory oligoribonucleotide solution was loaded. 15 ml of water was then used to wash out the salt. The immune modulatory oligoribonucleotide was finally eluted out by 1 ml of 50% acetonitrile in water.

The solution is placed in SpeedVac for 30 minutes. The remaining solution was filter through a 0.2 micro filter and then was lyophilized to dryness. The solid was then re-dissolved in water to make the desired concentration.

The final solution was stored below 0° C.

Capillary Electrophoresis
    Instrument: Beckman 5010
    Capillary: 62 cm ssDNA capillary
    Sample preparation: 0.2 OD of SIMRA compound was dissolved in 200 ul of RNAse-free water.
    Injection: electro-kinetic injection at 5 KV for 5 seconds.
    Running condition: 14 KV for 50 minutes at 30° C.

Ion Exchange HPLC Analysis
    Column: Dionex DNAPac guard column (22×250)
    Column Heater ChromTech TL-105 HPLC column heater, temperature is set to 80° C.
    Buffer A: 100 mM Tris-HCl, pH 8.0, 20% acetonitrile
    Buffer B: 2.0 M LiCl, 100 mM Tris-HCl, pH 8.0, 20% acetonitrile
    Flow rate: 2 ml/min Gradient:
  0-2 min: 0% B
  2-10 min: 0% B to 100% B
  10-15 min: 100% B PAGE Analysis 0.3 OD of immune modulatory oligoribonucleotide was loaded on 20% polyacrylamide gel and was running at constant power of 4 watts for approximately 5 hours. The gel was viewed under short wavelength UV light.

Human Cell Culture Protocols

Human PBMC Isolation

Peripheral blood mononuclear cells (PBMCs) from freshly drawn, healthy volunteer blood (CBR Laboratories, Boston, Mass.) were isolated by Ficoll density gradient centrifugation method (Histopaque-1077, Sigma).

Human pDC Isolation

Peripheral blood mononuclear cells (PBMCs) from freshly drawn healthy volunteer blood (CBR Laboratories, Boston, Mass.) were isolated by Ficoll density gradient centrifugation method (Histopaque-1077, Sigma). pDCs were isolated from PBMCs by positive selection using the BDCA4 cell isolation kits (Miltenyi Biotec) according to the manufacturer's instructions.

Cytokine ELISAs

Human PBMCs were plated in 48-well plates using $5 \times 10^6$ cells/ml. pDCs were plated in 96-well dishes using $1 \times 10^6$ cells/ml. The SIMRAs dissolved in DPBS (pH 7.4; Mediatech) were added to a final concentration of 100.0 μg/ml to the cell cultures. The cells were then incubated at 37° C. for 24 hr and the supernatants were collected for luminex multiplex or ELISA assays. The experiments were performed in triplicate wells. The levels of IFN-α, IL-6, or TNF-α were measured by sandwich ELISA. The required reagents, including cytokine antibodies and standards, were purchased from PharMingen.

Luminex multiplex assays were performed using Biosource human multiplex cytokine assay kits on Luminex 100 instrument and the data were analyzed using StarStation software supplied by Applied Cytometry Systems (Sacramento, Calif.).

Protocols for Assays with HEK293 Cells Expressing TLRs

HEK293/human TLR7 or HEK293/human TLR8 cells (Invivogen, San Diego, Calif.) were cultured in 48-well plates in 250 μl/well DMEM supplemented with 10% heat-inactivated FBS in a 5% $CO_2$ incubator.

Reporter Gene Transformation

HEK293 cells stably expressing mouse TLR9 or human TLR3, 7 or 8 (Invivogen, San Diego, Calif.) were cultured in 48-well plates in 250 μl/well DMEM supplemented with 10% heat-inactivated FBS in a 5% $CO_2$ incubator. At 80% confluence, cultures were transiently transfected with 400 ng/ml of SEAP (secreted form of human embryonic alkaline phosphatase) reporter plasmid (pNifty2-Seap) (Invivogen) in the presence of 4 μl/ml of lipofectamine (Invitrogen, Carlsbad, Calif.) in culture medium. Plasmid DNA and lipofectamine were diluted separately in serum-free medium and incubated at room temperature for 5 minutes. After incubation, the diluted DNA and lipofectamine were mixed and the mixtures were incubated at room temperature for 20 minutes. Aliquots of 25 μl of the DNA/lipofectamine mixture containing 100 ng of plasmid DNA and 1 μl of lipofectamine were added to each well of the cell culture plate, and the cultures were continued for 4 hours.

IMO-Treatment

After transfection, medium was replaced with fresh culture medium, SIMRAs were added to the cultures, and the cultures were continued for 18 hours. At the end of SIMRA treatment, 30 μl of culture supernatant was taken from each treatment and used for SEAP assay following manufacturer's protocol (Invivogen).

SEAP Assay

Briefly, culture supernatants were incubated with p-nitrophenyl phosphate substrate and the yellow color generated was measured by a plate reader at 405 nm. The data are shown as fold increase in NF-κB activity over PBS control. (Putta M R et al, Nucleic Acids Res., 2006, 34:3231-8)

| Fold change in NF-kB activity of HEK293 cells expressing human TLR8 SEQ ID NO: | | |
|---|---|---|
| No | Sequence | at 14.3 μM |
| PBS | | 1 |
| 1 | 5'-UGCUGCUUCUG-X-GUCUUCGUCGU-5' | 3.1 |
| 11 | 5'-UG₁CUG₁CUUCUG₁-X-G₁UCUUCG₁UCG₁U-5' | 4.8 |
| 12 | 5'-G₁UCCUUCAACU-X-UCAACUUCCUG₁-5' | 2.6 |
| 13 | 5'-GUCCUUCAACU-X-UCAACUUCCUG-5' | 4.3 |

| Fold change in NF-kB activity of HEK293 cells expressing human TLR8 SEQ ID NO: | | | |
|---|---|---|---|
| No | Sequence | at 14.3 | and 28.6 μM |
| PBS | | 1 | 1 |
| 1 | 5'-UGCUGCUUCUG-X-GUCUUCGUCGU-5' | 2.7 | 8 |
| 20 | 5'-X₂UGCUGCUUCUG-X-GUCUUCGUCGUX₂-5' | 3.12 | 8.5 |
| 21 | 5'-X₂UGCUGCUUCUG-X-GUCUUCGUCGUX₂-5' | 8.1 | 14.7 |
| 22 | 5'-UGCUGCUUCUG-X-GUCUUCGUCGU-5' | 0.6 | 1 |
| R848 | | 8.5 | |

-continued

| Fold change in NF-kB activity of HEK293 cells expressing human TLR8 SEQ ID NO: | | | |
|---|---|---|---|
| No | Sequence | at 14.3 and 28.6 µM | |
| PBS | | 1 | 1 |
| 1 | 5'-UGCUGCUUCUG-X-GUCUUCGUCGU-5' | 9.2 | 64.5 |
| 23 | 5'-UGCUGCUU̲CUG-X-GUC̲UUCGUCGU-5' | 1 | 4.1 |
| 24 | 5'-UGCUGCUUC̲UG-X-GUC̲UUCGUCGU-5' | 6.7 | 33.6 |
| 25 | 5'-UGCUGCUACUG-X-GUCAUCGUCGU-5' | 7.6 | 32.9 |
| 26 | 5'-UGCUGCUUGUG-X-GUGUUCGUCGU-5' | 1.9 | 15.63 |

| Fold change in NF-kB activity of HEK293 cells expressing human TLR8 SEQ ID NO: | | | |
|---|---|---|---|
| No | Sequence | at 14.3 and 28.6 µM | |
| PBS | | 1 | 1 |
| 1 | 5'-UGCUGCUUCUG-X-GUCUUCGUCGU-5' | 4.13 | 14.5 |
| 21 | 5'-X$_2$UGCUGCUUCUG-X-GUCUUCGUCGUX$_2$-5' | 8.6 | 22.9 |
| 24 | 5'-UGCUGCUUC̲UG-X-GUC̲UUCGUCGU-5' | 12.7 | 27.3 |
| 26 | 5'-UGCUGCUUGUG-X-GUGUUCGUCGU-5' | 4.8 | 19 |
| 27 | 5'-UGCUGCUGCUG-X-GUCGUCGUCGU-5' | 2.8 | 12.4 |
| 28 | 5'-UGCUGCUUAUG-X-GUAUUCGUCGU-5' | 2.2 | 5 |
| 30 | 5'-X$_2$UGCUGCUUG̲UG-X-GUG̲UUCGUCGUX$_2$-5' | 17.9 | 27.9 |
| R848 | | 12.5 | |

| Fold change in NF-kB activity of HEK293 cells expressing human TLR8 SEQ ID NO: | | |
|---|---|---|
| No | Sequence | at 14.3 µM |
| PBS | | 1 |
| 1 | 5'-UGCUGCUUCUG-X-GUCUUCGUCGU-5' | 3.1 |
| 11 | 5'-UG$_1$CUG$_1$CUUCUG$_1$-X-G$_1$UCUUCG$_1$UCG$_1$U-5' | 4.8 |
| 12 | 5'-G$_1$UCCUUCAACU-X-UCAACUUCCUG$_1$-5' | 2.6 |
| 13 | 5'-GUCCUUCAACU-X-UCAACUUCCUG-5' | 4.3 |

| Fold change in NF-kB activity of HEK293 cells expressing human TLR8 SEQ ID NO: | | |
|---|---|---|
| No | Sequence | at 14.3 µM |
| PBS | | 1 |
| 31 | 5'-UGCUGCUUCUG-X$_1$-GUCUUCGUCGU-5' | 4.2 |
| 32 | 5'-X$_7$UGCUGCUUGUG-X-GUGUUCGUCGUX$_7$-5' | 4.5 |
| 33 | 5'-UGUUGUGUGAC-X-CAGUGUGUUGU-5' | 7.0 |
| 34 | 5'-CUGGCGGCCUU-X-UUCCGGCGGUC-5' | 5.85 |
| 35 | 5'-X$_3$UG$_1$CUG$_1$CUUGUG$_1$-X-G$_1$UGUUCG$_1$UCG$_1$UX$_3$-5' | 9.2 |
| 36 | 5'-UGCUGCUUG$_2$UG-X-GUG$_2$UUCGUCGU-5' | 4.74 |
| 37 | 5'-G$_2$GCUGCUUGUG-X-GUGUUCGUCGG$_2$-5' | 4.4 |
| 38 | 5'-UGCUGCCUUG-X-GUUUCCGUCGU-5' | 7.5 |
| 39 | 5'-GUCCUUGCUUG-X-GUUCGUUCCUG-5' | 8.7 |

-continued

| No | Sequence | |
|---|---|---|
| 40 | 5'-GUCCUUUGCUG-X-GUCGUUUCCUG-5' | 8.1 |

Fold change in NF-kB activity of HEK293 cells expressing human TLR8 SEQ ID NO:

| No | Sequence | at 21.5 µM |
|---|---|---|
| PBS | | 1 |
| 41 | 5'-$X_3$UGCUGCUGCUG-X-GUCGUCGUCGU$X_3$-5' | 13.7 |
| 42 | 5'-XUGCUGCUUGUG-X-GUGUUCGUCGUX-5' | 16.0 |
| 43 | 5'-$X_7$UGCUGCUGCUG-X-GUCGUCGUCGU$X_7$-5' | 15.2 |
| 44 | 5'-UUGCCCUUGCC-X-CCGUUCCCGUU-5' | 10.5 |
| 45 | 5'-UUGCUGUUGCU-X-UCGUUGUCGUU-5' | 12.9 |
| 46 | 5'-CUUUGGUGUGU-X-UGUGUGGUUUC-5' | 5.1 |
| 47 | 5'-UUGGUUGUUUG-X-GUUUGUUGGUU-5' | 17.4 |
| 48 | 5'-CUUUGGUGUGU-X-UGUGUGGUUUC-5' | 5.1 |
| 55 | 5'-UG$_1$CUG$_1$CUUCUG$_1$-$X_1$-G$_1$UCUUCG$_1$UCG$_1$U-5' | 2.96 |
| 56 | 5'-$X_3$UGCUGCUUGUG-$X_1$-GUGUUCGUCGU$X_3$-5' | 9.14 |

Fold change in NF-kB activity of HEK293 cells expressing human TLR8 SEQ ID NO:

| No | Sequence | at 14.3 µM |
|---|---|---|
| PBS | | 1 |
| 57 | 5'-UG$_3$CUGCUUCUG-X-GUCUUCGUG$_3$U-5' | 9.16 |
| 58 | 5'-UGG$_4$UGCUUCUG-X-GUCUUCGUG$_4$GU-5' | 2.29 |

Fold change in NF-κB activity of HEK293 cells expressing human TLR8 SEQ ID NO:

| No. | Sequence | at 14.3 µM |
|---|---|---|
| PBS | | 1 |
| 86 | 5'-AGAAGCUUCUG-X-GUCUUCGAAGA-5' | 1.42 |
| 87 | 5'-UGAAGCUUCUG-X-GUCUUCGAAGU-5' | 1.54 |

Fold change in NF-κB activity of HEK293 cells expressing human TLR8 SEQ ID NO:

| No | Sequence | at 21.5 µM |
|---|---|---|
| PBS | | 1.0 |
| 90 | 5'-UCUGAAUUCAG-X-GACUUAAGUCU-5' | 9.7 |
| 92 | 5'-GCACACUUGUU-X-UUGUUCACACG-5' | 6.1 |
| 93 | 5'-CACUGUUGAGA-X-AGAGUUGUCAC-5' | 7.0 |
| 95 | 5'-AACUGUUGACC-X-CCAGUUGUCAA-5' | 8.1 |
| 96 | 5'-CAACGACCUGU-X-UGUCCAGCAAC-5' | 4.8 |
| 104 | 5'-G$_1$UCCUUG$_1$CUUG$_1$-$X_8$-G$_1$UUCG$_1$UUCCUG$_1$-5' | 2.8 |
| 105 | 5'-G$_1$UCCUUG$_1$CUUG$_1$-X-G$_1$UUCG$_1$UUCCUG$_1$-5' | 3.6 |
| 106 | 5'-UUCUG$_1$CUUCUG$_1$-$X_8$-G$_1$UCUUCG$_1$UCUU-5' | 3.8 |
| 107 | 5'-UUCUG$_1$CUUCUG$_1$-X-G$_1$UCUUCG$_1$UCUU-5' | 4.5 |
| 108 | 5'-$X_2$UUCUG$_1$CUUCUG$_1$-X-G$_1$UCUUCG$_1$UCUU$X_2$-5' | 3.6 |
| 109 | 5'-$X_2$G$_1$UCCUUG$_1$CUUG$_1$-X-G$_1$UUCG$_1$UUCCUG$_1$$X_2$-5' | 8.8 |

-continued

| | | |
|---|---|---|
| 110 | 5'-U$G_1$CU$G_1$CCUUU$G_1$-X-$G_1$UUUCC$G_1$UC$G_1$U-5' | 2.6 |
| 111 | 5'-U$G_1$CU$G_1$CCUUU$G_1$-$X_9$-$G_1$UUUCC$G_1$UC$G_1$U-5' | 2.5 |
| 112 | 5'-$G_1$UCCUUU$G_1$CU$G_1$-X-$G_1$UC$G_1$UUUCCU$G_1$-5' | 3.1 |
| 113 | 5'-$G_1$UCCUUU$G_1$CU$G_1$-$X_9$-$G_1$UC$G_1$UUUCCU$G_1$-5' | 2.5 |
| 114 | 5'-$X_6$UGCUGCUUGUG-X-GUGUUCGUCGU$X_6$-5' | 10.7 |
| 115 | 5'-$X_5$GCUGCCUUUG-$X_9$-GUUUCCGUCGU$X_5$-5' | 6.1 |
| 116/126 | (5'-UGCUGCUUGUG)$_2$-X-CCGUUGACAG-3' | 10.6 |
| 117/127 | (5'-UGCUGCUUGUG)$_2$-X-ACACGCGUGU-3' | 6.3 |
| 118 | 5'-CCCIIICCCII-X-IICCCIIICCC-5' | 1.3 |

Fold change in NF-kB activity of HEK293 cells expressing human TLR7 SEQ ID NO:

| No | Sequence | at 14.3 µM |
|---|---|---|
| PBS | | 1 |
| 1 | 5'-UGCUGCUUCUG-X-GUCUUCGUCGU-5' | 1.1 |
| 11 | 5'-U$G_1$CU$G_1$CUUCU$G_1$-X-$G_1$UCUUC$G_1$UC$G_1$U-5' | 9.3 |
| 12 | 5'-$G_1$UCCUUCAACU-X-UCAACUUCCU$G_1$-5' | 11.5 |
| 13 | 5'-GUCCUUCAACU-X-UCAACUUCCUG-5' | 1.8 |
| Loxoribine (465 µM) | | 7.26 |
| R848 | | 11.5 |

Fold change in NF-κB activity of HEK293 cells expressing human TLR7 SEQ ID NO:

| No | Sequence | at 14.3 µM |
|---|---|---|
| PBS | | 1 |
| 59 | 5'-UU$G_1G_1$UU$G_1$UUU$G_1$-X-$G_1$UUU$G_1$UU$G_1G_1$UU-5' | 2.311 |
| 60 | 5'-U$G_1$CU $G_1$CCUUU$G_1$-X-$G_1$UUUCC$G_1$UC$G_1$U-5' | 3.160 |
| 61 | 5'-$G_1$UCCUU$G_1$CUU$G_1$-X-$G_1$UUC$G_1$UUCCU$G_1$-5' | 2.603 |
| 62 | 5'-$G_1$UCCUUU$G_1$CU$G_1$-X-$G_1$UC$G_1$UUUCCU$G_1$-5' | 2.274 |
| 63 | 5'-U$G_1$CU$G_1$CUUCU $G_1$-$X_8$- $G_1$UCUUC$G_1$UC$G_1$U-5' | 2.887 |
| 64 | 5'-CU$G_1$-X- $G_1$UC-5' | 2.104 |
| 65 | 5'-UU$G_1$CU$G_1$UU$G_1$CU-X-UC$G_1$UU$G_1$UC$G_1$UU-5' | 1.454 |
| 66 | 5'-U$G_1$CCUU$G_1$AACU-X-UCAA$G_1$UUCC$G_1$U-5' | 1.411 |
| 67 | 5'-UUCU$G_1$CUUCU$G_1$-X-$G_1$UCUUC$G_1$UCUU-5' | 2.330 |
| 69 | 5'-$G_1$UCCUUCUCU$G_1$-X-$G_1$UCUCUUCCU$G_1$-5' | 2.377 |

IFN-α (pg/ml) in human PBMC assay as determined by ELISA SEQ ID NO:

| No | Sequence | at 21.5 µM |
|---|---|---|
| PBS | | 0 |
| 61 | 5'-$G_1$UCCUU$G_1$CUU$G_1$-X-$G_1$UUC$G_1$UUCCU$G_1$-5' | 1092.2 |
| 62 | 5'-$G_1$UCCUUU$G_1$CU$G_1$-X-$G_1$UC$G_1$UUUCCU$G_1$-5' | 491.4 |
| 63 | 5'-U$G_1$CU$G_1$CUUCU$G_1$-$X_8$-$G_1$UCUUC$G_1$UC$G_1$U-5' | 1803.8 |
| 65 | 5'-UU$G_1$CU$G_1$UU$G_1$CU-X-UC$G_1$UU$G_1$UC$G_1$UU-5' | 1046.9 |

-continued

| No | Sequence | |
|---|---|---|
| 66 | 5'-UG₁CCUUG₁AACU-X-UCAAG₁UUCCG₁U-5' | 455.3 |
| 67 | 5'-UUCUG₁CUUCUG₁-X-G₁UCUUCG₁UCUU-5' | 1275.4 |
| 68 | 5'-UUCUG₁CUUCUG₁-X₅-G₁UCUUCG₁UCUU-5' | 466.3 |
| 69 | 5'-G₁UCCUUCUCUG₁-X-G₁UCUCUUCCUG₁-5' | 618.1 |
| 70 | 5'-UG₁UURUG₁UG₁AC-X-CAG₁URUG₁UUG₁U-5' | 1125.9 |

IFN-α (pg/ml) in human PBMC assay as determined by ELISA SEQ ID NO:

| No | Sequence | at 7.15 μM |
|---|---|---|
| PBS | | 0 |
| 60 | 5'-UG₁CUG₁CCUUUG₁-X-G₁UUUCCG₁UCG₁U-5' | 907 |

IFN-α (pg/ml) in human PBMC assay by Luninex multiplex SEQ ID NO:

| No | Sequence | at 7.15 μM |
|---|---|---|
| PBS | | 46.4 |
| 63 | 5'-UG₁CUG₁CUUCUG₁-X₈-G₁UCUUCG₁UCG₁U-5' | 101.7 |
| 67 | 5'-UUCUG₁CUUCUG₁-X-G₁UCUUCG₁UCUU-5' | 133.6 |
| 68 | 5'-UUCUG₁CUUCUG₁-X₅-G₁UCUUCG₁UCUU-5' | 79.1 |

IFN-α (pg/ml) in human PBMC assay as determined by Luminex multiplex SEQ ID NO:

| No | Sequence | at 14.3 μM |
|---|---|---|
| Media | | 0 |
| 90 | 5'-UCUGAAUUCAG-X-GACUUAAGUCU-5' | 4381 |
| 92 | 5'-GCACACUUGUU-X-UUGUUCACACG-5' | 4160 |
| 93 | 5'-CACUGUUGAGA-X-AGAGUUGUCAC-5' | 1117 |
| 95 | 5'-AACUGUUGACC-X-CCAGUUGUCAA-5' | 158 |
| 96 | 5'-CAACGACCUGU-X-UGUCCAGCAAC-5' | 41 |
| 116/126 | (5'-UGCUGCUUGUG)₂-X-CCGUUGACAG-3' | 1042 |
| 117/127 | (5'-UGCUGCUUGUG)₂-X-ACACGCGUGU-3' | 2394 |
| 118 | 5'-CCCIIICCCII-X-IICCCIIICCC-5' | 9 |

IFN-α (pg/ml) in human PBMC assay as determined by Luminex multiplex SEQ ID NO:

| No | Sequence | at 7.2 μM |
|---|---|---|
| Media | | 0 |
| 104 | 5'-G₁UCCUUG₁CUUG₁-X₈-G₁UUCG₁UUCCUG₁-5' | 459 |
| 105 | 5'-G₁UCCUUG₁CUUG₁-X-G₁UUCG₁UUCCUG₁-5' | 898 |
| 106 | 5'-UUCUG₁CUUCUG₁-X₈-G₁UCUUCG₁UCUU-5' | 394 |
| 107 | 5'-UUCUG₁CUUCUG₁-X-G₁UCUUCG₁UCUU-5' | 478 |
| 108 | 5'-X₂UUCUG₁CUUCUG₁-X-G₁UCUUCG₁UCUUX₂-5' | 694 |
| 109 | 5'-X₂G₁UCCUUG₁CUUG₁-X-G₁UUCG₁UUCCUG₁X₂-5' | 1326 |
| 110 | 5'-UG₁CUG₁CCUUUG₁-X-G₁UUUCCG₁UCG₁U-5' | 153 |
| 111 | 5'-UG₁CUG₁CCUUUG₁-X₉-G₁UUUCCG₁UCG₁U-5' | 1130 |
| 112 | 5'-G₁UCCUUUG₁CUG₁-X-G₁UCG₁UUUCCUG₁-5' | 889 |

-continued

| | | |
|---|---|---|
| 113 | 5'-G₁UCCUUUG₁CUG₁-X₉-G₁UCG₁UUUCCUG₁-5' | 773 |
| 114 | 5'-X₆UGCUGCUUGUG-X-GUGUUCGUCGUX₆-5' | 65 |
| 115 | 5'-X₅GCUGCCUUUG-X₉-GUUUCCGUCGUX₅-5' | 1106 |

IFN-α (pg/ml) in human pDC assay as determined by Luminex multiplex SEQ ID NO:

| No | Sequence | at 7.2 µM |
|---|---|---|
| Media | | 0 |
| 104 | 5'-G₁UCCUUG₁CUUG₁-X₈-G₁UUCG₁UUCCUG₁-5' | 9486 |
| 105 | 5'-G₁UCCUUG₁CUUG₁-X-G₁UUCG₁UUCCUG₁-5' | 7992 |
| 106 | 5'-UUCUG₁CUUCUG₁-X₈-G₁UCUUCG₁UCUU-5' | 12305 |
| 107 | 5'-UUCUG₁CUUCUG₁-X-G₁UCUUCG₁UCUU-5' | 10144 |
| 108 | 5'-X₂UUCUG₁CUUCUG₁-X-G₁UCUUCG₁UCUUX₂-5' | 12572 |
| 109 | 5'-X₂G₁UCCUUG₁CUUG₁-X-G₁UUCG₁UUCCUG₁X₂-5' | 10584 |
| 110 | 5'-UG₁CUG₁CCUUUG₁-X-G₁UUUCCG₁UCG₁U-5' | 15426 |
| 111 | 5'-UG₁CUG₁CCUUUG₁-X₉-G₁UUUCCG₁UCG₁U-5' | 13035 |
| 112 | 5'-G₁UCCUUUG₁CUG₁-X-G₁UCG₁UUUCCUG₁-5' | 8815 |
| 113 | 5'-G₁UCCUUUG₁CUG₁-X₉-G₁UCG₁UUUCCUG₁-5' | 11210 |
| 114 | 5'-X₆UGCUGCUUGUG-X-GUGUUCGUCGUX₆-5' | 141 |
| 115 | 5'-X₅GCUGCCUUUG-X₉-GUUUCCGUCGUX₅-5' | 6480 |

The level of IL-10 (pg/ml) in human PBMC assay by Luninex multiplex SEQ ID NO:

| No | Sequence | at 7.15 µM |
|---|---|---|
| PBS | | 57.2 |
| 63 | 5'-UG₁CUG₁CUUCUG₁-X₈-G₁UCUUCG₁UCG₁U-5' | 2502.4 |
| 67 | 5'-UUCUG₁CUUCUG₁-X-G₁UCUUCG₁UCUU-5' | 2895.2 |
| 68 | 5'-UUCUG₁CUUCUG₁-X₅-G₁UCUUCG₁UCUU-5' | 2603.1 |

The level of IL-10 (pg/ml) in human PBMC assay as determined by Luminex multiplex SEQ ID NO:

| No | Sequence | at 14.3 µM |
|---|---|---|
| Media | | 13 |
| 90 | 5'-UCUGAAUUCAG-X-GACUUAAGUCU-5' | 7713 |
| 92 | 5'-GCACACUUGUU-X-UUGUUCACACG-5' | 6780 |
| 93 | 5'-CACUGUUGAGA-X-AGAGUUGUCAC-5' | 5457 |
| 95 | 5'-AACUGUUGACC-X-CCAGUUGUCAA-5' | 7152 |
| 96 | 5'-CAACGACCUGU-X-UGUCCAGCAAC-5' | 8675 |
| 116/126 | (5'-UGCUGCUUGUG)₂-X-CCGUUGACAG-3' | 1230 |
| 117/127 | (5'-UGCUGCUUGUG)₂-X-ACACGCGUGU-3' | 2378 |
| 118 | 5'-CCCIIICCCII-X-IICCCIIICCC-5' | 6324 |

| The level of IL-10 (pg/ml) in human PBMC assay as determined by Luminex multiplex SEQ ID NO: | | |
|---|---|---|
| No | Sequence | at 7.2 µM |
| Media | | 7 |
| 104 | 5'-$G_1$UCCUUG$_1$CUUG$_1$-$X_8$-$G_1$UUCG$_1$UUCCUG$_1$-5' | 184 |
| 105 | 5'-$G_1$UCCUUG$_1$CUUG$_1$-X-$G_1$UUCG$_1$UUCCUG$_1$-5' | 242 |
| 106 | 5'-UUCUG$_1$CUUCUG$_1$-$X_8$-$G_1$UCUUCG$_1$UCUU-5' | 126 |
| 107 | 5'-UUCUG$_1$CUUCUG$_1$-X-$G_1$UCUUCG$_1$UCUU-5' | 88 |
| 108 | 5'-$X_2$UUCUG$_1$CUUCUG$_1$-X-$G_1$UCUUCG$_1$UCUU$X_2$-5' | 169 |
| 109 | 5'-$X_2G_1$UCCUUG$_1$CUUG$_1$-X-$G_1$UUCG$_1$UUCCUG$_1X_2$-5' | 285 |
| 110 | 5'-U$G_1$CUG$_1$CCUUUG$_1$-X-$G_1$UUUCCG$_1$UCG$_1$U-5' | 392 |
| 111 | 5'-U$G_1$CUG$_1$CCUUUG$_1$-$X_9$-$G_1$UUUCCG$_1$UCG$_1$U-5' | 189 |
| 112 | 5'-$G_1$UCCUUUG$_1$CUG$_1$-X-$G_1$UCG$_1$UUUCCUG$_1$-5' | 270 |
| 113 | 5'-$G_1$UCCUUUG$_1$CUG$_1$-$X_9$-$G_1$UCG$_1$UUUCCUG$_1$-5' | 183 |
| 114 | 5'-$X_6$UGCUGCUUGUG-X-GUGUUCGUCGU$X_6$-5' | 417 |
| 115 | 5'-$X_5$GCUGCCUUUG-$X_9$-GUUUCCGUCGU$X_5$-5' | 331 |

| The level of IL-12 (pg/ml) in human PBMC assay as determined by Luminex multiplex SEQ ID NO: | | |
|---|---|---|
| No | Sequence | at 14.3 µM |
| Media | | 39 |
| 90 | 5'-UCUGAAUUCAG-X-GACUUAAGUCU-5' | 6551 |
| 92 | 5'-GCACACUUGUU-X-UUGUUCACACG-5' | 4305 |
| 93 | 5'-CACUGUUGAGA-X-AGAGUUGUCAC-5' | 7915 |
| 95 | 5'-AACUGUUGACC-X-CCAGUUGUCAA-5' | 6440 |
| 96 | 5'-CAACGACCUGU-X-UGUCCAGCAAC-5' | 4701 |
| 116/126 | (5'-UGCUGCUUGUG)$_2$-X-CCGUUGACAG-3' | 8065 |
| 117/127 | (5'-UGCUGCUUGUG)$_2$-X-ACACGCGUGU-3' | 10226 |
| 118 | 5'-CCCIIICCCII-X-IICCCIIICCC-5' | 1944 |

| The level of IL-12 (pg/ml) in human PBMC assay as determined by Luminex multiplex SEQ ID NO: | | |
|---|---|---|
| No | Sequence | at 7.2 µM |
| Media | | 25 |
| 104 | 5'-$G_1$UCCUUG$_1$CUUG$_1$-$X_8$-$G_1$UUCG$_1$UUCCUG$_1$-5' | 1410 |
| 105 | 5'-$G_1$UCCUUG$_1$CUUG$_1$-X-$G_1$UUCG$_1$UUCCUG$_1$-5' | 1405 |
| 106 | 5'-UUCUG$_1$CUUCUG$_1$-$X_8$-$G_1$UCUUCG$_1$UCUU-5' | 750 |
| 107 | 5'-UUCUG$_1$CUUCUG$_1$-X-$G_1$UCUUCG$_1$UCUU-5' | 671 |
| 108 | 5'-$X_2$UUCUG$_1$CUUCUG$_1$-X-$G_1$UCUUCG$_1$UCUU$X_2$-5' | 875 |
| 109 | 5'-$X_2G_1$UCCUUG$_1$CUUG$_1$-X-$G_1$UUCG$_1$UUCCUG$_1X_2$-5' | 2749 |
| 110 | 5'-U$G_1$CUG$_1$CCUUUG$_1$-X-$G_1$UUUCCG$_1$UCG$_1$U-5' | 2742 |
| 111 | 5'-U$G_1$CUG$_1$CCUUUG$_1$-$X_9$-$G_1$UUUCCG$_1$UCG$_1$U-5' | 1110 |
| 112 | 5'-$G_1$UCCUUUG$_1$CUG$_1$-X-$G_1$UCG$_1$UUUCCUG$_1$-5' | 1428 |
| 113 | 5'-$G_1$UCCUUUG$_1$CUG$_1$-$X_9$-$G_1$UCG$_1$UUUCCUG$_1$-5' | 1126 |

-continued

| | | |
|---|---|---|
| 114 | 5'-X$_6$UGCUGCUUGUG-X-GUGUUCGUCGUX$_6$-5' | 3034 |
| 115 | 5'-X$_5$GCUGCCUUUG-X$_9$-GUUUCCGUCGUX$_5$-5' | 2055 |

| The level of IP-10 (pg/ml) in human PBMC assay by Luninex multiplex SEQ ID NO: | | |
|---|---|---|
| No | Sequence | at 7.15 µM |
| PBS | | 0 |
| 63 | 5'-U G$_1$CUG$_1$CUUCUG$_1$-X$_8$-G$_1$UCUUCG$_1$UCG$_1$U-5' | 132.3 |
| 67 | 5'-UUCUG$_1$CUUCUG$_1$-X-G$_1$UCUUCG$_1$UCUU-5' | 122.7 |
| 68 | 5'-UUCUG$_1$CUUCUG$_1$-X$_5$-G$_1$UCUUCG$_1$UCUU-5' | 13.9 |

| The level of IP-10 (pg/ml) in human PBMC assay as determined by Luminex multiplex SEQ ID NO: | | |
|---|---|---|
| No | Sequence | at 14.3 µM |
| Media | | 28 |
| 90 | 5'-UCUGAAUUCAG-X-GACUUAAGUCU-5' | 398 |
| 92 | 5'-GCACACUUGUU-X-UUGUUCACACG-5' | 358 |
| 93 | 5'-CACUGUUGAGA-X-AGAGUUGUCAC-5' | 679 |
| 95 | 5'-AACUGUUGACC-X-CCAGUUGUCAA-5' | 613 |
| 96 | 5'-CAACGACCUGU-X-UGUCCAGCAAC-5' | 318 |
| 116/126 | (5'-UGCUGCUUGUG)$_2$-X-CCGUUGACAG-3' | 263 |
| 117/127 | (5'-UGCUGCUUGUG)$_2$-X-ACACGCGUGU-3' | 245 |
| 118 | 5'-CCCIIICCCII-X-IICCCIIICCC-5' | 140 |

| The level of IP-10 (pg/ml) in human PBMC assay as determined by Luminex multiplex SEQ ID NO: | | |
|---|---|---|
| No | Sequence | at 7.2 µM |
| Media | | 28 |
| 104 | 5'-G$_1$UCCUUG$_1$CUUG$_1$-X$_8$-G$_1$UUCG$_1$UUCCUG$_1$-5' | 835 |
| 105 | 5'-G$_1$UCCUUG$_1$CUUG$_1$-X-G$_1$UUCG$_1$UUCCUG$_1$-5' | 847 |
| 106 | 5'-UUCUG$_1$CUUCUG$_1$-X$_8$-G$_1$UCUUCG$_1$UCUU-5' | 587 |
| 107 | 5'-UUCUG$_1$CUUCUG$_1$-X-G$_1$UCUUCG$_1$UCUU-5' | 661 |
| 108 | 5'-X$_2$UUCUG$_1$CUUCUG$_1$-X-G$_1$UCUUCG$_1$UCUUX$_2$-5' | 696 |
| 109 | 5'-X$_2$G$_1$UCCUUG$_1$CUUG$_1$-X-G$_1$UUCG$_1$UUCCUG$_1$X$_2$-5' | 943 |
| 110 | 5'-UG$_1$CUG$_1$CCUUUG$_1$-X-G$_1$UUUCCG$_1$UCG$_1$U-5' | 927 |
| 111 | 5'-UG$_1$CUG$_1$CCUUUG$_1$-X$_9$-G$_1$UUUCCG$_1$UCG$_1$U-5' | 796 |
| 112 | 5'-G$_1$UCCUUUG$_1$CUG$_1$-X-G$_1$UCG$_1$UUUCCUG$_1$-5' | 827 |
| 113 | 5'-G$_1$UCCUUUG$_1$CUG$_1$-X$_9$-G$_1$UCG$_1$UUUCCUG$_1$-5' | 815 |
| 114 | 5'-X$_6$UGCUGCUUGUG-X-GUGUUCGUCGUX$_6$-5' | 659 |
| 115 | 5'-X$_5$GCUGCCUUUG-X$_9$-GUUUCCGUCGUX$_5$-5' | 890 |

-continued

| | | The level of IP-10 (pg/ml) in human pDC assay as determined by Luminex multiplex SEQ ID NO: |
|---|---|---|
| No | Sequence | at 7.2 µM |
| Media | | 28 |
| 104 | 5'-G$_1$UCCUUG$_1$CUUG$_1$-X$_8$-G$_1$UUCG$_1$UUCCUG$_1$-5' | 166 |
| 105 | 5'-G$_1$UCCUUG$_1$CUUG$_1$-X-G$_1$UUCG$_1$UUCCUG$_1$-5' | 257 |
| 106 | 5'-UUCUG$_1$CUUCUG$_1$-X$_8$-G$_1$UCUUCG$_1$UCUU-5' | 128 |
| 107 | 5'-UUCUG$_1$CUUCUG$_1$-X-G$_1$UCUUCG$_1$UCUU-5' | 180 |
| 108 | 5'-X$_2$UUCUG$_1$CUUCUG$_1$-X-G$_1$UCUUCG$_1$UCUUX$_2$-5' | 138 |
| 109 | 5'-X$_2$G$_1$UCCUUG$_1$CUUG$_1$-X-G$_1$UUCG$_1$UUCCUG$_1$X$_2$-5' | 348 |
| 110 | 5'-U G$_1$CUG$_1$CCUUUG$_1$-X-G$_1$UUUCCG$_1$UCG$_1$U-5' | 416 |
| 111 | 5'-U G$_1$CUG$_1$CCUUUG$_1$-X$_9$-G$_1$UUUCCG$_1$UCG$_1$U-5' | 144 |
| 112 | 5'-G$_1$UCCUUUG$_1$CUG$_1$-X-G$_1$UCG$_1$UUUCCUG$_1$-5' | 230 |
| 113 | 5'-G$_1$UCCUUUG$_1$CUG$_1$-X$_9$-G$_1$UCG$_1$UUUCCUG$_1$-5' | 171 |
| 114 | 5'-X$_6$UGCUGCUUGUG-X-GUGUUCGUCGUX$_6$-5' | 89 |
| 115 | 5'-X$_5$GCUGCCUUUG-X$_9$-GUUUCCGUCGUX$_5$-5' | 126 |

| | | The level of IL-8 (pg/ml) in human PBMC assay as determined by Luminex multiplex SEQ ID NO: |
|---|---|---|
| No | Sequence | at 14.3 µM |
| Media | | 273 |
| 90 | 5'-UCUGAAUUCAG-X-GACUUAAGUCU-5' | 4078 |
| 92 | 5'-GCACACUUGUU-X-UUGUUCACACG-5' | 13018 |
| 95 | 5'-AACUGUUGACC-X-CCAGUUGUCAA-5' | 5898 |
| 96 | 5'-CAACGACCUGU-X-UGUCCAGCAAC-5' | 6386 |
| 116/126 | (5'-UGCUGCUUGUG)$_2$-X-CCGUUGACAG-3' | 8506 |
| 117/127 | (5'-UGCUGCUUGUG)$_2$-X-ACACGCGUGU-3' | 5776 |
| 118 | 5'-CCCIIICCCII-X-IICCCIIICCC-5' | 4494 |

| | | The level of IL-8 (pg/ml) in human PBMC assay as determined by Luminex multiplex SEQ ID NO: |
|---|---|---|
| No | Sequence | at 7.2 µM |
| Media | | 1982 |
| 104 | 5'-G$_1$UCCUUG$_1$CUUG$_1$-X$_8$-G$_1$UUCG$_1$UUCCUG$_1$-5' | 46124 |
| 105 | 5'-G$_1$UCCUUG$_1$CUUG$_1$-X-G$_1$UUCG$_1$UUCCUG$_1$-5' | 88695 |
| 106 | 5'-UUCUG$_1$CUUCUG$_1$-X$_8$-G$_1$UCUUCG$_1$UCUU-5' | 113574 |
| 107 | 5'-UUCUG$_1$CUUCUG$_1$-X-G$_1$UCUUCG$_1$UCUU-5' | 33359 |
| 108 | 5'-X$_2$UUCUG$_1$CUUCUG$_1$-X-G$_1$UCUUCG$_1$UCUUX$_2$-5' | 155855 |
| 109 | 5'-X$_2$G$_1$UCCUUG$_1$CUUG$_1$-X-G$_1$UUCG$_1$UUCCUG$_1$X$_2$-5' | 90944 |
| 110 | 5'-UG$_1$CUG$_1$CCUUUG$_1$-X-G$_1$UUUCCG$_1$UCG$_1$U-5' | 106354 |
| 111 | 5'-UG$_1$CUG$_1$CCUUUG$_1$-X$_9$-G$_1$UUUCCG$_1$UCG$_1$U-5' | 129362 |
| 112 | 5'-G$_1$UCCUUUG$_1$CUG$_1$-X-G$_1$UCG$_1$UUUCCUG$_1$-5' | 1397924 |
| 113 | 5'-G$_1$UCCUUUG$_1$CUG$_1$-X$_9$-G$_1$UCG$_1$UUUCCUG$_1$-5' | 71610 |

| No | Sequence | SEQ ID NO: |
|---|---|---|
| 114 | 5'-X$_6$UGCUGCUUGUG-X-GUGUUCGUCGUX$_6$-5' | 208436 |
| 115 | 5'-X$_5$GCUGCCUUUG-X$_9$-GUUUCCGUCGUX$_5$-5' | 103725 |

| | The level of MCP-1 (pg/ml) in human PBMC assay as determined by Luminex multiplex SEQ ID NO: | |
|---|---|---|
| No | Sequence | at 14.3 µM |
| Media | | 12 |
| 90 | 5'-UCUGAAUUCAG-X-GACUUAAGUCU-5' | 3010 |
| 92 | 5'-GCACACUUGUU-X-UUGUUCACACG-5' | 3533 |
| 93 | 5'-CACUGUUGAGA-X-AGAGUUGUCAC-5' | 3188 |
| 95 | 5'-AACUGUUGACC-X-CCAGUUGUCAA-5' | 2770 |
| 96 | 5'-CAACGACCUGU-X-UGUCCAGCAAC-5' | 3589 |
| 116/126 | (5'-UGCUGCUUGUG)$_2$-X-CCGUUGACAG-3' | 521 |
| 117/127 | (5'-UGCUGCUUGUG)$_2$-X-ACACGCGUGU-3' | 997 |
| 118 | 5'-CCCIIICCCII-X-IICCCIIICCC-5' | 2308 |

| | The level of MCP-1 (pg/ml) in human PBMC assay as determined by Luminex multiplex SEQ ID NO: | |
|---|---|---|
| No | Sequence | at 7.2 µM |
| Media | | 79 |
| 104 | 5'-G$_1$UCCUUG$_1$CUUG$_1$-X$_8$-G$_1$UUCG$_1$UUCCUG$_1$-5' | 192086 |
| 105 | 5'-G$_1$UCCUUG$_1$CUUG$_1$-X-G$_1$UUCG$_1$UUCCUG$_1$-5' | 361681 |
| 106 | 5'-UUCUG$_1$CUUCUG$_1$-X$_8$-G$_1$UCUUCG$_1$UCUU-5' | 160970 |
| 107 | 5'-UUCUG$_1$CUUCUG$_1$-X-G$_1$UCUUCG$_1$UCUU-5' | 139299 |
| 108 | 5'-X$_2$UUCUG$_1$CUUCUG$_1$-X-G$_1$UCUUCG$_1$UCUUX$_2$-5' | 294514 |
| 109 | 5'-X$_2$G$_1$UCCUUG$_1$CUUG$_1$-X-G$_1$UUCG$_1$UUCCUG$_1$X$_2$-5' | 109354 |
| 110 | 5'-UG$_1$CUG$_1$CCUUUG$_1$-X-G$_1$UUUCCG$_1$UCG$_1$U-5' | 218045 |
| 111 | 5'-UG$_1$CUG$_1$CCUUUG$_1$-X$_9$-G$_1$UUUCCG$_1$UCG$_1$U-5' | 183109 |
| 112 | 5'-G$_1$UCCUUUG$_1$CUG$_1$-X-G$_1$UCG$_1$UUUCCUG$_1$-5' | 278467 |
| 113 | 5'-G$_1$UCCUUUG$_1$CUG$_1$-X$_9$-G$_1$UCG$_1$UUUCCUG$_1$-5' | 210977 |
| 114 | 5'-X$_6$UGCUGCUUGUG-X-GUGUUCGUCGUX$_6$-5' | 149298 |
| 115 | 5'-X$_5$GCUGCCUUUG-X$_9$-GUUUCCGUCGUX$_5$-5' | 112087 |

| | The level of MIP-1α (pg/ml) in human PBMC assay as determined by Luminex multiplex SEQ ID NO: | |
|---|---|---|
| No | Sequence | at 14.3 µM |
| Media | | 21 |
| 90 | 5'-UCUGAAUUCAG-X-GACUUAAGUCU-5' | 19586 |
| 92 | 5'-GCACACUUGUU-X-UUGUUCACACG-5' | 5037 |
| 93 | 5'-CACUGUUGAGA-X-AGAGUUGUCAC-5' | 16677 |
| 95 | 5'-AACUGUUGACC-X-CCAGUUGUCAA-5' | 3575 |
| 96 | 5'-CAACGACCUGU-X-UGUCCAGCAAC-5' | 566 |
| 116/126 | (5'-UGCUGCUUGUG)$_2$-X-CCGUUGACAG-3' | 24329 |

| | | -continued | |
|---|---|---|---|
| 117/127 | (5'-UGCUGCUUGUG)$_2$-X-ACACGCGUGU-3' | | 39964 |
| 118 | 5'-CCCIIICCCII-X-IICCCIIICCC-5' | | 25 |

The level of MIP-1α (pg/ml) in human PBMC assay as determined by Luminex multiplex SEQ ID NO:

| No | Sequence | at 7.2 µM |
|---|---|---|
| Media | | 31 |
| 104 | 5'-G$_1$UCCUUG$_1$CUUG$_1$-X$_8$-G$_1$UUCG$_1$UUCCUG$_1$-5' | 8103 |
| 105 | 5'-G$_1$UCCUUG$_1$CUUG$_1$-X-G$_1$UUCG$_1$UUCCUG$_1$-5' | 11628 |
| 106 | 5'-UUCUG$_1$CUUCUG$_1$-X$_8$-G$_1$UCUUCG$_1$UCUU-5' | 4511 |
| 107 | 5'-UUCUG$_1$CUUCUG$_1$-X-G$_1$UCUUCG$_1$UCUU-5' | 3858 |
| 108 | 5'-X$_2$UUCUG$_1$CUUCUG$_1$-X-G$_1$UCUUCG$_1$UCUUX$_2$-5' | 6507 |
| 109 | 5'-X$_2$G$_1$UCCUUG$_1$CUUG$_1$-X-G$_1$UUCG$_1$UUCCUG$_1$X$_2$-5' | 17164 |
| 110 | 5'-UG$_1$CUG$_1$CCUUUG$_1$-X-G$_1$UUUCCG$_1$UCG$_1$U-5' | 15559 |
| 111 | 5'-UG$_1$CUG$_1$CCUUUG$_1$-X$_9$-G$_1$UUUCCG$_1$UCG$_1$U-5' | 7714 |
| 112 | 5'-G$_1$UCCUUUG$_1$CUG$_1$-X-G$_1$UCG$_1$UUUCCUG$_1$-5' | 11119 |
| 113 | 5'-G$_1$UCCUUUG$_1$CUG$_1$-X$_9$-G$_1$UCG$_1$UUUCCUG$_1$-5' | 9111 |
| 114 | 5'-X$_6$UGCUGCUUGUG-X-GUGUUCGUCGUX$_6$-5' | 20355 |
| 115 | 5'-X$_5$GCUGCCUUUG-X$_9$-GUUUCCGUCGUX$_5$-5' | 16284 |

The level of MIP-1β (pg/ml) in human PBMC assay as determined by Luminex multiplex SEQ ID NO:

| No | Sequence | at 14.3 µM |
|---|---|---|
| Media | | 175 |
| 90 | 5'-UCUGAAUUCAG-X-GACUUAAGUCU-5' | 42262 |
| 92 | 5'-GCACACUUGUU-X-UUGUUCACACG-5' | 42685 |
| 93 | 5'-CACUGUUGAGA-X-AGAGUUGUCAC-5' | 39680 |
| 95 | 5'-AACUGUUGACC-X-CCAGUUGUCAA-5' | 48949 |
| 96 | 5'-CAACGACCUGU-X-UGUCCAGCAAC-5' | 47724 |
| 116/126 | (5'-UGCUGCUUGUG)$_2$-X-CCGUUGACAG-3' | 38198 |
| 117/127 | (5'-UGCUGCUUGUG)$_2$-X-ACACGCGUGU-3' | 44528 |
| 118 | 5'-CCCIIICCCII-X-IICCCIIICCC-5' | 49838 |

The level of MIP-1β (pg/ml) in human PBMC assay as determined by Luminex multiplex SEQ ID NO:

| No | Sequence | at 7.2 µM |
|---|---|---|
| Media | | 77 |
| 104 | 5'-G$_1$UCCUUG$_1$CUUG$_1$-X$_8$-G$_1$UUCG$_1$UUCCUG$_1$-5' | 18921 |
| 105 | 5'-G$_1$UCCUUG$_1$CUUG$_1$-X-G$_1$UUCG$_1$UUCCUG$_1$-5' | 30590 |
| 106 | 5'-UUCUG$_1$CUUCUG$_1$-X$_8$-G$_1$UCUUCG$_1$UCUU-5' | 13947 |
| 107 | 5'-UUCUG$_1$CUUCUG$_1$-X-G$_1$UCUUCG$_1$UCUU-5' | 12919 |
| 108 | 5'-X$_2$UUCUG$_1$CUUCUG$_1$-X-G$_1$UCUUCG$_1$UCUUX$_2$-5' | 14264 |
| 109 | 5'-X$_2$G$_1$UCCUUG$_1$CUUG$_1$-X-G$_1$UUCG$_1$UUCCUG$_1$X$_2$-5' | 35365 |
| 110 | 5'-UG$_1$CUG$_1$CCUUUG$_1$-X-G$_1$UUUCCG$_1$UCG$_1$U-5' | 38605 |

-continued

| | | |
|---|---|---|
| 111 | 5'-UG₁CUG₁CCUUUG₁-X₉-G₁UUUCCG₁UCG₁U-5' | 11093 |
| 112 | 5'-G₁UCCUUUG₁CUG₁-X-G₁UCG₁UUUCCUG₁-5' | 24994 |
| 113 | 5'-G₁UCCUUUG₁CUG₁-X₉-G₁UCG₁UUUCCUG₁-5' | 17191 |
| 114 | 5'-X₆UGCUGCUUGUG-X-GUGUUCGUCGUX₆-5' | 18002 |
| 115 | 5'-X₅GCUGCCUUUG-X₉-GUUUCCGUCGUX₅-5' | 24605 |

| Cytokine secretion in human cell-based assays SEQ ID NO: | | | | |
|---|---|---|---|---|
| No | Sequence | PBMC IFN-α Pg/ml + SD | PBMC IL-6 Pg/ml + SD | PBMC TNF-α Pg/ml + SD |
| PBS | | 0 ± 0 | 0 ± 0 | 0 ± 0 |
| 1 | 5'-UGCUGCUUCUG-X-GUCUUCGUCGU-5' | 1250 ± 467 | 5558 ± 207 | 3902 ± 506 |
| 11 | 5'-UG₁CUG₁CUUCUG₁-X-G₁UCUUCG₁UCG₁U-5' | 1122 ± 818 | 6101 ± 423 | 2012 ± 163 |
| 12 | 5'-G₁UCCUUCAACU-X-UCAACUUCCUG₁-5' | NT | 5063 ± 808 | 1139 ± 1374 |
| 13 | 5'-GUCCUUCAACU-X-UCAACUUCCUG-5' | NT | 906 ± 359 | 439 ± 620 |
| R848 (28.6 μM) | | 956 ± 521 | 7396 ± 139 | 3263 ± 4615 |
| 7-deazaG (28.6 μM) | | 184 ± 260 | 105 ± 148 | 0 |

At 14.3 μM

| Cytokine secretion in human cell-based assays SEQ ID NO: | | | |
|---|---|---|---|
| No | Sequence | pDC IFN-α Pg/ml + SD | pDC TNF-α Pg/ml + SD |
| PBS | | 0 ± 0 | 136 ± 0 |
| 1 | 5'-UGCUGCUUCUG-X-GUCUUCGUCGU-5' | 15683 ± 3589 | 3373 ± 627 |
| 11 | 5'-UG₁CUG₁CUUCUG₁-X-G₁UCUUCG₁UCG₁U-5' | 18981 + 10631 | 3721 + 342 |
| 12 | 5'-G₁UCCUUCAACU-X-UCAACUUCCUG₁-5' | 10370 + 6546 | 1744 + 786 |
| 13 | 5'-GUCCUUCAACU-X-UCAACUUCCUG-5' | 7792 + 2246 | 1031 + 620 |

At 14.3 μM

| Cytokine secretion in human cell-based assays SEQ ID NO: | | | | |
|---|---|---|---|---|
| No | Sequence | pDC IFN-α Pg/ml + SD | PBMC IFN-α Pg/ml + SD | PBMC IL-6 Pg/ml + SD |
| PBS | | 79 ± 12 | 5.0 ± 0 | 54 ± 0 |
| 1 | 5'-UGCUGCUUCUG-X-GUCUUCGUCGU-5' | 31134 ± 584 | 3214 ± 18 | 3610 ± 130 |
| 11 | 5'-UG₁CUG₁CUUCUG₁-X-G₁UCUUCG₁UCG₁U-5' | 322238 ± 618 | 1823 ± 13 | 3074 ± 194 |
| 17 | 5'-UOCUOCUUCUO-X-OUCUUCOUCOU-5' | 18844 ± 241 | 1087 ± 16 | 858 ± 160 |
| 18 | 5'-UICUICUUCUI-X-IUCUUCIUCIU-5' | 345 ± 0 | 0 | 57 ± 3 |
| Loxoribine (28.6 μM) | | 26310 ± 122 | 2820 ± 0 | 508 |

At 14.3 μM

In Vivo Anti-Cancer Activity of RNA Based Oligonucleotides in Mouse Model

Figure 9:
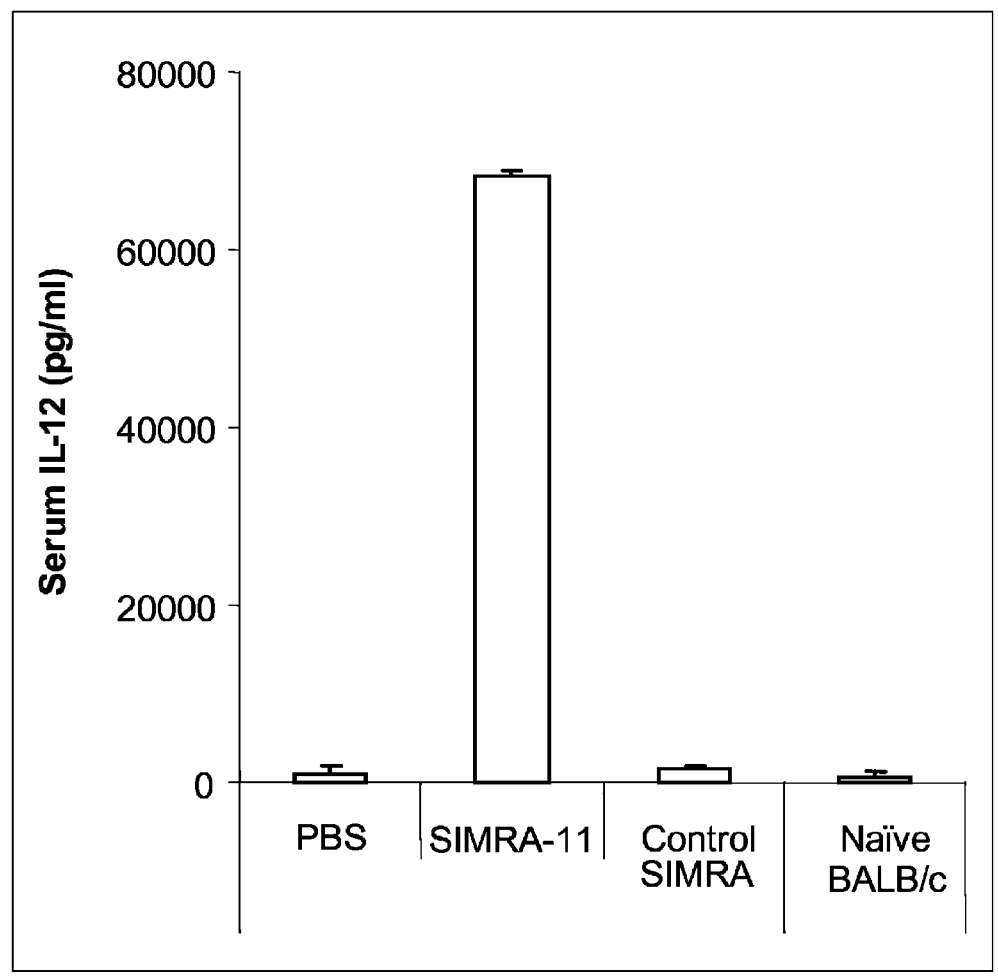
FIG. 9 depicts serum IL-12 concentrations, as determined by ELISA, in tumor cell injected mice 4 hours after administration of a SIMRA compound of the invention, demonstrating that an increased amount of IL-12 following administration of a SIMRA compound to a tumor bearing mammal.
Figure 10:
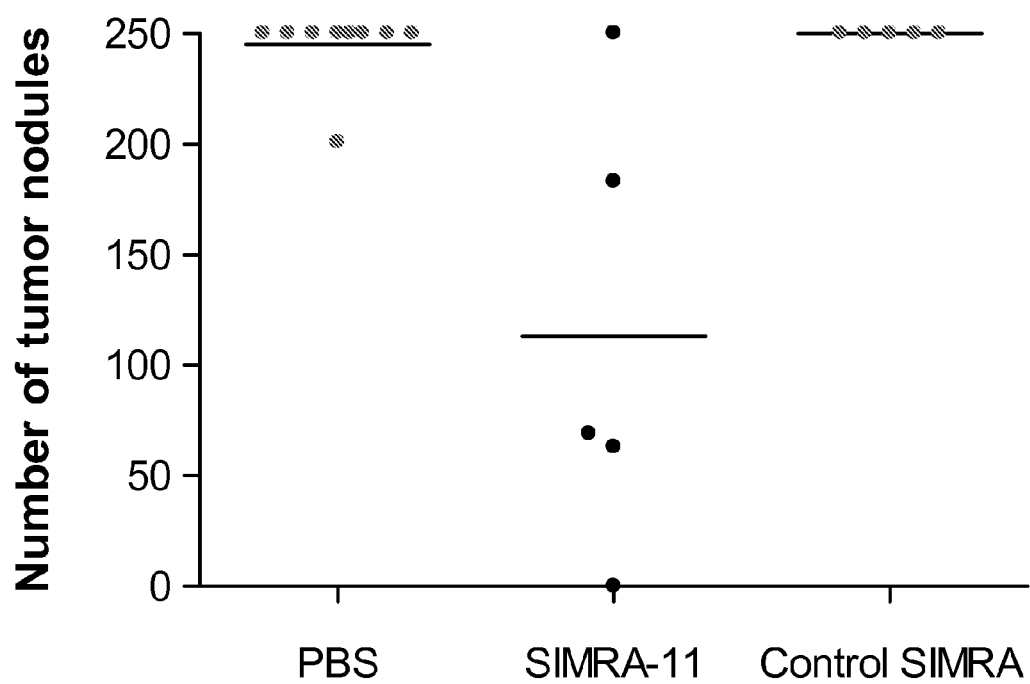
FIG. 10 depicts the number of tumor nodules in a mouse tumor model after administration of a SIMRA compound of the invention, demonstrating that a SIMRA compound reduces the number of tumor nodules following in vivo administration.
Figure 11:
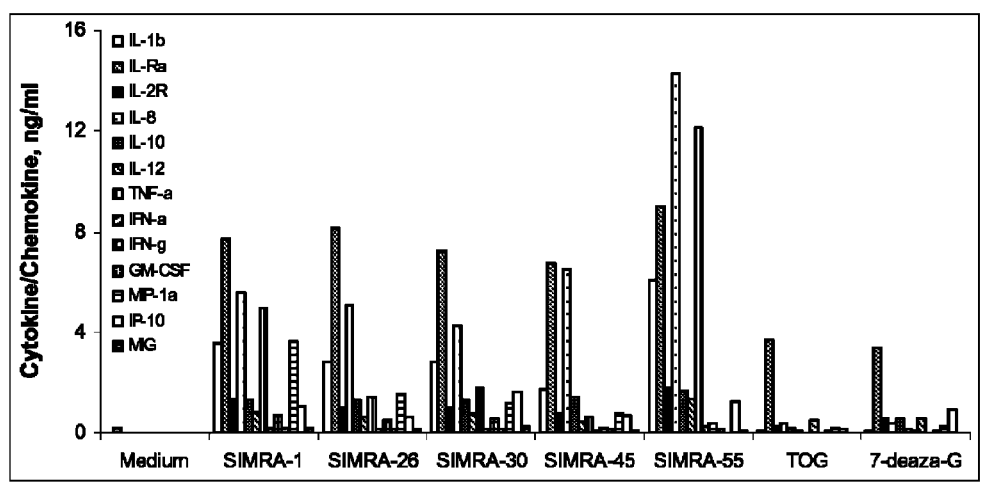
FIGS. 11A through 11D depicts cytokine/chemokine profiles from human PBMCs and pDCs treated with SIMRA compounds of the invention.
Figure 11:
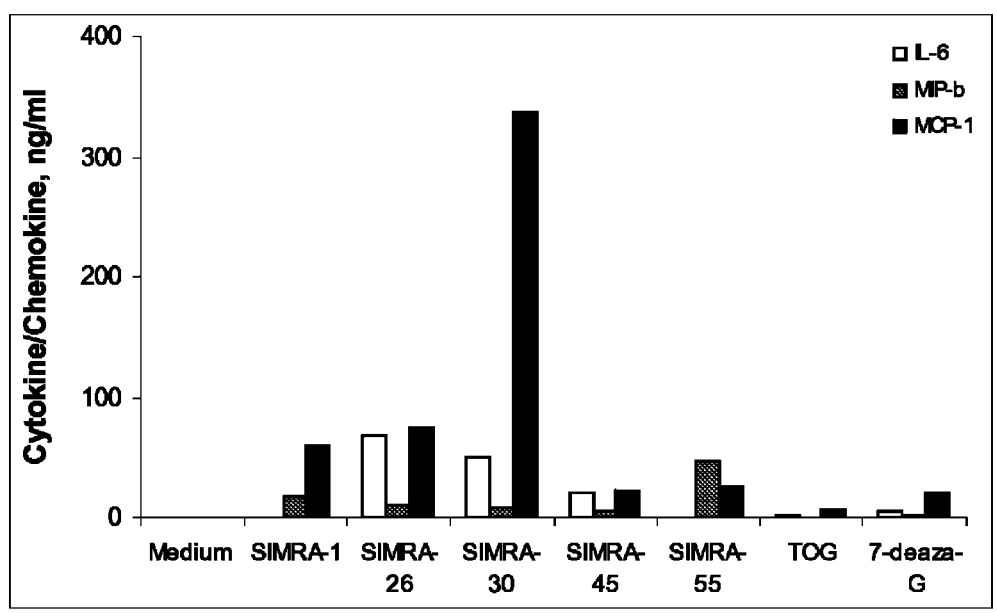
Figure 11:
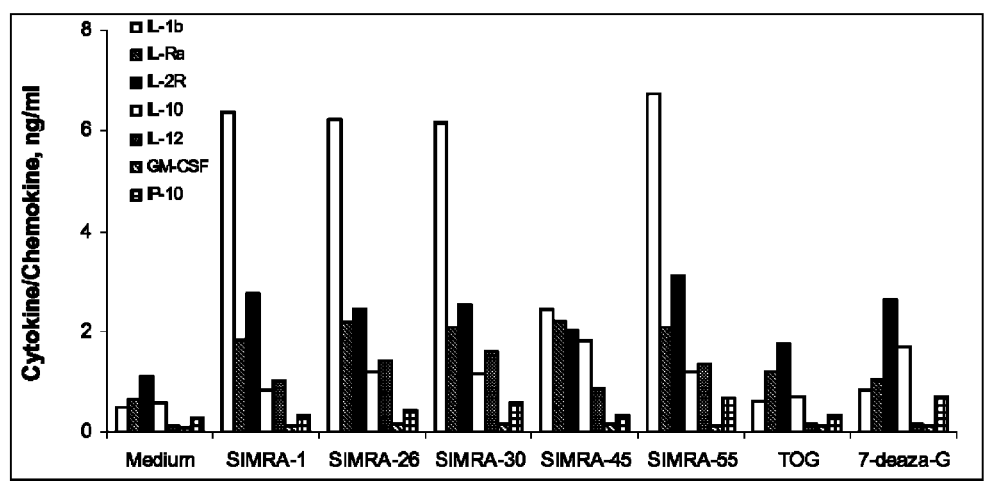
Figure 11:
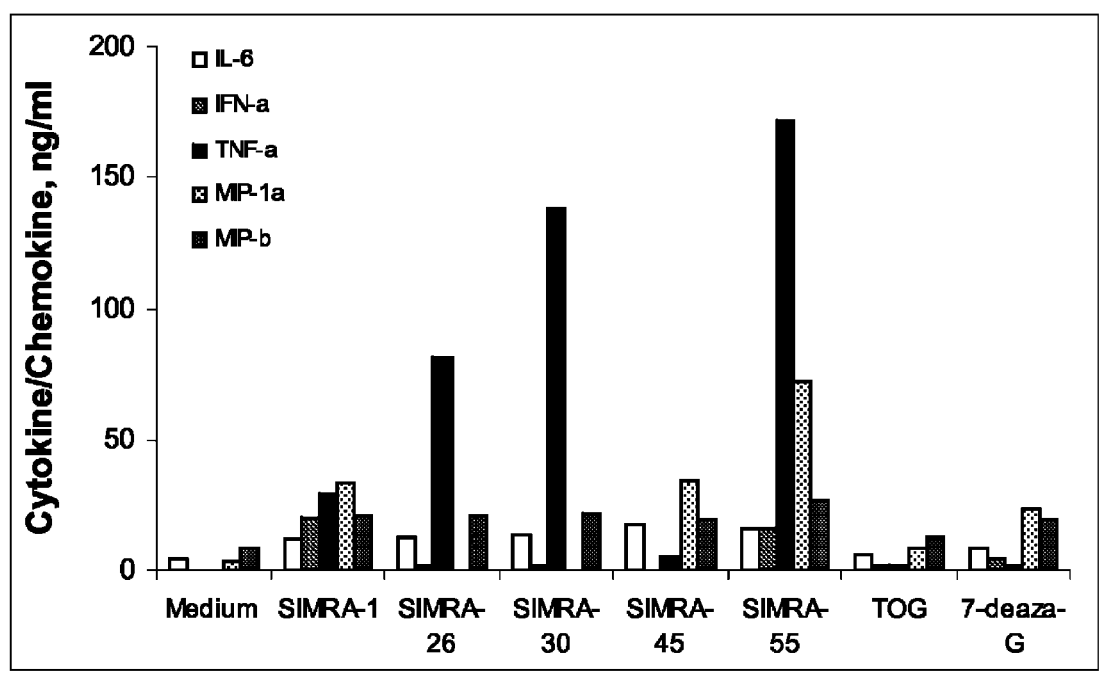
Figure 12:
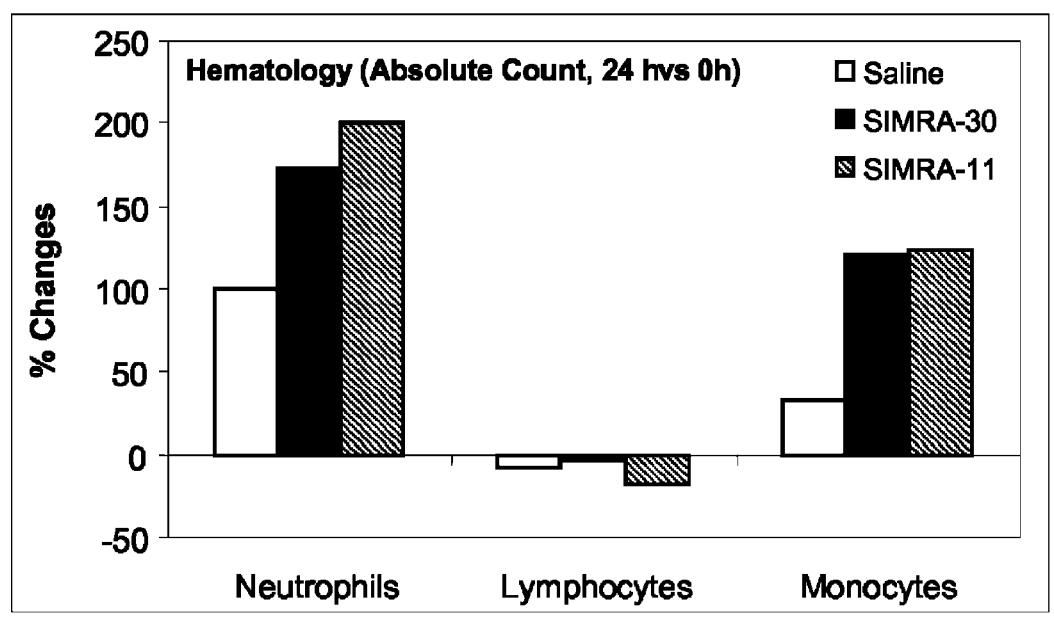
FIG. 12 depicts the change in the hematology profile in Cynomolgus monkeys 24 hours after administration of SIMRA compounds, demonstrating that SIMRA compounds can induce effects on select immune cells.
Figure 13:
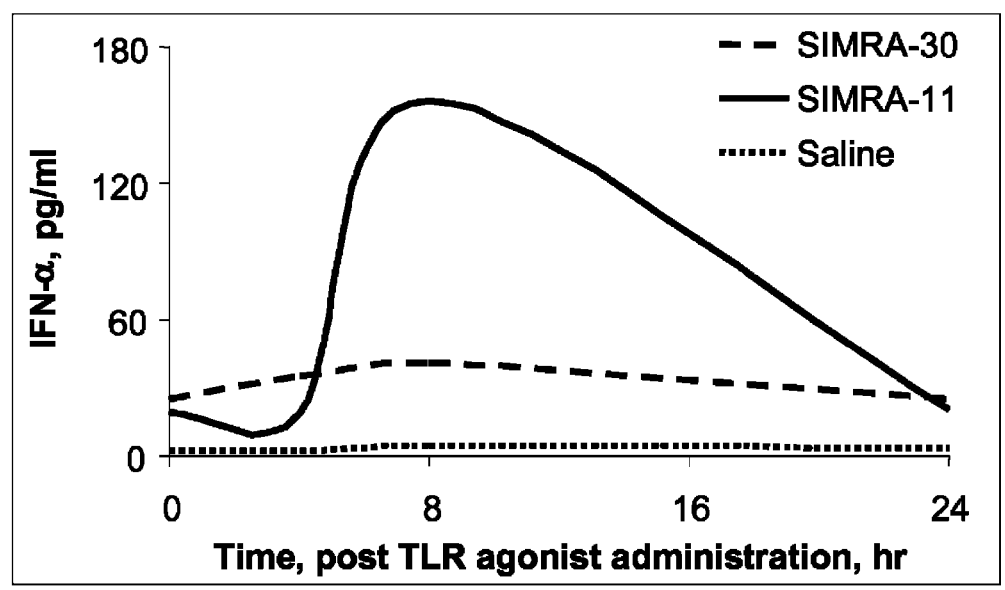
FIGS. 13A and 13B depict plasma cytokine/chemokine concentrations in Cynomolgus monkeys 24 hours after administration of SIMRA compounds, as measured by ELISA, demonstrating that SIMRA compounds (e.g. SEQ ID NOs 11 and 30) can effect cytokine/chemokine profiles in vivo.
Figure 13:
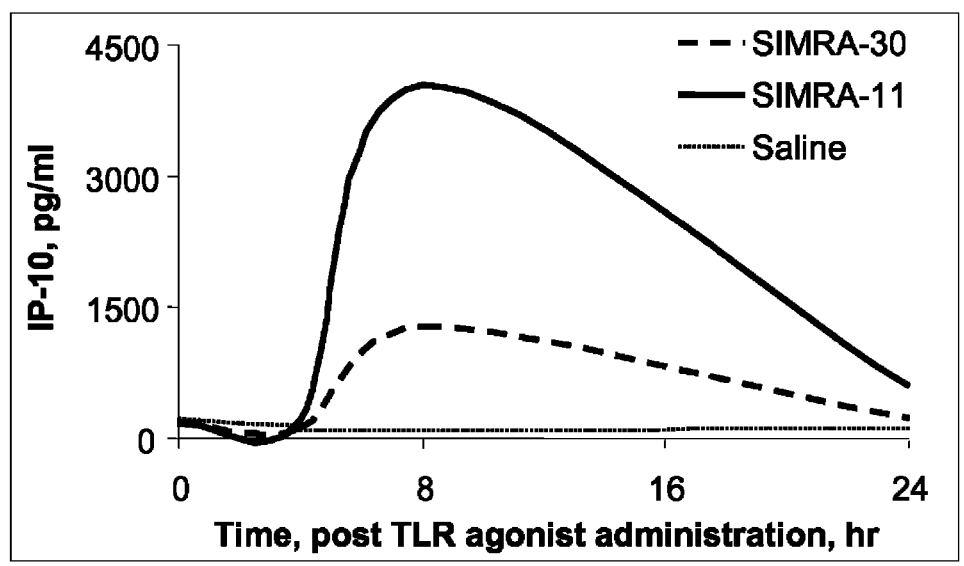
Figure 14:
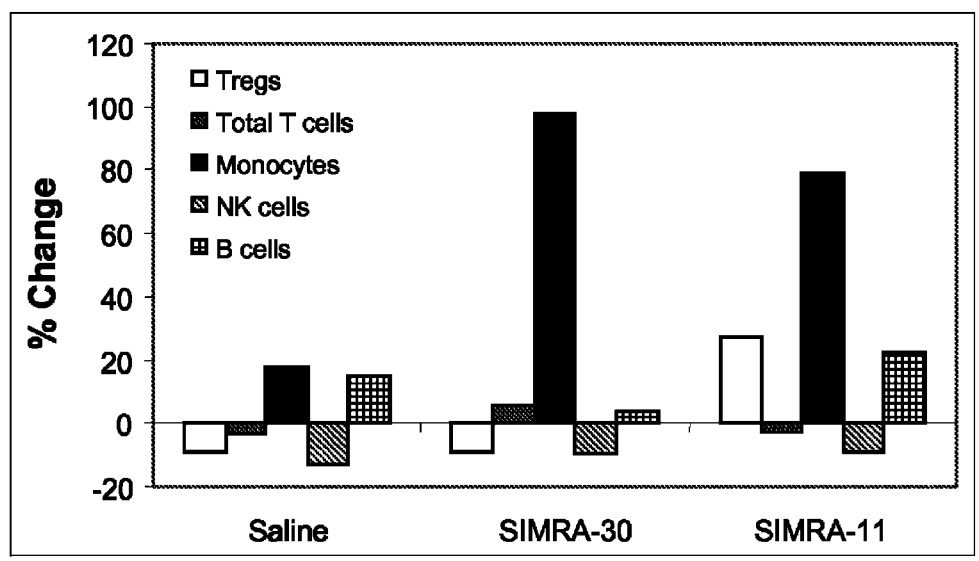
FIG. 14 depicts changes in T-regulatory cell number, Total T-cell number, monocyte number, NK cell number and B-cell number in Cynomolgus monkeys at 24 hours post dosing compared to 0 hours, as measured by Flow cytometry, demonstrating that SIMRA compounds are effective at modulating an immune response in vivo. More specifically, these data demonstrate that SIMRA compounds can induce effects on select immune cells.
Figure 15:
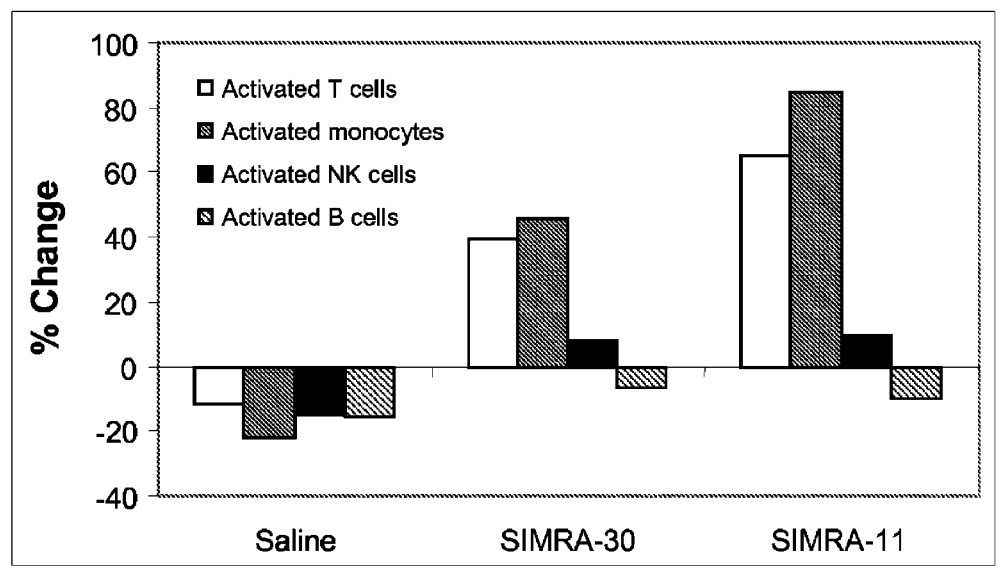
FIG. 15 depicts changes in activation marker CD69 on immune cells in Cynomolgus monkeys at 24 hours post dosing compared to 0 hours, as determined by Flow cytometry.

BALB/c mice were divided into groups of three mice. Cultured CT26.CL25 cells were injected intravenously (i.v.) ($4 \times 10^5$ cells/mouse). An RNA based oligonucleotide according to the invention (SIMRA compound) or controls were then administered subcutaneously (s.c.) to mice at a dose of 50 mg/kg. 4 hrs after $1^{st}$ dose administration, serum was taken from the mice and IL-12 levels were determined by ELISA. The results are shown in FIG. 9. The mice received further s.c. administrations 24 hrs, 72 hrs and 144 hrs after i.v. administration of the CT26.CL25 cells. On day 14 the mice were sacrificed and the lungs were collected. FIG. 10 shows the number of tumor nodules found in the lungs.

In Vivo Immune Response of RNA Based Oligonucleotides in Non-Human Primates

Cynomolgus monkeys were divided into 3 groups with four monkeys per group (two for saline group). RNA based oligonucleotide according to the invention (SIMRA compound) or controls were then administered subcutaneously (s.c.) to the monkeys at a dose of 5 mg/kg. Other dosages (e.g. 1 mg/kg) may also have a desired effect. 8, 16 and 24 hrs after administration, serum was taken from the monkeys and cytokine and chemokine levels and changes in the immune response were determined. The results are shown in FIGS. 12-15.

EQUIVALENTS

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed:

1. A biologically stable, biologically active agonist for TLR8, TLR7 and TLR8, or TLR7, consisting essentially of two single-stranded oligoribonucleotides linked through a 3'-3' attachment, wherein each of the oligoribonucleotides is 8 to 17 ribonucleotides in length, wherein the sequences of the oligoribonucleotides are identical, and wherein the agonist is not associated with a lipid, condensed with polyethylenimine, or complexed to DOTAP.

2. The agonist according to claim 1, wherein the oligoribonucleotides are linked directly to each other at their 3' ends.

3. The agonist according to claim 1, wherein the 3' ends of the oligoribonucleotides are linked to a non-nucleotidic linker.

4. The agonist according to claim 3, wherein the non-nucleotidic linker is an alkyl linker or amino linker, wherein the alkyl or amino linker may be optionally branched or unbranched, cyclic or acyclic, substituted or unsubstituted, saturated or unsaturated, chiral, achiral or racemic mixture.

5. The agonist according to claim 4, wherein the alkyl linker has from about 2 to about 18 carbon atoms.

6. The agonist according to claim 4, wherein the alkyl linker has from about 3 to about 9 carbon atoms.

7. The agonist according to claim 4, wherein the alkyl linker is 1,2,3-Propanetriol, glycerol, 1,2,4-Butanetriol, 2-Hydroxymethyl-1,3-proanediol, 1,1,1-Tris(hydroxymethyl)ethane, 2-Amino-2-(hydroxymethyl)1,3-proanediol, tris(hydroxymethyl)nitromethane, 1,1,1-Tri(hydroxymethyl)propane, 1,2,6-Hexanetriol, 1,3,5-Hexanetriol, 1,3,5-Pentanetriol, 3-Methyl-1,3,5-pentanetriol, 1,2,3-Heptanetriol, 2-(Hydroxymethyl)1,4-butanediol, 1,3-Di(hydroxymethyl)phenol, 1,3,5-Tri(hydroxymethyl)benzene, 1,3-Di(hydroxyethoxy)-2-hydroxy-propane, 1,3-Di(hydroxypropoxy)-2-hydroxy-propane, D-Galactal, 1,3,5-Tris(2-hydroxyethyl)cyanuric acid or 1,3,5-Tris(4-hydroxyphenyl)benzene.

8. The agonist according to claim 1, wherein the oligoribonucleotides comprises modified ribonucleotides.

9. The agonist according to claim 8, wherein the modified ribonucleotides are 7-deaza-G, ara-G, 6-thio-G, Inosine, Iso-G, loxoribine, TOG(7-thio-8-oxo)-G, 8-bromo-G, 8-hydroxy-G, 5-aminoformycin B, Oxoformycin, 7-methyl-G, 9-p-chlorophenyl-8-aza-G, 9-phenyl-G, 9-hexyl-guanine, 7-deaza-9-benzyl-G, 6-Chloro-7-deazaguanine, 6-methoxy-7-deazaguanine, 8-Aza-7-deaza-G(PPG), 2-(Dimethylamino)guanosine, 7-Methyl-6-thioguanosine, 8-Benzyloxyguanosine, 9-Deazaguanosine, 9-benzyl-8-hydroxy-2-(2-methoxyethoxy)adenine, 2-Amino-N2-O—, methyladenosine, 8-Aza-7-deaza-A, 7-deaza-A, Vidarabine, 2-Aminoadenosine, N1-Methyladenosine, 8-Azaadenosine, 5-Iodotubercidin, 1-(B-D-ribofuranosyl)-2-oxo-7-deaza-8-methyl-purine or 4-thio-U, or combinations thereof.

10. The agonist according to claim 1, further comprising a 5' cap.

11. The agonist according to claim 10, wherein the 5' cap is a non-nucleotidic linker.

12. The agonist according to claim 1, wherein each of the single-stranded oligoribonucleotides is 8, 9, 10, 11, 14, or 17 ribonucleotides in length.

13. The agonist according to claim 1, wherein each of the single-stranded oligoribonucleotides is 11 ribonucleotides in length.

14. The agonist according to claim 1, wherein the agonist is:
(a) 5'-UG$_1$CUG$_1$CUUCUG$_1$-X-G$_1$UCUUCG$_1$UCG$_1$U-5'; (5'-SEQ ID NO: 11-3'-X-3'-SEQ ID NO: 11-5'; SIMRA #11)
(b) 5'-X$_2$UGCUGCUUGUG-X-GUGUUCGUCGUX$_2$-5'; (5'-X$_2$SEQ ID NO: 30-3'-X-3'-SEQ ID NO: 30X$_2$-5'; SIMRA #30)
(c) 5'-X$_3$UGCUGCUGCUG-X-GUCGUCGUCGUX$_3$-5'; (5'-X$_3$SEQ ID NO: 41-3'-X-3'-SEQ ID NO: 41X$_3$-5'; SIMRA #41)
(d) 5'-UG$_1$CUG$_1$CUUCUG$_1$-X$_1$-G$_1$UCUUCG$_1$UCG$_1$U-5'; (5'-SEQ ID NO: 55-3'-X$_1$-3'-SEQ ID NO: 55-5'; SIMRA #55)
(e) 5'-UUG$_1$CUG$_1$UUG$_1$CU-X-UCG$_1$UUG$_1$UCG$_1$UU-5'; (5'-SEQ ID NO: 65-3'-X-3'-SEQ ID NO: 65-5'; SIMRA #65)
(f) 5'-UG$_1$CCUUG$_1$AACU-X-UCAAG$_1$UUCCG$_1$U-5'; (5'-SEQ ID NO: 66-3'-X-3'-SEQ ID NO: 66-5'; SIMRA #66)
(g) 5'-G$_1$UCCUUG$_1$CUUG$_1$-X-G$_1$UUCG$_1$UUCCUG$_1$-5'; (5'-SEQ ID NO: 105-3'-X-3'-SEQ ID NO: 105-5'; SIMRA #105)
(h) 5'-X$_2$G$_1$UCCUUG$_1$CUUG$_1$-X-G$_1$UUCG$_1$UU CCUG$_1$X$_2$-5'; (5'-X$_2$SEQ ID NO: 109-3'-X-3'-SEQ ID NO: 109X$_2$-5'; SIMRA #109)
(i) 5'-UG$_1$CUG$_1$CCUUUG$_1$-X-G$_1$UUUCCG$_1$UCG$_1$U-5'; (5'-SEQ ID NO: 110-3'-X-3'-SEQ ID NO: 110-5'; SIMRA #110) or
(j) 5'-G$_1$UCCUUUG$_1$CUG$_1$-X$_9$-G$_1$UCG$_1$UUUCCUG$_1$-5'; (5'-SEQ ID NO: 113-3'-X$_9$-3'-SEQ ID NO: 113-5'; SIMRA #113);
wherein G$_1$ is 7-deaza-G, X is glycerol, X$_2$ is a C3 linker or propanediol, X$_1$ is 1,3,5-pentanetriol, X$_3$ is a C3 linker or propanediol, X$_9$ is cis, trans-cyclohexanetriol.

* * * * *